US009061007B2

(12) United States Patent
Sahin et al.

(10) Patent No.: US 9,061,007 B2
(45) Date of Patent: Jun. 23, 2015

(54) COMPOSITIONS AND METHODS FOR THERAPY AND DIAGNOSIS OF CANCER AND CANCER METASTASIS

(71) Applicants: BioNTech AG, Mainz (DE); Johannes Gutenberg-Universität Mainz, Mainz (DE)

(72) Inventors: Ugur Sahin, Mainz (DE); Ozlem Tureci, Mainz (DE); Michael Koslowski, Mainz (DE)

(73) Assignees: JOHANNES GUTENBERG-UNIVERSITAT MAINZ, Mainz (DE); BIONTECH AG, Mainz (DE)

( * ) Notice: Subject to any disclaimer, the term of this patent is extended or adjusted under 35 U.S.C. 154(b) by 137 days.

(21) Appl. No.: 13/826,030

(22) Filed: Mar. 14, 2013

(65) Prior Publication Data

US 2013/0224214 A1 Aug. 29, 2013

Related U.S. Application Data

(63) Continuation of application No. 12/420,612, filed on Apr. 8, 2009, now abandoned, which is a continuation of application No. PCT/EP2007/008777, filed on Oct. 9, 2007.

(30) Foreign Application Priority Data

Oct. 12, 2006 (EP) .................................... 06021434

(51) Int. Cl.

| | |
|---|---|
| ***A61K 31/21*** | (2006.01) |
| ***A61K 39/395*** | (2006.01) |
| ***C12Q 1/68*** | (2006.01) |
| ***G01N 33/574*** | (2006.01) |
| ***A61K 31/7088*** | (2006.01) |
| *C12N 15/82* | (2006.01) |
| *A61K 47/48* | (2006.01) |

(52) U.S. Cl.

CPC ....... *A61K 39/39558* (2013.01); *C12N 15/8218* (2013.01); *A61K 47/484* (2013.01); *C12N 2310/11* (2013.01); *C12Q 1/6886* (2013.01); *C12Q 2600/118* (2013.01); *C12Q 2600/154* (2013.01); *C12Q 2600/158* (2013.01); *G01N 33/57484* (2013.01); *G01N 33/57492* (2013.01); *G01N 2333/715* (2013.01); *A61K 31/7088* (2013.01)

(58) Field of Classification Search

None

See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,837,028 | A | 6/1989 | Allen |
| 5,019,369 | A | 5/1991 | Presant et al. |
| 2010/0203040 | A1 | 8/2010 | Tuereci et al. |

FOREIGN PATENT DOCUMENTS

| | | | |
|---|---|---|---|
| WO | 92/04381 | A1 | 3/1992 |
| WO | WO 2005026205 | | 3/2005 |
| WO | WO 2006091112 | A1 | 8/2006 |

OTHER PUBLICATIONS

Dorsett et al, Nature Reviews Drug Discovery 3: 318 (Apr. 2004).*
International Preliminary Report on Patentability for International Patent Application Serial No. PCT/EP2007/008777, mailed Apr. 23, 2009.
"Affymetrix GeneChip Human Genome U133 Array Set HG-U133A" GEO Expression, Mar. 11, 2002, XP002361324.
Juarez et al., "Chemokines and their receptors as therapeutic targets: the role of the SDF-1/CXC$r axis" Current Pharmaceutical Design, vol. 10, No. 11, 2004, pp. 1245-1259.
Murakami et al., "Chemokine receptors and melanoma metastasis" Journal of Dermatological Science, Vo. 36, No. 2, Nov. 2004, pp. 71-78.
Luker et al., "Functions of CXCL2 and CXCR4 in breast cancer" Cancer Letters, vol. 238, No. 1, Jul. 8, 2006, pp. 30-41.
Mahadevan et al., "Transcript profiling in peripheral T-cell lymphoma, not otherwise specified and diffuse lart B-cell lymphoma identifies distinct tumor signatures" Molecular Cancer Therapeutics, vol. 4, No. 12, Dec. 2005, pp. 1867-1879.
Dong, et al., Identification of two novel CT antigens and their capacity to elicit antibody response in hepatocellular carcinoma patients, British Journal of Cancer (2003) 89, 291-297.
Sambrook and Russell, Molecular Cloning, A Laboratory Manual, Third Edition (2001) Cold Spring Harbor Laboratory Press, Cold Spring Harbor, New York, Information Panel 10.47.
Strausberg et al., In Microarrays and Cancer Research, (2002) Warrington et al (eds.), Eaton Publishing, Westborough, MA, pp. xi-xvi.
Notterman et al., In Microarrays and Cancer Research, (2002) Warrington et al (eds.), Eaton Publishing, Westborough, MA, pp. 81-111.
Dittmar,T. et al., FASEB J. 16, 1823-1825 (2002).
Ehrlich,M., Oncogene 21, 5400-5413 (2002).
Feinberg,A.P. & Vogelstein,B., Nature 301, 89-92 (1983).
Gardsvoll, J. Immunol. Methods 234: 107-116, 2000).
Goodman and Gilman, "The Pharmacological Basis of Therapeutics", 8th Edition, 1990, McGraw-Hill, Inc., pp. 1209-1263.
Halet,G., Biol. Cell 97, 501-518 (2005).
Harlow, E., et al. "Antibodies: A Laboratory Manual" ISBN:0879693142, pp. 141-245 (1988).
Koslowski,M. et al., Cancer Res. 62, 6750-6755 (2002).
Koslowski,M. et al., Cancer Res. 64, 5988-5993 (2004).

(Continued)

*Primary Examiner* — James Martinell

(74) *Attorney, Agent, or Firm* — McAndrews, Held & Malloy

(57) ABSTRACT

The present invention relates to methods which make possible to assess and/or prognose a cancer disease, the metastatic behavior of a cancer disease and/or the occurrence of a relapse of cancer. In particular, the methods of the invention make possible to assess and/or prognose the occurrence of cancer metastasis, in particular distant metastasis. Preferably, the methods of the invention allow to discriminate malign from benign conditions.

9 Claims, 8 Drawing Sheets

(56) References Cited

OTHER PUBLICATIONS

Lee, J.O. et al., Cell 99, 323-334 (1999).
Li, Z. et al., Nat. Cell Biol. 7, 399-404 (2005).
Meili, R., et al Nat. Cell Biol. 7, 334-335 (2005).
Muller,A. et al., Nature 410, 50-56 (2001).
Pearson and Lipman, 1988, Proc. Natl Acad. Sci. USA 85, 2444.
Rhee, I. et al., Nature 416, 552-556 (2002).
Staller,P. et al., Nature 425, 307-311 (2003).
Szoka et al. (1980), Ann. Rev. Biophys. Bioeng. 9 : 467.
Tall,E.G. et al., Curr. Biol. 10, 743-746 (2000).
Tamura, M. et al., Science 280, 1614-1617 (1998).
Walker,S.M. et al., Biochem. J. 360, 277-283 (2001).
Watton,S.J. & Downward,J., Curr. Biol. 9, 433-436 (1999).
Wu,Y. et al., J. Biol. Chem. 276, 21745-21753 (2001).

* cited by examiner

Figure 3 (cont`)
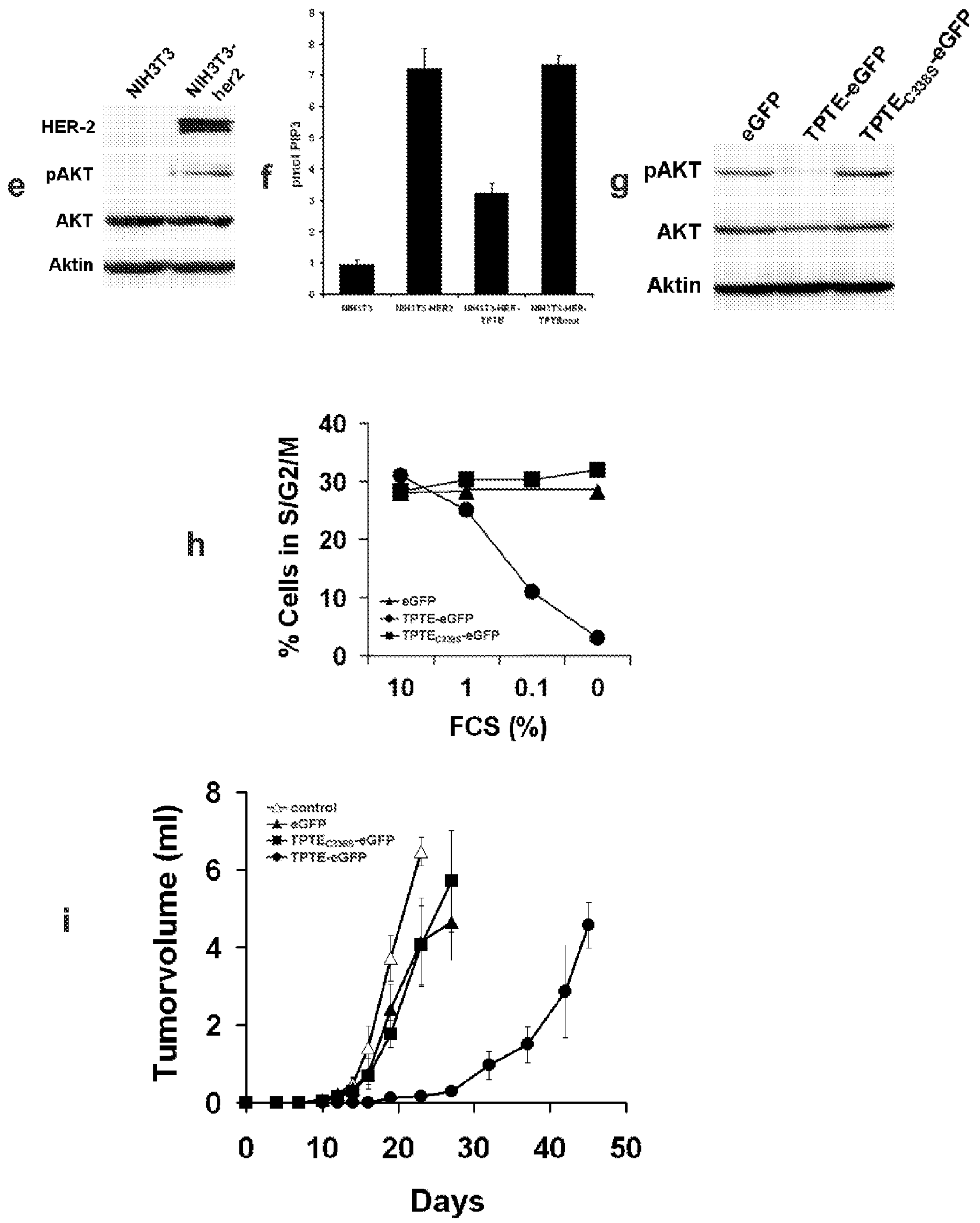

a b c d

Figure 4 (cont`)
e
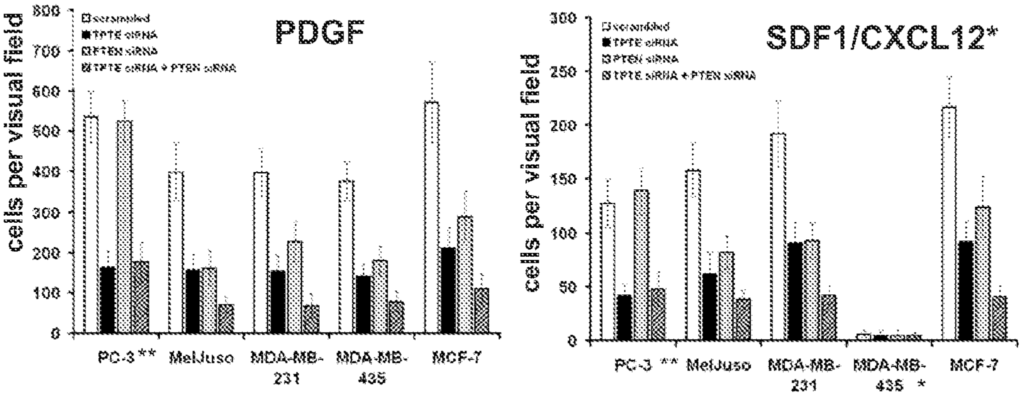
f
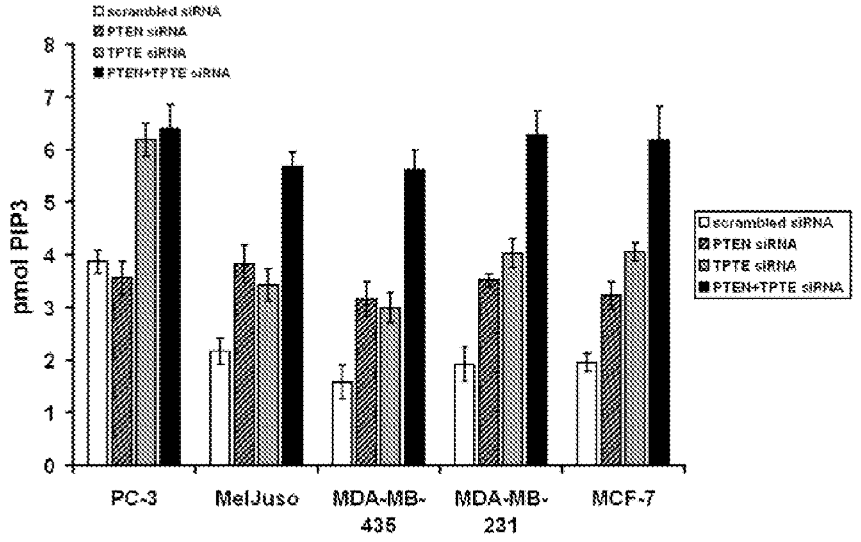
g
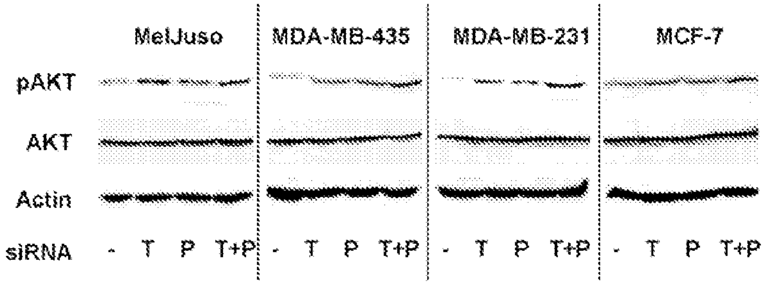
siRNA: -, scrambled control; T, TPTE; P, PTEN Figure 5 (cont`)
d
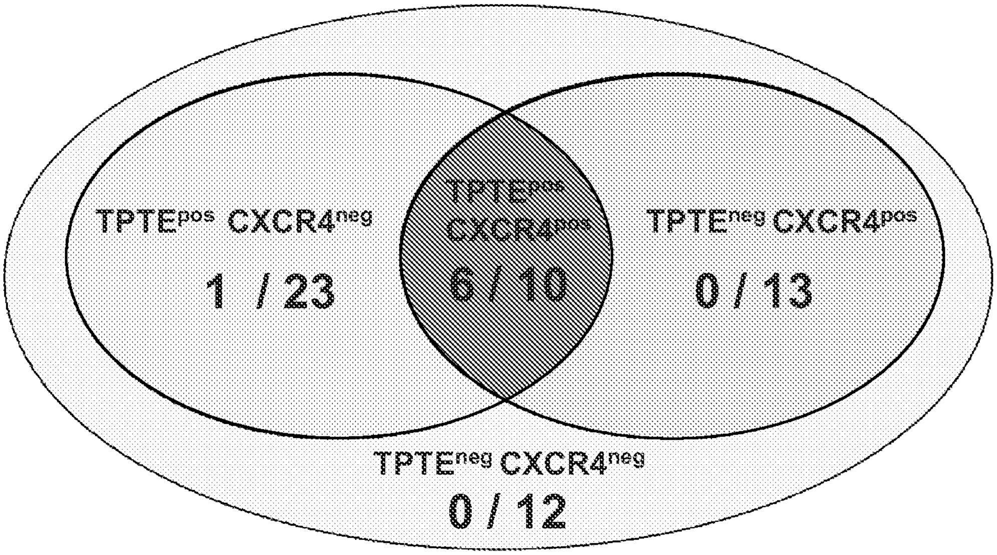
6 out of 10 in (TPTE$^{pos}$ AND CXCR4$^{pos}$ )
1 out of 48 in (TPTE$^{neg}$ OR CXCR4$^{neg}$) p=0,0000339

SEQUENCE LISTING

```
<160> NUMBER OF SEQ ID NOS: 52

<210> SEQ ID NO 1
<211> LENGTH: 2168
<212> TYPE: DNA
<213> ORGANISM: Homo sapiens

<400> SEQUENCE: 1
```

-continued

```
gaatccgcgg ggagggcaca acagctgcta cctgaacagt ttctgaccca acagttaccc     60
agcgccggac tcgctgcgcc ccggcggctc tagggacccc cggcgcctac acttagctcc    120
gcgcccgaga gaatgttgga ccgacgacac aagacctcag acttgtgtta ttctagcagc    180
tgaacacacc ccaggctctt ctgaccggca gtggctctgg aagcagtctg gtgtatagag    240
ttatggattc actaccagat tctactgtat gctcttgaca actatgacca caatggtcca    300
cccacaaatg aattatcagg agtgaaccca gaggcacgta tgaatgaaag tcctgatccg    360
actgacctgg cgggagtcat cattgagctc ggccccaatg acagtccaca gacaagtgaa    420
tttaaaggag caaccgagga ggcacctgcg aaagaaagcc cacacacaag tgaatttaaa    480
ggagcagccc gggtgtcacc tatcagtgaa agtgtgttag cacgactttc caagtttgaa    540
gttgaagatg ctgaaaatgt tgcttcatat gacagcaaga ttaagaaaat tgtgcattca    600
attgtatcat cctttgcatt tggactattt ggagttttcc tggtcttact ggatgtcact    660
ctcatccttg ccgacctaat tttcactgac agcaaacttt atattccttt ggagtatcgt    720
tctatttctc tagctattgc cttatttttt ctcatggatg ttcttcttcg agtatttgta    780
gaaaggagac agcagtattt ttctgactta tttaacattt tagatactgc cattattgtg    840
attcttctgc tggttgatgt cgtttacatt ttttttgaca ttaagttgct taggaatatt    900
cccagatgga cacatttact tcgacttcta cgacttatta ttctgttaag aatttttcat    960
ctgtttcatc aaaaaagaca acttgaaaag ctgataagaa ggcgggtttc agaaaacaaa   1020
aggcgataca caagggatgg atttgaccta gacctcactt acgttacaga acgtattatt   1080
gctatgtcat ttccatcttc tggaaggcag tctttctata gaaatccaat caaggaagtt   1140
gtgcggtttc tagataagaa acaccgaaac cactatcgag tctacaatct atgcagtgaa   1200
agagcttacg atcctaagca cttccataat agggtcgtta gaatcatgat tgatgatcat   1260
aatgtcccca ctctacatca gatggtggtt ttcaccaagg aagtaaatga gtggatggct   1320
caagatcttg aaaacatcgt agcgattcac tgtaaaggag gcacagatag aacaggaact   1380
atggtttgtg ccttccttat tgcctctgaa atatgttcaa ctgcaaagga aagcctgtat   1440
tattttggag aaaggcgaac agataaaacc cacagcgaaa aatttcaggg agtagaaact   1500
ccttctcaga agagatatgt tgcatatttt gcacaagtga aacatctcta caactggaat   1560
ctccctccaa gacggatact ctttataaaa cacttcatta tttattcgat tcctcgttat   1620
gtacgtgatc taaaaatcca aatagaaatg gagaaaaagg ttgtcttttc cactatttca   1680
ttaggaaaat gttcggtact tgataacatt acaacagaca aaatattaat tgatgtattc   1740
gacggtccac ctctgtatga tgatgtgaaa gtgcagtttt tctattcgaa tcttcctaca   1800
tactatgaca attgctcatt ttacttctgg ttgcacacat cttttattga aaataacagg   1860
ctttatctac caaaaaatga attggataat ctacataaac aaaaagcacg gagaatttat   1920
ccatcagatt ttgccgtgga gatacttttt ggcgagaaaa tgacttccag tgatgttgta   1980
gctggatccg attaagtata gctcccccttt ccccttctgg gaaagaatta tgttctttcc   2040
aaccctgcca catgttcata tatcctaaat ctatcctaaa tgttcccttg aagtatttat   2100
ttatgtttat atatgtttat acatgttctt caataaatct attacatata tataaaaaaa   2160
aaaaaaaa                                                              2168
```

<210> SEQ ID NO 2
<211> LENGTH: 2114
<212> TYPE: DNA

-continued

<213> ORGANISM: Homo sapiens

<400> SEQUENCE: 2
gaatccgcgg ggagggcaca acagctgcta cctgaacagt ttctgaccca acagttaccc 60
agcgccggac tcgctgcgcc ccggcggctc tagggacccc cggcgcctac acttagctcc 120
gcgcccgaga gaatgttgga ccgacgacac aagacctcag acttgtgtta ttctagcagc 180
tgaacacacc ccaggctctt ctgaccggca gtggctctgg aagcagtctg gtgtatagag 240
ttatggattc actaccagat tctactgtat gctcttgaca actatgacca caatggtcca 300
cccacaaatg aattatcagg agtgaaccca gaggcacgta tgaatgaaag tcctgatccg 360
actgacctgg cgggagtcat cattgagctc ggccccaatg acagtccaca gacaagtgaa 420
tttaaaggag caaccgagga ggcacctgcg aaagaaagtg tgttagcacg actttccaag 480
tttgaagttg aagatgctga aaatgttgct tcatatgaca gcaagattaa gaaaattgtg 540
cattcaattg tatcatcctt tgcatttgga ctatttggag ttttcctggt cttactggat 600
gtcactctca tccttgccga cctaatttc actgacagca aactttatat tcctttggag 660
tatcgttcta tttctctagc tattgcctta ttttttctca tggatgttct tcttcgagta 720
tttgtagaaa ggagacagca gtatttttct gacttattta acattttaga tactgccatt 780
attgtgattc ttctgctggt tgatgtcgtt tacatttttt ttgacattaa gttgcttagg 840
aatattccca gatggacaca tttacttcga cttctacgac ttattattct gttaagaatt 900
tttcatctgt ttcatcaaaa aagacaactt gaaaagctga taagaaggcg ggtttcagaa 960
aacaaaaggc gatacacaag ggatggattt gacctagacc tcacttacgt tacagaacgt 1020
attattgcta tgtcatttcc atcttctgga aggcagtctt tctatagaaa tccaatcaag 1080
gaagttgtgc ggtttctaga taagaaacac cgaaaccact atcgagtcta caatctatgc 1140
agtgaaagag cttacgatcc taagcacttc cataataggg tcgttagaat catgattgat 1200
gatcataatg tccccactct acatcagatg gtggttttca ccaaggaagt aaatgagtgg 1260
atggctcaag atcttgaaaa catcgtagcg attcactgta aaggaggcac agatagaaca 1320
ggaactatgg tttgtgcctt ccttattgcc tctgaaatat gttcaactgc aaaggaaagc 1380
ctgtattatt ttggagaaag gcgaacagat aaaacccaca gcgaaaaatt tcagggagta 1440
gaaactcctt ctcagaagag atatgttgca tattttgcac aagtgaaaca tctctacaac 1500
tggaatctcc ctccaagacg gatactcttt ataaaacact tcattattta ttcgattcct 1560
cgttatgtac gtgatctaaa aatccaaata gaaatggaga aaaaggttgt cttttccact 1620
atttcattag gaaaatgttc ggtacttgat aacattacaa cagacaaaat attaattgat 1680
gtattcgacg gtccacctct gtatgatgat gtgaaagtgc agtttttcta ttcgaatctt 1740
cctacatact atgacaattg ctcattttac ttctggttgc acacatcttt tattgaaaat 1800
aacaggcttt atctaccaaa aaatgaattg gataatctac ataaacaaaa agcacggaga 1860
atttatccat cagattttgc cgtggagata ctttttggcg agaaaatgac ttccagtgat 1920
gttgtagctg gatccgatta agtatagctc ccccttcccc ttctgggaaa gaattatgtt 1980
ctttccaacc ctgccacatg ttcatatatc ctaaatctat cctaaatgtt cccttgaagt 2040
atttatttat gtttatatat gtttatacat gttcttcaat aaatctatta catatatata 2100
aaaaaaaaaa aaaa 2114

<210> SEQ ID NO 3
<211> LENGTH: 2222

<212> TYPE: DNA
<213> ORGANISM: Homo sapiens

<400> SEQUENCE: 3

```
gaatccgcgg ggagggcaca acagctgcta cctgaacagt ttctgaccca acagttaccc     60
agcgccggac tcgctgcgcc ccggcggctc tagggacccc cggcgcctac acttagctcc    120
gcgcccgaga gaatgttgga ccgacgacac aagacctcag acttgtgtta ttctagcagc    180
tgaacacacc ccaggctctt ctgaccggca gtggctctgg aagcagtctg gtgtatagag    240
ttatggattc actaccagat tctactgtat gctcttgaca actatgacca caatggtcca    300
cccacaaatg aattatcagg agtgaaccca gaggcacgta tgaatgaaag tcctgatccg    360
actgacctgg cgggagtcat cattgagctc ggccccaatg acagtccaca gacaagtgaa    420
tttaaaggag caaccgagga ggcacctgcg aaagaaagcc cacacacaag tgaatttaaa    480
ggagcagccc gggtgtcacc tatcagtgaa agtgtgttag cacgactttc caagtttgaa    540
gttgaagatg ctgaaaatgt tgcttcatat gacagcaaga ttaagaaaat tgtgcattca    600
attgtatcat cctttgcatt tggactattt ggagttttcc tggtcttact ggatgtcact    660
ctcatccttg ccgacctaat tttcactgac agcaaacttt atattccttt ggagtatcgt    720
tctatttctc tagctattgc cttatttttt ctcatggatg ttcttcttcg agtatttgta    780
gaaaggagac agcagtattt ttctgactta tttaacattt tagatactgc cattattgtg    840
attcttctgc tggttgatgt cgtttacatt ttttttgaca ttaagttgct taggaatatt    900
cccagatgga cacatttact tcgacttcta cgacttatta ttctgttaag aatttttcat    960
ctgtttcatc aaaaaagaca acttgaaaag ctgataagaa ggcgggtttc agaaaacaaa   1020
aggcgataca caagggatgg atttgaccta gacctcactt acgttacaga acgtattatt   1080
gctatgtcat ttccatcttc tggaaggcag tctttctata gaaatccaat caaggaagtt   1140
gtgcggtttc tagataagaa acaccgaaac cactatcgag tctacaatct atgcagtatg   1200
tacattactc tatattgtgc tactgtagat agaaaacaga ttactgcacg tgaaagagct   1260
tacgatccta agcacttcca taatagggtc gttagaatca tgattgatga tcataatgtc   1320
cccactctac atcagatggt ggttttcacc aaggaagtaa atgagtggat ggctcaagat   1380
cttgaaaaca tcgtagcgat tcactgtaaa ggaggcacag atagaacagg aactatggtt   1440
tgtgccttcc ttattgcctc tgaaatatgt tcaactgcaa aggaaagcct gtattatttt   1500
ggagaaaggc gaacagataa aacccacagc gaaaaatttc agggagtaga aactccttct   1560
cagaagagat atgttgcata ttttgcacaa gtgaaacatc tctacaactg gaatctccct   1620
ccaagacgga tactctttat aaaacacttc attatttatt cgattcctcg ttatgtacgt   1680
gatctaaaaa tccaaataga aatggagaaa aaggttgtct tttccactat ttcattagga   1740
aaatgttcgg tacttgataa cattacaaca gacaaaatat taattgatgt attcgacggt   1800
ccacctctgt atgatgatgt gaaagtgcag tttttctatt cgaatcttcc tacatactat   1860
gacaattgct cattttactt ctggttgcac acatctttta ttgaaaataa caggctttat   1920
ctaccaaaaa atgaattgga taatctacat aaacaaaaag cacggagaat ttatccatca   1980
gattttgccg tggagatact ttttggcgag aaaatgactt ccagtgatgt tgtagctgga   2040
tccgattaag tatagctccc ccttcccctt ctgggaaaga attatgttct ttccaaccct   2100
gccacatgtt catatatcct aaatctatcc taaatgttcc cttgaagtat ttatttatgt   2160
ttatatatgt ttatacatgt tcttcaataa atctattaca tatatataaa aaaaaaaaaa   2220
```

-continued aa 2222

<210> SEQ ID NO 4
<211> LENGTH: 1550
<212> TYPE: DNA
<213> ORGANISM: Homo sapiens

<400> SEQUENCE: 4
atgaatgaaa gtcctgatcc gactgacctg gcgggagtca tcattgagct cggccccaat 60
gacagtccac agacaagtga atttaaagga gcaaccgagg aggcacctgc gaaagaaagc 120
ccacacacaa gtgaatttaa aggagcagcc cgggtgtcac ctatcagtga aagtgtgtta 180
gcacgacttt ccaagtttga agttgaagat gctgaaaatg ttgcttcata tgacagcaag 240
attaagaaaa ttgtgcattc aattgtatca tcctttgcat ttggactatt tggagttttc 300
ctggtcttac tggatgtcac tctcatcctt gccgacctaa ttttcactga cagcaaactt 360
tatattcctt tggagtatcg ttctatttct ctagctattg ccttattttt tctcatggat 420
gttcttcttc gagtatttgt agaaaggaga cagcagtatt tttctgactt atttaacatt 480
ttagatactg ccattattgt gattcttctg ctggttgatg tcgtttacat tttttttgac 540
attaagttgc ttaggaatat tcccagatgg acacatttac ttcgacttct acgacttatt 600
attctgttaa gaatttttca tctgtttcat caaaaaagac aacttgaaaa gctgataaga 660
aggcgggttt cagaaaacaa aaggcgatac acaagggatg gatttgacct agacctcact 720
tacgttacag aacgtattat tgctatgtca tttccatctt ctggaaggca gtctttctat 780
agaaatccaa tcaaggaagt tgtgcggttt ctagataaga aacaccgaaa ccactatcga 840
gtctacaatc tatgcagtga aagagcttac gatcctaagc acttccataa tagggtcgtt 900
agaatcatga ttgatgatca taatgtcccc actctacatc agatggtggt tttcaccaag 960
gaagtaaatg agtggatggc tcaagatctt gaaaacatcg tagcgattca ctgtaaagga 1020
ggcacagata gaacaggaac tatggtttgt gccttcctta ttgcctctga aatatgttca 1080
actgcaaagg aaagcctgta ttattttgga gaaaggcgaa cagataaaac ccacagcgaa 1140
aaatttcagg gagtagaaac tccttctcag gttatgtacg tgatctaaaa atccaaatag 1200
aaatggagaa aaaggttgtc ttttccacta tttcattagg aaaatgttcg gtacttgata 1260
acattacaac agacaaaata ttaattgatg tattcgacgg tccacctctg tatgatgatg 1320
tgaaagtgca gtttttctat tcgaatcttc ctacatacta tgacaattgc tcattttact 1380
tctggttgca cacatctttt attgaaaata acaggcttta tctaccaaaa aatgaattgg 1440
ataatctaca taaacaaaaa gcacggagaa tttatccatc agattttgcc gtggagatac 1500
tttttggcga gaaaatgact tccagtgatg ttgtagctgg atccgattaa 1550

<210> SEQ ID NO 5
<211> LENGTH: 1407
<212> TYPE: DNA
<213> ORGANISM: Homo sapiens

<400> SEQUENCE: 5
atgaatgaaa gtcctgatcc gactgacctg gcgggagtca tcattgagct cggccccaat 60
gacagtccac agacaagtga atttaaagga gcaaccgagg aggcacctgc gaaagaaagc 120
ccacacacaa gtgaatttaa aggagcagcc cgggtgtcac ctatcagtga aagtgtgtta 180
gcacgacttt ccaagtttga agttgaagat gctgaaaatg ttgcttcata tgacagcaag 240
attaagaaaa ttgtgcattc aattgtatca tcctttgcat ttggactatt tggagttttc 300

-continued

```
ctggtcttac tggatgtcac tctcatcctt gccgacctaa ttttcactga cagcaaactt    360
tatattcctt tggagtatcg ttctatttct ctagctattg ccttattttt tctcatggat    420
gttcttcttc gagtatttgt agaaaggaga cagcagtatt tttctgactt atttaacatt    480
ttagatactg ccattattgt gattcttctg ctggttgatg tcgtttacat tttttttgac    540
attaagttgc ttaggaatat tcccagatgg acacatttac ttcgacttct acgacttatt    600
attctgttaa gaatttttca tctgtttcat caaaaaagac aacttgaaaa gctgataaga    660
aggcgggttt cagaaaacaa aaggcgatac acaagggatg gatttgacct agacctcact    720
tacgttacag aacgtattat tgctatgtca tttccatctt ctggaaggca gtctttctat    780
agaaatccaa tcaaggaagt tgtgcggttt ctagataaga aacaccgaaa ccactatcga    840
gtctacaatc tatgcagtga aagagcttac gatcctaagc acttccataa tagggtcgtt    900
agaatcatga ttgatgatca taatgtcccc actctacatc agatggtggt tttcaccaag    960
gaagtaaatg agtggatggc tcaagatctt gaaaacatcg tagcgattca ctgtaaagga   1020
ggcacaggtt atgtacgtga tctaaaaatc caaatagaaa tggagaaaaa ggttgtcttt   1080
tccactattt cattaggaaa atgttcggta cttgataaca ttacaacaga caaaatatta   1140
attgatgtat tcgacggtcc acctctgtat gatgatgtga aagtgcagtt tttctattcg   1200
aatcttccta catactatga caattgctca ttttacttct ggttgcacac atcttttatt   1260
gaaaataaca ggctttatct accaaaaaat gaattggata atctacataa acaaaaagca   1320
cggagaattt atccatcaga ttttgccgtg gagatacttt ttggcgagaa aatgacttcc   1380
agtgatgttg tagctggatc cgattaa                                       1407
```

```
<210> SEQ ID NO 6
<211> LENGTH: 1413
<212> TYPE: DNA
<213> ORGANISM: Homo sapiens

<400> SEQUENCE: 6

atgaatgaaa gtcctgatcc gactgacctg gcgggagtca tcattgagct cggccccaat     60
gacagtccac agacaagtga atttaaagga gcaaccgagg aggcacctgc gaaagaaagt    120
gtgttagcac gactttccaa gtttgaagtt gaagatgctg aaaatgttgc ttcatatgac    180
agcaagatta agaaaattgt gcattcaatt gtatcatcct ttgcatttgg actatttgga    240
gttttcctgg tcttactgga tgtcactctc atccttgccg acctaatttt cactgacagc    300
aaactttata ttcctttgga gtatcgttct atttctctag ctattgcctt atttttttctc    360
atggatgttc ttcttcgagt atttgtagaa aggagacagc agtatttttc tgacttattt    420
aacattttag atactgccat tattgtgatt cttctgctgg ttgatgtcgt ttacattttt    480
tttgacatta agttgcttag gaatattccc agatggacac atttacttcg acttctacga    540
cttattattc tgttaagaat ttttcatctg tttcatcaaa aaagacaact tgaaaagctg    600
ataagaaggc gggtttcaga aaacaaaagg cgatacacaa gggatggatt tgacctagac    660
ctcacttacg ttacagaacg tattattgct atgtcatttc catcttctgg aaggcagtct    720
ttctatagaa atccaatcaa ggaagttgtg cggtttctag ataagaaaca ccgaaaccac    780
tatcgagtct acaatctatg cagtgaaaga gcttacgatc ctaagcactt ccataatagg    840
gtcgttagaa tcatgattga tgatcataat gtccccactc tacatcagat ggtggttttc    900
accaaggaag taaatgagtg gatggctcaa gatcttgaaa acatcgtagc gattcactgt    960
```

-continued

```
aaaggaggca cagatagaac aggaactatg gtttgtgcct tccttattgc ctctgaaata   1020

tgttcaactg caaaggaaag cctgtattat tttggagaaa ggcgaacaga taaaacccac   1080

agcgaaaaat ttcagggagt agaaactcct tctgtacttg ataacattac aacagacaaa   1140

atattaattg atgtattcga cggtccacct ctgtatgatg atgtgaaagt gcagtttttc   1200

tattcgaatc ttcctacata ctatgacaat tgctcatttt acttctggtt gcacacatct   1260

tttattgaaa ataacaggct ttatctacca aaaaatgaat tggataatct acataaacaa   1320

aaagcacgga gaatttatcc atcagatttt gccgtggaga tactttttgg cgagaaaatg   1380

acttccagtg atgttgtagc tggatccgat taa                                1413
```

<210> SEQ ID NO 7
<211> LENGTH: 1353
<212> TYPE: DNA
<213> ORGANISM: Homo sapiens

<400> SEQUENCE: 7

```
atgaatgaaa gtcctgatcc gactgacctg gcgggagtca tcattgagct cggccccaat     60

gacagtccac agacaagtga atttaaagga gcaaccgagg aggcacctgc gaaagaaagt    120

gtgttagcac gactttccaa gtttgaagtt gaagatgctg aaaatgttgc ttcatatgac    180

agcaagatta agaaaattgt gcattcaatt gtatcatcct ttgcatttgg actatttgga    240

gttttcctgg tcttactgga tgtcactctc atccttgccg acctaatttt cactgacagc    300

aaactttata ttcctttgga gtatcgttct atttctctag ctattgcctt atttttttctc    360

atggatgttc ttcttcgagt atttgtagaa aggagacagc agtatttttc tgacttattt    420

aacattttag atactgccat tattgtgatt cttctgctgg ttgatgtcgt ttacattttt    480

tttgacatta agttgcttag gaatattccc agatggacac atttacttcg acttctacga    540

cttattattc tgttaagaat ttttcatctg tttcatcaaa aaagacaact tgaaaagctg    600

ataagaaggc gggtttcaga aaacaaaagg cgatacacaa gggatggatt tgacctagac    660

ctcacttacg ttacagaacg tattattgct atgtcatttc catcttctgg aaggcagtct    720

ttctatagaa atccaatcaa ggaagttgtg cggtttctag ataagaaaca ccgaaaccac    780

tatcgagtct acaatctatg cagtgaaaga gcttacgatc ctaagcactt ccataatagg    840

gtcgttagaa tcatgattga tgatcataat gtccccactc tacatcagat ggtggttttc    900

accaaggaag taaatgagtg gatggctcaa gatcttgaaa acatcgtagc gattcactgt    960

aaaggaggca caggttatgt acgtgatcta aaaatccaaa tagaaatgga gaaaaaggtt   1020

gtcttttcca ctatttcatt aggaaaatgt tcggtacttg ataacattac aacagacaaa   1080

atattaattg atgtattcga cggtccacct ctgtatgatg atgtgaaagt gcagtttttc   1140

tattcgaatc ttcctacata ctatgacaat tgctcatttt acttctggtt gcacacatct   1200

tttattgaaa ataacaggct ttatctacca aaaaatgaat tggataatct acataaacaa   1260

aaagcacgga gaatttatcc atcagatttt gccgtggaga tactttttgg cgagaaaatg   1320

acttccagtg atgttgtagc tggatccgat taa                                1353
```

<210> SEQ ID NO 8
<211> LENGTH: 551
<212> TYPE: PRT
<213> ORGANISM: Homo sapiens

<400> SEQUENCE: 8

Met Asn Glu Ser Pro Asp Pro Thr Asp Leu Ala Gly Val Ile Ile Glu

-continued

```
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Pro His Thr Ser Glu Phe Lys Gly
        35                  40                  45

Ala Ala Arg Val Ser Pro Ile Ser Glu Ser Val Leu Ala Arg Leu Ser
    50                  55                  60

Lys Phe Glu Val Glu Asp Ala Glu Asn Val Ala Ser Tyr Asp Ser Lys
65                  70                  75                  80

Ile Lys Lys Ile Val His Ser Ile Val Ser Ser Phe Ala Phe Gly Leu
                85                  90                  95

Phe Gly Val Phe Leu Val Leu Leu Asp Val Thr Leu Ile Leu Ala Asp
            100                 105                 110

Leu Ile Phe Thr Asp Ser Lys Leu Tyr Ile Pro Leu Glu Tyr Arg Ser
        115                 120                 125

Ile Ser Leu Ala Ile Ala Leu Phe Phe Leu Met Asp Val Leu Leu Arg
    130                 135                 140

Val Phe Val Glu Arg Arg Gln Gln Tyr Phe Ser Asp Leu Phe Asn Ile
145                 150                 155                 160

Leu Asp Thr Ala Ile Ile Val Ile Leu Leu Leu Val Asp Val Val Tyr
                165                 170                 175

Ile Phe Phe Asp Ile Lys Leu Leu Arg Asn Ile Pro Arg Trp Thr His
            180                 185                 190

Leu Leu Arg Leu Leu Arg Leu Ile Ile Leu Leu Arg Ile Phe His Leu
        195                 200                 205

Phe His Gln Lys Arg Gln Leu Glu Lys Leu Ile Arg Arg Arg Val Ser
    210                 215                 220

Glu Asn Lys Arg Arg Tyr Thr Arg Asp Gly Phe Asp Leu Asp Leu Thr
225                 230                 235                 240

Tyr Val Thr Glu Arg Ile Ile Ala Met Ser Phe Pro Ser Ser Gly Arg
                245                 250                 255

Gln Ser Phe Tyr Arg Asn Pro Ile Lys Glu Val Val Arg Phe Leu Asp
            260                 265                 270

Lys Lys His Arg Asn His Tyr Arg Val Tyr Asn Leu Cys Ser Glu Arg
        275                 280                 285

Ala Tyr Asp Pro Lys His Phe His Asn Arg Val Val Arg Ile Met Ile
    290                 295                 300

Asp Asp His Asn Val Pro Thr Leu His Gln Met Val Val Phe Thr Lys
305                 310                 315                 320

Glu Val Asn Glu Trp Met Ala Gln Asp Leu Glu Asn Ile Val Ala Ile
                325                 330                 335

His Cys Lys Gly Gly Thr Asp Arg Thr Gly Thr Met Val Cys Ala Phe
            340                 345                 350

Leu Ile Ala Ser Glu Ile Cys Ser Thr Ala Lys Glu Ser Leu Tyr Tyr
        355                 360                 365

Phe Gly Glu Arg Arg Thr Asp Lys Thr His Ser Glu Lys Phe Gln Gly
    370                 375                 380

Val Glu Thr Pro Ser Gln Lys Arg Tyr Val Ala Tyr Phe Ala Gln Val
385                 390                 395                 400

Lys His Leu Tyr Asn Trp Asn Leu Pro Pro Arg Arg Ile Leu Phe Ile
                405                 410                 415

Lys His Phe Ile Ile Tyr Ser Ile Pro Arg Tyr Val Arg Asp Leu Lys
            420                 425                 430
```

```
Ile Gln Ile Glu Met Glu Lys Lys Val Val Phe Ser Thr Ile Ser Leu
        435                 440                 445

Gly Lys Cys Ser Val Leu Asp Asn Ile Thr Thr Asp Lys Ile Leu Ile
    450                 455                 460

Asp Val Phe Asp Gly Pro Pro Leu Tyr Asp Asp Val Lys Val Gln Phe
465                 470                 475                 480

Phe Tyr Ser Asn Leu Pro Thr Tyr Tyr Asp Asn Cys Ser Phe Tyr Phe
                485                 490                 495

Trp Leu His Thr Ser Phe Ile Glu Asn Asn Arg Leu Tyr Leu Pro Lys
            500                 505                 510

Asn Glu Leu Asp Asn Leu His Lys Gln Lys Ala Arg Arg Ile Tyr Pro
        515                 520                 525

Ser Asp Phe Ala Val Glu Ile Leu Phe Gly Glu Lys Met Thr Ser Ser
    530                 535                 540

Asp Val Val Ala Gly Ser Asp
545                 550


<210> SEQ ID NO 9
<211> LENGTH: 533
<212> TYPE: PRT
<213> ORGANISM: Homo sapiens

<400> SEQUENCE: 9

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Val Leu Ala Arg Leu Ser Lys Phe
        35                  40                  45

Glu Val Glu Asp Ala Glu Asn Val Ala Ser Tyr Asp Ser Lys Ile Lys
    50                  55                  60

Lys Ile Val His Ser Ile Val Ser Ser Phe Ala Phe Gly Leu Phe Gly
65                  70                  75                  80

Val Phe Leu Val Leu Leu Asp Val Thr Leu Ile Leu Ala Asp Leu Ile
                85                  90                  95

Phe Thr Asp Ser Lys Leu Tyr Ile Pro Leu Glu Tyr Arg Ser Ile Ser
            100                 105                 110

Leu Ala Ile Ala Leu Phe Phe Leu Met Asp Val Leu Leu Arg Val Phe
        115                 120                 125

Val Glu Arg Arg Gln Gln Tyr Phe Ser Asp Leu Phe Asn Ile Leu Asp
    130                 135                 140

Thr Ala Ile Ile Val Ile Leu Leu Leu Val Asp Val Val Tyr Ile Phe
145                 150                 155                 160

Phe Asp Ile Lys Leu Leu Arg Asn Ile Pro Arg Trp Thr His Leu Leu
                165                 170                 175

Arg Leu Leu Arg Leu Ile Ile Leu Leu Arg Ile Phe His Leu Phe His
            180                 185                 190

Gln Lys Arg Gln Leu Glu Lys Leu Ile Arg Arg Arg Val Ser Glu Asn
        195                 200                 205

Lys Arg Arg Tyr Thr Arg Asp Gly Phe Asp Leu Asp Leu Thr Tyr Val
    210                 215                 220

Thr Glu Arg Ile Ile Ala Met Ser Phe Pro Ser Ser Gly Arg Gln Ser
225                 230                 235                 240

Phe Tyr Arg Asn Pro Ile Lys Glu Val Val Arg Phe Leu Asp Lys Lys
```

```
                245                 250                 255

His Arg Asn His Tyr Arg Val Tyr Asn Leu Cys Ser Glu Arg Ala Tyr
            260                 265                 270

Asp Pro Lys His Phe His Asn Arg Val Val Arg Ile Met Ile Asp Asp
        275                 280                 285

His Asn Val Pro Thr Leu His Gln Met Val Val Phe Thr Lys Glu Val
    290                 295                 300

Asn Glu Trp Met Ala Gln Asp Leu Glu Asn Ile Val Ala Ile His Cys
305                 310                 315                 320

Lys Gly Gly Thr Asp Arg Thr Gly Thr Met Val Cys Ala Phe Leu Ile
                325                 330                 335

Ala Ser Glu Ile Cys Ser Thr Ala Lys Glu Ser Leu Tyr Tyr Phe Gly
            340                 345                 350

Glu Arg Arg Thr Asp Lys Thr His Ser Glu Lys Phe Gln Gly Val Glu
        355                 360                 365

Thr Pro Ser Gln Lys Arg Tyr Val Ala Tyr Phe Ala Gln Val Lys His
    370                 375                 380

Leu Tyr Asn Trp Asn Leu Pro Pro Arg Arg Ile Leu Phe Ile Lys His
385                 390                 395                 400

Phe Ile Ile Tyr Ser Ile Pro Arg Tyr Val Arg Asp Leu Lys Ile Gln
                405                 410                 415

Ile Glu Met Glu Lys Lys Val Val Phe Ser Thr Ile Ser Leu Gly Lys
            420                 425                 430

Cys Ser Val Leu Asp Asn Ile Thr Thr Asp Lys Ile Leu Ile Asp Val
        435                 440                 445

Phe Asp Gly Pro Pro Leu Tyr Asp Asp Val Lys Val Gln Phe Phe Tyr
    450                 455                 460

Ser Asn Leu Pro Thr Tyr Tyr Asp Asn Cys Ser Phe Tyr Phe Trp Leu
465                 470                 475                 480

His Thr Ser Phe Ile Glu Asn Asn Arg Leu Tyr Leu Pro Lys Asn Glu
                485                 490                 495

Leu Asp Asn Leu His Lys Gln Lys Ala Arg Arg Ile Tyr Pro Ser Asp
            500                 505                 510

Phe Ala Val Glu Ile Leu Phe Gly Glu Lys Met Thr Ser Ser Asp Val
        515                 520                 525

Val Ala Gly Ser Asp
    530


<210> SEQ ID NO 10
<211> LENGTH: 569
<212> TYPE: PRT
<213> ORGANISM: Homo sapiens

<400> SEQUENCE: 10

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Pro His Thr Ser Glu Phe Lys Gly
        35                  40                  45

Ala Ala Arg Val Ser Pro Ile Ser Glu Ser Val Leu Ala Arg Leu Ser
    50                  55                  60

Lys Phe Glu Val Glu Asp Ala Glu Asn Val Ala Ser Tyr Asp Ser Lys
65                  70                  75                  80
```

-continued

```
Ile Lys Lys Ile Val His Ser Ile Val Ser Ser Phe Ala Phe Gly Leu
                85                  90                  95

Phe Gly Val Phe Leu Val Leu Leu Asp Val Thr Leu Ile Leu Ala Asp
            100                 105                 110

Leu Ile Phe Thr Asp Ser Lys Leu Tyr Ile Pro Leu Glu Tyr Arg Ser
        115                 120                 125

Ile Ser Leu Ala Ile Ala Leu Phe Phe Leu Met Asp Val Leu Leu Arg
    130                 135                 140

Val Phe Val Glu Arg Arg Gln Gln Tyr Phe Ser Asp Leu Phe Asn Ile
145                 150                 155                 160

Leu Asp Thr Ala Ile Ile Val Ile Leu Leu Leu Val Asp Val Val Tyr
                165                 170                 175

Ile Phe Phe Asp Ile Lys Leu Leu Arg Asn Ile Pro Arg Trp Thr His
            180                 185                 190

Leu Leu Arg Leu Leu Arg Leu Ile Ile Leu Leu Arg Ile Phe His Leu
        195                 200                 205

Phe His Gln Lys Arg Gln Leu Glu Lys Leu Ile Arg Arg Arg Val Ser
    210                 215                 220

Glu Asn Lys Arg Arg Tyr Thr Arg Asp Gly Phe Asp Leu Asp Leu Thr
225                 230                 235                 240

Tyr Val Thr Glu Arg Ile Ile Ala Met Ser Phe Pro Ser Ser Gly Arg
                245                 250                 255

Gln Ser Phe Tyr Arg Asn Pro Ile Lys Glu Val Val Arg Phe Leu Asp
            260                 265                 270

Lys Lys His Arg Asn His Tyr Arg Val Tyr Asn Leu Cys Ser Met Tyr
        275                 280                 285

Ile Thr Leu Tyr Cys Ala Thr Val Asp Arg Lys Gln Ile Thr Ala Arg
    290                 295                 300

Glu Arg Ala Tyr Asp Pro Lys His Phe His Asn Arg Val Val Arg Ile
305                 310                 315                 320

Met Ile Asp Asp His Asn Val Pro Thr Leu His Gln Met Val Val Phe
                325                 330                 335

Thr Lys Glu Val Asn Glu Trp Met Ala Gln Asp Leu Glu Asn Ile Val
            340                 345                 350

Ala Ile His Cys Lys Gly Gly Thr Asp Arg Thr Gly Thr Met Val Cys
        355                 360                 365

Ala Phe Leu Ile Ala Ser Glu Ile Cys Ser Thr Ala Lys Glu Ser Leu
    370                 375                 380

Tyr Tyr Phe Gly Glu Arg Arg Thr Asp Lys Thr His Ser Glu Lys Phe
385                 390                 395                 400

Gln Gly Val Glu Thr Pro Ser Gln Lys Arg Tyr Val Ala Tyr Phe Ala
                405                 410                 415

Gln Val Lys His Leu Tyr Asn Trp Asn Leu Pro Pro Arg Arg Ile Leu
            420                 425                 430

Phe Ile Lys His Phe Ile Ile Tyr Ser Ile Pro Arg Tyr Val Arg Asp
        435                 440                 445

Leu Lys Ile Gln Ile Glu Met Glu Lys Lys Val Val Phe Ser Thr Ile
    450                 455                 460

Ser Leu Gly Lys Cys Ser Val Leu Asp Asn Ile Thr Thr Asp Lys Ile
465                 470                 475                 480

Leu Ile Asp Val Phe Asp Gly Pro Pro Leu Tyr Asp Asp Val Lys Val
                485                 490                 495

Gln Phe Phe Tyr Ser Asn Leu Pro Thr Tyr Tyr Asp Asn Cys Ser Phe
```

```
            500                 505                 510

Tyr Phe Trp Leu His Thr Ser Phe Ile Glu Asn Asn Arg Leu Tyr Leu
        515                 520                 525

Pro Lys Asn Glu Leu Asp Asn Leu His Lys Gln Lys Ala Arg Arg Ile
    530                 535                 540

Tyr Pro Ser Asp Phe Ala Val Glu Ile Leu Phe Gly Glu Lys Met Thr
545                 550                 555                 560

Ser Ser Asp Val Val Ala Gly Ser Asp
                565


<210> SEQ ID NO 11
<211> LENGTH: 395
<212> TYPE: PRT
<213> ORGANISM: Homo sapiens

<400> SEQUENCE: 11

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Pro His Thr Ser Glu Phe Lys Gly
        35                  40                  45

Ala Ala Arg Val Ser Pro Ile Ser Glu Ser Val Leu Ala Arg Leu Ser
    50                  55                  60

Lys Phe Glu Val Glu Asp Ala Glu Asn Val Ala Ser Tyr Asp Ser Lys
65                  70                  75                  80

Ile Lys Lys Ile Val His Ser Ile Val Ser Ser Phe Ala Phe Gly Leu
                85                  90                  95

Phe Gly Val Phe Leu Val Leu Leu Asp Val Thr Leu Ile Leu Ala Asp
            100                 105                 110

Leu Ile Phe Thr Asp Ser Lys Leu Tyr Ile Pro Leu Glu Tyr Arg Ser
        115                 120                 125

Ile Ser Leu Ala Ile Ala Leu Phe Phe Leu Met Asp Val Leu Leu Arg
    130                 135                 140

Val Phe Val Glu Arg Arg Gln Gln Tyr Phe Ser Asp Leu Phe Asn Ile
145                 150                 155                 160

Leu Asp Thr Ala Ile Ile Val Ile Leu Leu Leu Val Asp Val Val Tyr
                165                 170                 175

Ile Phe Phe Asp Ile Lys Leu Leu Arg Asn Ile Pro Arg Trp Thr His
            180                 185                 190

Leu Leu Arg Leu Leu Arg Leu Ile Ile Leu Leu Arg Ile Phe His Leu
        195                 200                 205

Phe His Gln Lys Arg Gln Leu Glu Lys Leu Ile Arg Arg Arg Val Ser
    210                 215                 220

Glu Asn Lys Arg Arg Tyr Thr Arg Asp Gly Phe Asp Leu Asp Leu Thr
225                 230                 235                 240

Tyr Val Thr Glu Arg Ile Ile Ala Met Ser Phe Pro Ser Ser Gly Arg
                245                 250                 255

Gln Ser Phe Tyr Arg Asn Pro Ile Lys Glu Val Val Arg Phe Leu Asp
            260                 265                 270

Lys Lys His Arg Asn His Tyr Arg Val Tyr Asn Leu Cys Ser Glu Arg
        275                 280                 285

Ala Tyr Asp Pro Lys His Phe His Asn Arg Val Val Arg Ile Met Ile
    290                 295                 300
```

-continued

Asp Asp His Asn Val Pro Thr Leu His Gln Met Val Val Phe Thr Lys
305 310 315 320

Glu Val Asn Glu Trp Met Ala Gln Asp Leu Glu Asn Ile Val Ala Ile
325 330 335

His Cys Lys Gly Gly Thr Asp Arg Thr Gly Thr Met Val Cys Ala Phe
340 345 350

Leu Ile Ala Ser Glu Ile Cys Ser Thr Ala Lys Glu Ser Leu Tyr Tyr
355 360 365

Phe Gly Glu Arg Arg Thr Asp Lys Thr His Ser Glu Lys Phe Gln Gly
370 375 380

Val Glu Thr Pro Ser Gln Val Met Tyr Val Ile
385 390 395

<210> SEQ ID NO 12
<211> LENGTH: 468
<212> TYPE: PRT
<213> ORGANISM: Homo sapiens

<400> SEQUENCE: 12

Met Asn Glu Ser Pro Asp Pro Thr Asp Leu Ala Gly Val Ile Ile Glu
1 5 10 15

Leu Gly Pro Asn Asp Ser Pro Gln Thr Ser Glu Phe Lys Gly Ala Thr
20 25 30

Glu Glu Ala Pro Ala Lys Glu Ser Pro His Thr Ser Glu Phe Lys Gly
35 40 45

Ala Ala Arg Val Ser Pro Ile Ser Glu Ser Val Leu Ala Arg Leu Ser
50 55 60

Lys Phe Glu Val Glu Asp Ala Glu Asn Val Ala Ser Tyr Asp Ser Lys
65 70 75 80

Ile Lys Lys Ile Val His Ser Ile Val Ser Ser Phe Ala Phe Gly Leu
85 90 95

Phe Gly Val Phe Leu Val Leu Leu Asp Val Thr Leu Ile Leu Ala Asp
100 105 110

Leu Ile Phe Thr Asp Ser Lys Leu Tyr Ile Pro Leu Glu Tyr Arg Ser
115 120 125

Ile Ser Leu Ala Ile Ala Leu Phe Phe Leu Met Asp Val Leu Leu Arg
130 135 140

Val Phe Val Glu Arg Arg Gln Gln Tyr Phe Ser Asp Leu Phe Asn Ile
145 150 155 160

Leu Asp Thr Ala Ile Ile Val Ile Leu Leu Leu Val Asp Val Val Tyr
165 170 175

Ile Phe Phe Asp Ile Lys Leu Leu Arg Asn Ile Pro Arg Trp Thr His
180 185 190

Leu Leu Arg Leu Leu Arg Leu Ile Ile Leu Leu Arg Ile Phe His Leu
195 200 205

Phe His Gln Lys Arg Gln Leu Glu Lys Leu Ile Arg Arg Arg Val Ser
210 215 220

Glu Asn Lys Arg Arg Tyr Thr Arg Asp Gly Phe Asp Leu Asp Leu Thr
225 230 235 240

Tyr Val Thr Glu Arg Ile Ile Ala Met Ser Phe Pro Ser Ser Gly Arg
245 250 255

Gln Ser Phe Tyr Arg Asn Pro Ile Lys Glu Val Val Arg Phe Leu Asp
260 265 270

Lys Lys His Arg Asn His Tyr Arg Val Tyr Asn Leu Cys Ser Glu Arg
275 280 285

```
Ala Tyr Asp Pro Lys His Phe His Asn Arg Val Val Arg Ile Met Ile
    290                 295                 300

Asp Asp His Asn Val Pro Thr Leu His Gln Met Val Val Phe Thr Lys
305                 310                 315                 320

Glu Val Asn Glu Trp Met Ala Gln Asp Leu Glu Asn Ile Val Ala Ile
                325                 330                 335

His Cys Lys Gly Gly Thr Gly Tyr Val Arg Asp Leu Lys Ile Gln Ile
            340                 345                 350

Glu Met Glu Lys Lys Val Val Phe Ser Thr Ile Ser Leu Gly Lys Cys
        355                 360                 365

Ser Val Leu Asp Asn Ile Thr Thr Asp Lys Ile Leu Ile Asp Val Phe
    370                 375                 380

Asp Gly Pro Pro Leu Tyr Asp Asp Val Lys Val Gln Phe Phe Tyr Ser
385                 390                 395                 400

Asn Leu Pro Thr Tyr Tyr Asp Asn Cys Ser Phe Tyr Phe Trp Leu His
                405                 410                 415

Thr Ser Phe Ile Glu Asn Asn Arg Leu Tyr Leu Pro Lys Asn Glu Leu
            420                 425                 430

Asp Asn Leu His Lys Gln Lys Ala Arg Arg Ile Tyr Pro Ser Asp Phe
        435                 440                 445

Ala Val Glu Ile Leu Phe Gly Glu Lys Met Thr Ser Ser Asp Val Val
    450                 455                 460

Ala Gly Ser Asp
465


<210> SEQ ID NO 13
<211> LENGTH: 470
<212> TYPE: PRT
<213> ORGANISM: Homo sapiens

<400> SEQUENCE: 13

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Val Leu Ala Arg Leu Ser Lys Phe
        35                  40                  45

Glu Val Glu Asp Ala Glu Asn Val Ala Ser Tyr Asp Ser Lys Ile Lys
    50                  55                  60

Lys Ile Val His Ser Ile Val Ser Ser Phe Ala Phe Gly Leu Phe Gly
65                  70                  75                  80

Val Phe Leu Val Leu Leu Asp Val Thr Leu Ile Leu Ala Asp Leu Ile
                85                  90                  95

Phe Thr Asp Ser Lys Leu Tyr Ile Pro Leu Glu Tyr Arg Ser Ile Ser
            100                 105                 110

Leu Ala Ile Ala Leu Phe Phe Leu Met Asp Val Leu Leu Arg Val Phe
        115                 120                 125

Val Glu Arg Arg Gln Gln Tyr Phe Ser Asp Leu Phe Asn Ile Leu Asp
    130                 135                 140

Thr Ala Ile Ile Val Ile Leu Leu Leu Val Asp Val Val Tyr Ile Phe
145                 150                 155                 160

Phe Asp Ile Lys Leu Leu Arg Asn Ile Pro Arg Trp Thr His Leu Leu
                165                 170                 175

Arg Leu Leu Arg Leu Ile Ile Leu Leu Arg Ile Phe His Leu Phe His
```

```
            180                 185                 190

Gln Lys Arg Gln Leu Glu Lys Leu Ile Arg Arg Arg Val Ser Glu Asn
        195                 200                 205

Lys Arg Arg Tyr Thr Arg Asp Gly Phe Asp Leu Asp Leu Thr Tyr Val
    210                 215                 220

Thr Glu Arg Ile Ile Ala Met Ser Phe Pro Ser Ser Gly Arg Gln Ser
225                 230                 235                 240

Phe Tyr Arg Asn Pro Ile Lys Glu Val Val Arg Phe Leu Asp Lys Lys
                245                 250                 255

His Arg Asn His Tyr Arg Val Tyr Asn Leu Cys Ser Glu Arg Ala Tyr
            260                 265                 270

Asp Pro Lys His Phe His Asn Arg Val Val Arg Ile Met Ile Asp Asp
        275                 280                 285

His Asn Val Pro Thr Leu His Gln Met Val Val Phe Thr Lys Glu Val
    290                 295                 300

Asn Glu Trp Met Ala Gln Asp Leu Glu Asn Ile Val Ala Ile His Cys
305                 310                 315                 320

Lys Gly Gly Thr Asp Arg Thr Gly Thr Met Val Cys Ala Phe Leu Ile
                325                 330                 335

Ala Ser Glu Ile Cys Ser Thr Ala Lys Glu Ser Leu Tyr Tyr Phe Gly
            340                 345                 350

Glu Arg Arg Thr Asp Lys Thr His Ser Glu Lys Phe Gln Gly Val Glu
        355                 360                 365

Thr Pro Ser Val Leu Asp Asn Ile Thr Thr Asp Lys Ile Leu Ile Asp
    370                 375                 380

Val Phe Asp Gly Pro Pro Leu Tyr Asp Asp Val Lys Val Gln Phe Phe
385                 390                 395                 400

Tyr Ser Asn Leu Pro Thr Tyr Tyr Asp Asn Cys Ser Phe Tyr Phe Trp
                405                 410                 415

Leu His Thr Ser Phe Ile Glu Asn Asn Arg Leu Tyr Leu Pro Lys Asn
            420                 425                 430

Glu Leu Asp Asn Leu His Lys Gln Lys Ala Arg Arg Ile Tyr Pro Ser
        435                 440                 445

Asp Phe Ala Val Glu Ile Leu Phe Gly Glu Lys Met Thr Ser Ser Asp
    450                 455                 460

Val Val Ala Gly Ser Asp
465                 470


<210> SEQ ID NO 14
<211> LENGTH: 450
<212> TYPE: PRT
<213> ORGANISM: Homo sapiens

<400> SEQUENCE: 14

Met Asn Glu Ser Pro Asp Pro Thr Asp Leu Ala Gly Val Ile Ile Glu
1               5                   10                  15

Leu Gly Pro Asn Asp Ser Pro Gln Thr Ser Glu Phe Lys Gly Ala Thr
            20                  25                  30

Glu Glu Ala Pro Ala Lys Glu Ser Val Leu Ala Arg Leu Ser Lys Phe
        35                  40                  45

Glu Val Glu Asp Ala Glu Asn Val Ala Ser Tyr Asp Ser Lys Ile Lys
    50                  55                  60

Lys Ile Val His Ser Ile Val Ser Ser Phe Ala Phe Gly Leu Phe Gly
65                  70                  75                  80
```

```
Val Phe Leu Val Leu Leu Asp Val Thr Leu Ile Leu Ala Asp Leu Ile
                85                  90                  95

Phe Thr Asp Ser Lys Leu Tyr Ile Pro Leu Glu Tyr Arg Ser Ile Ser
            100                 105                 110

Leu Ala Ile Ala Leu Phe Phe Leu Met Asp Val Leu Leu Arg Val Phe
        115                 120                 125

Val Glu Arg Arg Gln Gln Tyr Phe Ser Asp Leu Phe Asn Ile Leu Asp
    130                 135                 140

Thr Ala Ile Ile Val Ile Leu Leu Leu Val Asp Val Val Tyr Ile Phe
145                 150                 155                 160

Phe Asp Ile Lys Leu Leu Arg Asn Ile Pro Arg Trp Thr His Leu Leu
                165                 170                 175

Arg Leu Leu Arg Leu Ile Ile Leu Leu Arg Ile Phe His Leu Phe His
            180                 185                 190

Gln Lys Arg Gln Leu Glu Lys Leu Ile Arg Arg Arg Val Ser Glu Asn
        195                 200                 205

Lys Arg Arg Tyr Thr Arg Asp Gly Phe Asp Leu Asp Leu Thr Tyr Val
    210                 215                 220

Thr Glu Arg Ile Ile Ala Met Ser Phe Pro Ser Ser Gly Arg Gln Ser
225                 230                 235                 240

Phe Tyr Arg Asn Pro Ile Lys Glu Val Val Arg Phe Leu Asp Lys Lys
                245                 250                 255

His Arg Asn His Tyr Arg Val Tyr Asn Leu Cys Ser Glu Arg Ala Tyr
            260                 265                 270

Asp Pro Lys His Phe His Asn Arg Val Val Arg Ile Met Ile Asp Asp
        275                 280                 285

His Asn Val Pro Thr Leu His Gln Met Val Val Phe Thr Lys Glu Val
    290                 295                 300

Asn Glu Trp Met Ala Gln Asp Leu Glu Asn Ile Val Ala Ile His Cys
305                 310                 315                 320

Lys Gly Gly Thr Gly Tyr Val Arg Asp Leu Lys Ile Gln Ile Glu Met
                325                 330                 335

Glu Lys Lys Val Val Phe Ser Thr Ile Ser Leu Gly Lys Cys Ser Val
            340                 345                 350

Leu Asp Asn Ile Thr Thr Asp Lys Ile Leu Ile Asp Val Phe Asp Gly
        355                 360                 365

Pro Pro Leu Tyr Asp Asp Val Lys Val Gln Phe Phe Tyr Ser Asn Leu
    370                 375                 380

Pro Thr Tyr Tyr Asp Asn Cys Ser Phe Tyr Phe Trp Leu His Thr Ser
385                 390                 395                 400

Phe Ile Glu Asn Asn Arg Leu Tyr Leu Pro Lys Asn Glu Leu Asp Asn
                405                 410                 415

Leu His Lys Gln Lys Ala Arg Arg Ile Tyr Pro Ser Asp Phe Ala Val
            420                 425                 430

Glu Ile Leu Phe Gly Glu Lys Met Thr Ser Ser Asp Val Val Ala Gly
        435                 440                 445

Ser Asp
    450
```

<210> SEQ ID NO 15
<211> LENGTH: 21
<212> TYPE: DNA
<213> ORGANISM: Artificial sequence
<220> FEATURE:
<223> OTHER INFORMATION: Target sequence -continued

<400> SEQUENCE: 15
tcggtacttg ataacattac a 21

<210> SEQ ID NO 16
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 16
gguacuugau aacauuacat t 21

<210> SEQ ID NO 17
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 17
uguaauguua ucaaguaccg a 21

<210> SEQ ID NO 18
<211> LENGTH: 21
<212> TYPE: DNA
<213> ORGANISM: Artificial sequence
<220> FEATURE:
<223> OTHER INFORMATION: Target sequence

<400> SEQUENCE: 18
cagacttgtg ttattctagc a 21

<210> SEQ ID NO 19
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 19
gacuuguguu auucuagcat t 21

<210> SEQ ID NO 20
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 20

-continued ugcuagaaua acacaaguct g 21

<210> SEQ ID NO 21
<211> LENGTH: 21
<212> TYPE: DNA
<213> ORGANISM: Artificial sequence
<220> FEATURE:
<223> OTHER INFORMATION: Target sequence

<400> SEQUENCE: 21
ctgaaatatg ttcaactgca a 21

<210> SEQ ID NO 22
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 22
gaaauauguu caacugcaat t 21

<210> SEQ ID NO 23
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 23
uugcaguuga acauauuuca g 21

<210> SEQ ID NO 24
<211> LENGTH: 21
<212> TYPE: DNA
<213> ORGANISM: Artificial sequence
<220> FEATURE:
<223> OTHER INFORMATION: Target sequence

<400> SEQUENCE: 24
cagattggca accaagacta a 21

<210> SEQ ID NO 25
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 25
gauuggcaac caagacuaat t 21

<210> SEQ ID NO 26
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 26
uuagucuugg uugccaauct g 21

<210> SEQ ID NO 27
<211> LENGTH: 21
<212> TYPE: DNA
<213> ORGANISM: Artificial sequence
<220> FEATURE:
<223> OTHER INFORMATION: Target sequence

<400> SEQUENCE: 27
aaccctgcca catgttcata t 21

<210> SEQ ID NO 28
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 28
cccugccaca uguucauaut t 21

<210> SEQ ID NO 29
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 29
auaugaacau guggcagggt t 21

<210> SEQ ID NO 30
<211> LENGTH: 21
<212> TYPE: DNA
<213> ORGANISM: Artificial sequence
<220> FEATURE:
<223> OTHER INFORMATION: Target sequence

<400> SEQUENCE: 30
aatgacagtc cacagacaag t 21

<210> SEQ ID NO 31
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases -continued

<400> SEQUENCE: 31
ugacagucca cagacaagut t 21

<210> SEQ ID NO 32
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 32
acuugucugu ggacugucat t 21

<210> SEQ ID NO 33
<211> LENGTH: 21
<212> TYPE: DNA
<213> ORGANISM: Artificial sequence
<220> FEATURE:
<223> OTHER INFORMATION: Target sequence

<400> SEQUENCE: 33
aagctgataa gaaggcgggt t 21

<210> SEQ ID NO 34
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 34
gcugauaaga aggcggguut t 21

<210> SEQ ID NO 35
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 35
aacccgccuu cuuaucagct t 21

<210> SEQ ID NO 36
<211> LENGTH: 21
<212> TYPE: DNA
<213> ORGANISM: Artificial sequence
<220> FEATURE:
<223> OTHER INFORMATION: Oligonucleotide

<400> SEQUENCE: 36
tggatgtcac tctcatcctt g 21

<210> SEQ ID NO 37
<211> LENGTH: 21

<212> TYPE: DNA
<213> ORGANISM: Artificial sequence
<220> FEATURE:
<223> OTHER INFORMATION: Oligonucleotide

<400> SEQUENCE: 37
ccatagttcc tgttctatct g 21

<210> SEQ ID NO 38
<211> LENGTH: 21
<212> TYPE: DNA
<213> ORGANISM: Artificial sequence
<220> FEATURE:
<223> OTHER INFORMATION: Oligonucleotide

<400> SEQUENCE: 38
gagtctacaa tctatgcagt g 21

<210> SEQ ID NO 39
<211> LENGTH: 21
<212> TYPE: DNA
<213> ORGANISM: Artificial sequence
<220> FEATURE:
<223> OTHER INFORMATION: Oligonucleotide

<400> SEQUENCE: 39
cgatgctctt agctgagtgt c 21

<210> SEQ ID NO 40
<211> LENGTH: 21
<212> TYPE: DNA
<213> ORGANISM: Artificial sequence
<220> FEATURE:
<223> OTHER INFORMATION: Oligonucleotide

<400> SEQUENCE: 40
taaccagaca aatcgctcca c 21

<210> SEQ ID NO 41
<211> LENGTH: 46
<212> TYPE: DNA
<213> ORGANISM: Artificial sequence
<220> FEATURE:
<223> OTHER INFORMATION: Oligonucleotide

<400> SEQUENCE: 41
gagagaaagc ttccaccatg aatgaaagtc ctgatccgac tgacct 46

<210> SEQ ID NO 42
<211> LENGTH: 44
<212> TYPE: DNA
<213> ORGANISM: Artificial sequence
<220> FEATURE:
<223> OTHER INFORMATION: Oligonucleotide

<400> SEQUENCE: 42
gagagaaagc ttgatcggat ccagctacaa catcactgga agtc 44

<210> SEQ ID NO 43
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)

-continued

<223> OTHER INFORMATION: ribonucleotide bases

<400> SEQUENCE: 43
uaacuguaua aucgacuagt t 21

<210> SEQ ID NO 44
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 44
cuagucgauu auacaguuag a 21

<210> SEQ ID NO 45
<211> LENGTH: 21
<212> TYPE: DNA
<213> ORGANISM: Artificial sequence
<220> FEATURE:
<223> OTHER INFORMATION: Oligonucleotide

<400> SEQUENCE: 45
cagctgacta aacagaagca g 21

<210> SEQ ID NO 46
<211> LENGTH: 22
<212> TYPE: DNA
<213> ORGANISM: Artificial sequence
<220> FEATURE:
<223> OTHER INFORMATION: Oligonucleotide

<400> SEQUENCE: 46
gagttgaatg cagtcatcac ag 22

<210> SEQ ID NO 47
<211> LENGTH: 1912
<212> TYPE: DNA
<213> ORGANISM: Homo sapiens

<400> SEQUENCE: 47
tttttttctt tccctctagt gggcggggca gaggagttag ccaagatgtg actttgaaac 60
cctcagcgtc tcagtgccct tttgttctaa acaaagaatt ttgtaattgg ttctaccaaa 120
gaaggatata atgaagtcac tatgggaaaa gatggggagg agagttgtag gattctacat 180
taattctctt gtgcccttag cccactactt cagaatttcc tgaagaaagc aagcctgaat 240
tggtttttta aattgcttta aaaatttttt ttaactgggt taatgcttgc tgaattggaa 300
gtgaatgtcc attcctttgc ctcttttgca gatatacact tcagataact acaccgagga 360
aatgggctca ggggactatg actccatgaa ggaaccctgt ttccgtgaag aaaatgctaa 420
tttcaataaa atcttcctgc ccaccatcta ctccatcatc ttcttaactg gcattgtggg 480
caatggattg gtcatcctgg tcatgggtta ccagaagaaa ctgagaagca tgacggacaa 540
gtacaggctg cacctgtcag tggccgacct cctctttgtc atcacgcttc ccttctgggc 600
agttgatgcc gtggcaaact ggtactttgg gaacttccta tgcaaggcag tccatgtcat 660
ctacacagtc aacctctaca gcagtgtcct catcctggcc ttcatcagtc tggaccgcta 720
cctggccatc gtccacgcca ccaacagtca gaggccaagg aagctgttgg ctgaaaaggt 780
ggtctatgtt ggcgtctgga tccctgccct cctgctgact attcccgact tcatctttgc 840
caacgtcagt gaggcagatg acagatatat ctgtgaccgc ttctacccca atgacttgtg 900
ggtggttgtg ttccagtttc agcacatcat ggttggcctt atcctgcctg gtattgtcat 960
cctgtcctgc tattgcatta tcatctccaa gctgtcacac tccaagggcc accagaagcg 1020
caaggccctc aagaccacag tcatcctcat cctggctttc ttcgcctgtt ggctgcctta 1080
ctacattggg atcagcatcg actccttcat cctcctggaa atcatcaagc aagggtgtga 1140
gtttgagaac actgtgcaca agtggatttc catcaccgag gccctagctt tcttccactg 1200
ttgtctgaac ccccatcctct atgctttcct tggagccaaa tttaaaacct ctgcccagca 1260
cgcactcacc tctgtgagca gagggtccag cctcaagatc ctctccaaag gaaagcgagg 1320
tggacattca tctgtttcca ctgagtctga gtcttcaagt tttcactcca gctaacacag 1380
atgtaaaaga cttttttta tacgataaat aactttttt taagttacac atttttcaga 1440
tataaaagac tgaccaatat tgtacagttt ttattgcttg ttggattttt gtcttgtgtt 1500
tctttagttt ttgtgaagtt taattgactt atttatataa attttttttg tttcatattg 1560
atgtgtgtct aggcaggacc tgtggccaag ttcttagttg ctgtatgtct cgtggtagga 1620
ctgtagaaaa gggaactgaa cattccagag cgtgtagtga atcacgtaaa gctagaaatg 1680
atccccagct gtttatgcat agataatctc tccattcccg tggaacgttt ttcctgttct 1740
taagacgtga ttttgctgta gaagatggca cttataacca aagcccaaag tggtatagaa 1800
atgctggttt ttcagttttc aggagtgggt tgatttcagc acctacagtg tacagtcttg 1860
tattaagttg ttaataaaag tacatgttaa acttaaaaaa aaaaaaaaaa aa 1912

<210> SEQ ID NO 48
<211> LENGTH: 1691
<212> TYPE: DNA
<213> ORGANISM: Homo sapiens

<400> SEQUENCE: 48
aacttcagtt tgttggctgc ggcagcaggt agcaaagtga cgccgagggc ctgagtgctc 60
cagtagccac cgcatctgga gaaccagcgg ttaccatgga ggggatcagt atatacactt 120
cagataacta caccgaggaa atgggctcag gggactatga ctccatgaag gaaccctgtt 180
tccgtgaaga aaatgctaat ttcaataaaa tcttcctgcc caccatctac tccatcatct 240
tcttaactgg cattgtgggc aatggattgg tcatcctggt catgggttac cagaagaaac 300
tgagaagcat gacggacaag tacaggctgc acctgtcagt ggccgacctc ctctttgtca 360
tcacgcttcc cttctgggca gttgatgccg tggcaaactg gtactttggg aacttcctat 420
gcaaggcagt ccatgtcatc tacacagtca acctctacag cagtgtcctc atcctggcct 480
tcatcagtct ggaccgctac ctggccatcg tccacgccac caacagtcag aggccaagga 540
agctgttggc tgaaaaggtg gtctatgttg gcgtctggat ccctgccctc ctgctgacta 600
ttcccgactt catctttgcc aacgtcagtg aggcagatga cagatatatc tgtgaccgct 660
tctaccccaa tgacttgtgg gtggttgtgt tccagtttca gcacatcatg gttggcctta 720
tcctgcctgg tattgtcatc ctgtcctgct attgcattat catctccaag ctgtcacact 780
ccaagggcca ccagaagcgc aaggccctca agaccacagt catcctcatc ctggctttct 840
tcgcctgttg gctgccttac tacattggga tcagcatcga ctccttcatc ctcctggaaa 900
tcatcaagca agggtgtgag tttgagaaca ctgtgcacaa gtggatttcc atcaccgagg 960

-continued

```
ccctagcttt cttccactgt tgtctgaacc ccatcctcta tgctttcctt ggagccaaat   1020

ttaaaacctc tgcccagcac gcactcacct ctgtgagcag agggtccagc ctcaagatcc   1080

tctccaaagg aaagcgaggt ggacattcat ctgtttccac tgagtctgag tcttcaagtt   1140

ttcactccag ctaacacaga tgtaaaagac ttttttttat acgataaata acttttttt    1200

aagttacaca tttttcagat ataaaagact gaccaatatt gtacagtttt tattgcttgt   1260

tggatttttg tcttgtgttt ctttagtttt tgtgaagttt aattgactta tttatataaa   1320

tttttttgt ttcatattga tgtgtgtcta ggcaggacct gtggccaagt tcttagttgc    1380

tgtatgtctc gtggtaggac tgtagaaaag ggaactgaac attccagagc gtgtagtgaa   1440

tcacgtaaag ctagaaatga tccccagctg tttatgcata gataatctct ccattcccgt   1500

ggaacgtttt tcctgttctt aagacgtgat tttgctgtag aagatggcac ttataaccaa   1560

agcccaaagt ggtatagaaa tgctggtttt tcagttttca ggagtgggtt gatttcagca   1620

cctacagtgt acagtcttgt attaagttgt taataaaagt acatgttaaa cttaaaaaaa   1680

aaaaaaaaaa a                                                        1691


<210> SEQ ID NO 49
<211> LENGTH: 356
<212> TYPE: PRT
<213> ORGANISM: Homo sapiens

<400> SEQUENCE: 49

Met Ser Ile Pro Leu Pro Leu Leu Gln Ile Tyr Thr Ser Asp Asn Tyr
1               5                   10                  15

Thr Glu Glu Met Gly Ser Gly Asp Tyr Asp Ser Met Lys Glu Pro Cys
            20                  25                  30

Phe Arg Glu Glu Asn Ala Asn Phe Asn Lys Ile Phe Leu Pro Thr Ile
        35                  40                  45

Tyr Ser Ile Ile Phe Leu Thr Gly Ile Val Gly Asn Gly Leu Val Ile
    50                  55                  60

Leu Val Met Gly Tyr Gln Lys Lys Leu Arg Ser Met Thr Asp Lys Tyr
65                  70                  75                  80

Arg Leu His Leu Ser Val Ala Asp Leu Leu Phe Val Ile Thr Leu Pro
                85                  90                  95

Phe Trp Ala Val Asp Ala Val Ala Asn Trp Tyr Phe Gly Asn Phe Leu
            100                 105                 110

Cys Lys Ala Val His Val Ile Tyr Thr Val Asn Leu Tyr Ser Ser Val
        115                 120                 125

Leu Ile Leu Ala Phe Ile Ser Leu Asp Arg Tyr Leu Ala Ile Val His
    130                 135                 140

Ala Thr Asn Ser Gln Arg Pro Arg Lys Leu Leu Ala Glu Lys Val Val
145                 150                 155                 160

Tyr Val Gly Val Trp Ile Pro Ala Leu Leu Leu Thr Ile Pro Asp Phe
                165                 170                 175

Ile Phe Ala Asn Val Ser Glu Ala Asp Asp Arg Tyr Ile Cys Asp Arg
            180                 185                 190

Phe Tyr Pro Asn Asp Leu Trp Val Val Val Phe Gln Phe Gln His Ile
        195                 200                 205

Met Val Gly Leu Ile Leu Pro Gly Ile Val Ile Leu Ser Cys Tyr Cys
    210                 215                 220

Ile Ile Ile Ser Lys Leu Ser His Ser Lys Gly His Gln Lys Arg Lys
225                 230                 235                 240
```

```
Ala Leu Lys Thr Thr Val Ile Leu Ile Leu Ala Phe Phe Ala Cys Trp
                245                 250                 255

Leu Pro Tyr Tyr Ile Gly Ile Ser Ile Asp Ser Phe Ile Leu Leu Glu
            260                 265                 270

Ile Ile Lys Gln Gly Cys Glu Phe Glu Asn Thr Val His Lys Trp Ile
        275                 280                 285

Ser Ile Thr Glu Ala Leu Ala Phe Phe His Cys Cys Leu Asn Pro Ile
    290                 295                 300

Leu Tyr Ala Phe Leu Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
                325                 330                 335

Lys Arg Gly Gly His Ser Ser Val Ser Thr Glu Ser Glu Ser Ser Ser
            340                 345                 350

Phe His Ser Ser
        355


<210> SEQ ID NO 50
<211> LENGTH: 352
<212> TYPE: PRT
<213> ORGANISM: Homo sapiens

<400> SEQUENCE: 50

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255
```

-continued

```
Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
            340                 345                 350


<210> SEQ ID NO 51
<211> LENGTH: 21
<212> TYPE: DNA
<213> ORGANISM: Artificial sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: ribonucleotide bases

<400> SEQUENCE: 51

ggcguauaca ggaacaauat t                                                21


<210> SEQ ID NO 52
<211> LENGTH: 21
<212> TYPE: DNA
<213> ORGANISM: Artificial sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: ribonucleotide bases

<400> SEQUENCE: 52

uauuguuccu guauacgcct t                                                21
```

COMPOSITIONS AND METHODS FOR THERAPY AND DIAGNOSIS OF CANCER AND CANCER METASTASIS

RELATED APPLICATIONS

This application is a Continuation Application of U.S. patent application Ser. No. 12/420,612, filed Apr. 8, 2009, which is a Continuation Application of International Application Number PCT/EP2007/008777, filed Oct. 9, 2007 and claiming priority benefit of European Patent Application Number 06 021 434.3, filed on Oct. 12, 2006. The contents of each of the preceding are incorporated herein by reference in their entireties.

FEDERALLY SPONSORED RESEARCH OR DEVELOPMENT

[Not Applicable]

BACKGROUND OF THE INVENTION

Despite interdisciplinary approaches and exhaustive use of classical therapeutic procedures, cancers are still among the leading causes of death.

In particular, metastasis is one of the most critical factors responsible for the failure of cancer treatment. Although protein expression profiling, gene array analysis and determination of critical factors in tumor tissue have improved the prognostic classification of tumors, it is still difficult to predict the risk of metastasis analyzing the resected primary tumor. After complete tumor resection survival usually depends on occurrence of metastasis. Presently, it is difficult if not impossible to predict, whether a primary tumor has metastasized or not.

Tumor cells biologically differ substantially from their nonmalignant cells of origin. These differences are due to genetic alterations acquired during tumor development and result, inter alia, also in the formation of qualitatively or quantitatively altered molecular structures in the cancer cells. Tumor-associated structures of this kind are, in particular, genetic products the expression of which is induced or enhanced during the course of malignant transformation.

The factors regulating acquisition of the metastatic phenotype are mostly undefined. It is known that some histopathological parameters are associated with tumor-free survival, for instance tumor stage and histological grade. However, it is not yet possible to predict the risk of metastasis by quantification of critical factors in tumor tissue.

It was the object of the present invention to provide compositions and methods for a diagnosis and therapy of cancer, in particular cancer metastasis. In particular, it was the object of the present invention to provide compositions and methods for a diagnosis of metastatic behaviour of cancer.

BRIEF SUMMARY OF THE INVENTION

These objects are achieved by the subject matter of the claims.

The studies presented herein demonstrate that cancers expressing both, TPTE and CXCR4, exhibit a nearly 30 fold increased risk for metastasis, in particular distant metastasis, as compared to tumors lacking at least one of these molecules. A combination of these markers is therefore useful for evaluation of the clinical prognosis of cancer patients and for targeted therapeutical approaches.

Accordingly, the present invention relates to methods which make possible to assess and/or prognose a cancer disease, the metastatic behaviour of a cancer disease and/or the occurrence of a relapse of cancer. In particular, the methods of the invention make possible to assess and/or prognose the occurrence of cancer metastasis, in particular distant metastasis. Preferably, the methods of the invention allow to discriminate malign from benign conditions.

In particular embodiments, the methods of the invention make possible to assess and/or prognose the success of a cancer therapy which has been administered or will be administered. In particular, the methods of the invention make possible to assess and/or prognose the occurrence of a relapse of cancer following cancer therapy, e.g., by surgery, chemotherapy and/or radiation therapy.

In one aspect the invention relates to a method for diagnosing, monitoring, i.e. determining the regression, progression, course and/or onset of, and/or prognosing cancer, the metastatic behaviour of cancer and/or the presence of a relapse of cancer in a patient, which method comprises quantitatively and/or qualitatively determining the level of expression of TPTE in a biological sample isolated from said patient and quantitatively and/or qualitatively determining the level of expression of CXCR4 in a biological sample isolated from said patient. In a particular preferred embodiment, the invention in this aspect relates to a method of diagnosing whether a patient has cancer metastasis, in particular distant metastasis.

In particular embodiments of the method of the invention, the level of expression of TPTE and the level of expression of CXCR4 are determined in the same sample either concurrently or consecutively. In further embodiments of the method of the invention, the level of expression of TPTE and the level of expression of CXCR4 are determined in different samples wherein said different samples may be the same kind of sample, e.g. both may be a blood sample, taken from the patient at the same or different points in time and from the same or different regions of the body, or may be different kinds of samples, e.g. one is a blood sample and the other is an urine sample.

Preferably a level of expression of TPTE and a level of expression of CXCR4 which is increased compared to the level of expression in a subject without cancer, without a risk for cancer, without metastasis of cancer, without a risk for metastasis of cancer, without a relapse of cancer, and/or without a risk for a relapse of cancer is indicative for cancer or for a potential for cancer, for a metastatic behaviour of cancer or for a potential for a metastatic behaviour of cancer and/or for a relapse of cancer or for a potential for a relapse of cancer.

Preferably, the quantitative and/or qualitative determination of the level of expression of TPTE comprises (i) detecting or determining the amount of a nucleic acid which is selected from the group consisting of (a) a nucleic acid which comprises a nucleic acid sequence selected from the group consisting of SEQ ID NOs: 1, 2, 3, 4, 5, 6, and 7, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c), and/or (ii) detecting or determining the amount of a protein or peptide encoded by the nucleic acid under (i) or of a part or derivative thereof, and/or (iii) detecting or determining the amount of an antibody specific for the protein or peptide or for the part or derivative under (ii), and/or (iv) detecting or determining the amount of a T lymphocyte specific for the protein or peptide or for the part or derivative under (ii), optionally in a complex with a MHC molecule, in a biological sample isolated from a patient. Preferably, the nucleic acid under (i) in said quantitative and/or qualitative determination of the level of expression of TPTE comprises a nucleic acid sequence encoding a protein or peptide comprising an amino acid sequence selected from the group consisting of SEQ ID NOs: 8, 9, 10, 11, 12, 13, and 14, a part or derivative thereof and/or the protein or peptide under (ii) in said quantitative and/or qualitative determination of the level of expression of TPTE comprises an amino acid sequence selected from the group consisting of SEQ ID NOs: 8, 9, 10, 11, 12, 13, and 14, a part or derivative thereof.

Preferably, the quantitative and/or qualitative determination of the level of expression of CXCR4 comprises (i) detecting or determining the amount of a nucleic acid which is selected from the group consisting of (a) a nucleic acid which comprises a nucleic acid sequence selected from the group consisting of SEQ ID NOs: 47, and 48, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c), and/or (ii) detecting or determining the amount of a protein or peptide encoded by the nucleic acid under (i) or of a part or derivative thereof, and/or (iii) detecting or determining the amount of an antibody specific for the protein or peptide or for the part or derivative under (ii), and/or (iv) detecting or determining the amount of a T lymphocyte specific for the protein or peptide or for the part or derivative under (ii), optionally in a complex with a MHC molecule, in a biological sample isolated from a patient. Preferably, the nucleic acid under (i) in said quantitative and/or qualitative determination of the level of expression of CXCR4 comprises a nucleic acid sequence encoding a protein or peptide comprising an amino acid sequence selected from the group consisting of SEQ ID NOs: 49, and 50, a part or derivative thereof and/or the protein or peptide under (ii) in said quantitative and/or qualitative determination of the level of expression of CXCR4 comprises an amino acid sequence selected from the group consisting of SEQ ID NOs: 49, and 50, a part or derivative thereof.

Means for accomplishing said quantitative and/or qualitative determination of the level of expression are described herein and will be apparent to the skilled person.

According to the invention, detection of a nucleic acid or determining the amount of a nucleic acid may be carried out using a oligo- or polynucleotide probe which hybridizes specifically to said nucleic acid, or may be carried out by selective amplification of said nucleic acid, e.g. by means of PCR amplification. In one embodiment, the probe comprises a sequence of 6-50, in particular 10-30, 15-30 and 20-30, contiguous nucleotides of said nucleic acid and the primers used in said amplification each comprise a sequence of 6-50, in particular 10-30, 15-30 and 20-30, contiguous nucleotides of said nucleic acid.

Preferably, the detection or determination of the amount of said nucleic acid in the method of the invention comprises (i) contacting the biological sample with an agent which binds specifically to the nucleic acid, and (ii) detecting the formation of or determining the amount of a complex between the agent and the nucleic acid. Preferably, the agent which binds specifically to the nucleic acid is an oligonucleotide or polynucleotide, which hybridizes specifically to said nucleic acid.

According to the invention, detection of a protein or peptide or of a part or derivative thereof or determining the amount of a protein or peptide or of a part or derivative thereof may be carried out using an antibody binding specifically to said protein or peptide or part or derivative thereof. In particular embodiments, the protein or peptide or part or derivative thereof which is to be detected or the amount of which is to be determined in the methods of the present invention is present in a complex with an MHC molecule.

Preferably, the detection or determination of the amount of said protein or peptide or said part or derivative thereof in the method of the invention comprises (i) contacting the biological sample with an agent which binds specifically to the protein or peptide or the part or derivative thereof, and (ii) detecting the formation of or determining the amount of a complex between the agent and the protein or peptide or part or derivative thereof. Preferably, the agent which binds specifically to the protein or peptide or the part or derivative thereof is an antibody binding specifically to said protein or peptide or to said part or derivative thereof.

According to the invention, detection of an antibody or determining the amount of an antibody may be carried out using a protein or peptide binding specifically to said antibody.

Preferably, the detection or determination of the amount of said antibody in the method of the invention comprises (i) contacting the biological sample with an agent which binds specifically to the antibody, and (ii) detecting the formation of or determining the amount of a complex between the agent and the antibody. Preferably, the agent which binds specifically to the antibody is a protein or peptide binding specifically to said antibody.

According to the invention, detection of a T lymphocyte or determining the amount of a T lymphocyte may be carried out using a cell presenting a complex between a protein or peptide and an MHC molecule for which the T lymphocyte is specific, wherein the cell is preferably an antigen-presenting cell. Detection of or determining the amount of a T lymphocyte may also be carried out by detecting its proliferation, cytokine production, and/or cytotoxic activity which may be triggered by specific stimulation with a complex between a protein or peptide and an MHC molecule for which the T lymphocyte is specific. Detection of or determining the amount of a T lymphocyte may also be carried out with aid of a recombinant MHC molecule or a complex of two or more MHC molecules loaded with one or more proteins or peptides.

Preferably, the detection or determination of the amount of said T lymphocyte comprises (i) contacting the biological sample with an agent which binds specifically to the T lymphocyte, and (ii) detecting the formation of or determining the amount of a complex between the agent and the T lymphocyte. Preferably, the agent which binds specifically to the T lymphocyte is a cell presenting the complex between the protein or peptide or the part or derivative thereof for which the T lymphocyte is specific and an MHC molecule.

An agent which is used for detection or determining the amount in the methods of the invention such as an oligo- or polynucleotide probe, an antibody, a protein or peptide or a cell is preferably labeled in a detectable manner, in particular by a detectable marker or diagnostic substance such as a radioactive marker, fluorescence marker or an enzymic marker.

In one embodiment, the method of the invention comprises determining the level of expression in a first sample at a first point in time and in a further sample at a second point in time and a comparison of the two samples. Preferably, a level of expression of TPTE and a level of expression of CXCR4 which is increased in a sample compared to a sample taken earlier from a patient indicates that the patient has developed or is about to develop cancer and/or a metastasis of cancer and/or a relapse of cancer. Preferably, a level of expression of TPTE and a level of expression of CXCR4 which is decreased in a sample compared to a sample taken earlier from a patient indicates regression of cancer and/or a metastasis of cancer in said patient and thus, preferably indicates a successful cancer therapy.

In a further embodiment, the biological sample isolated from the patient is compared to a comparable normal biological sample, e.g. a sample isolated from a healthy individual. Preferably, a level of expression of TPTE and a level of expression of CXCR4 which is increased in a patient's sample compared to a sample taken from a healthy individual indicates that the patient has developed or is about to develop cancer and/or a metastasis of cancer and/or a relapse of cancer.

The determination of the level of expression of TPTE may also involve the determination of methylation patterns and/or the degree of methylation with a nucleic acid which is selected from the group consisting of (a) a nucleic acid which comprises a nucleic acid sequence selected from the group consisting of SEQ ID NOs: 1, 2, 3, 4, 5, 6, and 7, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c), and/or with a nucleic acid comprising a nucleic acid sequence encoding a protein or peptide comprising an amino acid sequence selected from the group consisting of SEQ ID NOs: 8, 9, 10, 11, 12, 13, and 14, a part or derivative thereof, preferably within the non-coding region thereof and more preferably within the promoter region thereof.

A degree of methylation which is lower compared to a control, e.g. a subject without cancer, without a risk for cancer, without metastasis of cancer, without a risk for metastasis of cancer, without a relapse of cancer, and/or without a risk for a relapse of cancer, or no methylation preferably is indicative for an increased level of expression of TPTE.

The determination of methylation patterns and/or the degree of methylation can be performed, for example, by using methods on the basis of PCR, with the aid of restriction enzymes or by sequencing. In one preferred embodiment, genomic DNA is selectively amplified following treatment with a bisulfite containing reagent. The oligonucleotides used in such amplification preferably have a sequence binding to the nucleic acid treated with the bisulfite containing reagent and preferably are completely complementary thereto. Preferably the oligonucleotides are adapted to a different degree of methylation of the nucleic acid and bring about amplification products which can be differentiated. A test suitable for this can be as follows: (1) extraction of DNA from tissue samples of patients, for example using paraffin embedded material, (2) treatment of the DNA with bisulfite containing reagents (e.g. as described in Clark S. J. et al., Nucleic Acids Res. 22(15):2990-7, 1994), (3) amplification of DNA by means of PCR and (4) analysis of the amount of sequence specific amplification products (e.g. by means of quantitative PCR, hybridization techniques such as microarray methods).

In particular embodiments of the method of the invention, the patient has cancer, is suspected of having cancer or developing cancer, or has a risk for developing cancer. In further embodiments of the method of the invention, the patient has a cancer metastasis, is suspected of having a cancer metastasis or developing a cancer metastasis, or has a risk for developing a cancer metastasis. In particular embodiments of the method of the invention, the patient has already been subjected to cancer therapy such as by tumor resection, radiation therapy and/or chemotherapy, or it is intended to subject the patient to such therapy.

The method of diagnosing, monitoring, and/or prognosing cancer, the metastatic behaviour of cancer and/or the presence of a relapse of cancer according to the invention preferably allows the prognosis of a worsened course of a disease, whereby among other things planning of a more aggressive therapy is made possible. This prognostic method also allows to delimit still benign alterations, e.g. hyperplasias, from tumor precursors which are already to be appraised as unfavourable and to anticipate therefore a cancer disposition already before an invasive tumor has formed.

In a further aspect, the invention relates to a kit comprising means for quantitatively and/or qualitatively determining the level of expression of TPTE and means for quantitatively and/or qualitatively determining the level of expression of CXCR4 in a biological sample isolated from a patient. Preferably, the kit is useful in the method for diagnosing, monitoring and/or prognosing cancer, the metastatic behaviour of cancer and/or the presence of a relapse of cancer of the invention.

Means for quantitatively and/or qualitatively determining the level of expression of TPTE and CXCR4 are as discussed above.

Preferably, said means for quantitatively and/or qualitatively determining the level of expression of TPTE are selected from the group consisting of (i) means for detecting or determining the amount of a nucleic acid which is selected from the group consisting of (a) a nucleic acid which comprises a nucleic acid sequence selected from the group consisting of SEQ ID NOs: 1, 2, 3, 4, 5, 6, and 7, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c), and/or (ii) means for detecting or determining the amount of a protein or peptide encoded by the nucleic acid under (i) or of a part or derivative thereof, and/or (iii) means for detecting or determining the amount of an antibody specific for the protein or peptide or the part or derivative under (ii), and/or (iv) means for detecting or determining the amount of a T lymphocyte specific for the protein or peptide or the part or derivative under (ii), optionally in a complex with a MHC molecule, in a biological sample isolated from a patient. Preferably, the nucleic acid under (i) in said quantitative and/or qualitative determination of the level of expression of TPTE comprises a nucleic acid sequence encoding a protein or peptide comprising an amino acid sequence selected from the group consisting of SEQ ID NOs: 8, 9, 10, 11, 12, 13, and 14, a part or derivative thereof and/or the protein or peptide under (ii) in said quantitative and/or qualitative determination of the level of expression of TPTE comprises an amino acid sequence selected from the group consisting of SEQ ID NOs: 8, 9, 10, 11, 12, 13, and 14, a part or derivative thereof.

Preferably, said means for quantitatively and/or qualitatively determining the level of expression of CXCR4 are selected from the group consisting of (i) means for detecting or determining the amount of a nucleic acid which is selected from the group consisting of (a) a nucleic acid which comprises a nucleic acid sequence selected from the group consisting of SEQ ID NOs: 47, and 48, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c), and/or (ii) means for detecting or determining the amount of a protein or peptide encoded by the nucleic acid under (i) or of a part or derivative thereof, and/or (iii) means for detecting or determining the amount of an antibody specific for the protein or peptide or the part or derivative under (ii), and/or (iv) means for detecting or determining the amount of a T lymphocyte specific for the protein or peptide or the part or derivative under (ii), optionally in a complex with a MHC molecule, in a biological sample isolated from a patient. Preferably, the nucleic acid under (i) in said quantitative and/or qualitative determination of the level of expression of CXCR4 comprises a nucleic acid sequence encoding a protein or peptide comprising an amino acid sequence selected from the group consisting of SEQ ID NOs: 49, and 50, a part or derivative thereof and/or the protein or peptide under (ii) in said quantitative and/or qualitative determination of the level of expression of CXCR4 comprises an amino acid sequence selected from the group consisting of SEQ ID NOs: 49, and 50, a part or derivative thereof.

Preferably, said means for detecting or determining the amount of said nucleic acid comprise an agent which binds specifically to the nucleic acid. Preferably, the agent which binds specifically to the nucleic acid is an oligonucleotide or polynucleotide, which hybridizes specifically to said nucleic acid.

Preferably, said means for detecting or determining the amount of said protein or peptide or part or derivative thereof comprise an agent which binds specifically to the protein or peptide or the part or derivative thereof. Preferably, the agent which binds specifically to the protein or peptide or the part or derivative thereof is an antibody binding specifically to said protein or peptide or to said part or derivative thereof.

Preferably, said means for detecting or determining the amount of said antibody comprise an agent which binds specifically to the antibody. Preferably, the agent which binds specifically to the antibody is a protein or peptide binding specifically to said antibody.

Preferably, said means for detecting or determining the amount of said T lymphocyte comprise an agent which binds specifically to the T lymphocyte. Preferably, the agent which binds specifically to the T lymphocyte is a cell presenting the complex between the protein or peptide or the part or derivative thereof for which the T lymphocyte is specific and an MHC molecule.

In a further aspect, the invention relates to a pharmaceutical composition comprising (i) an agent which is effective in reducing or inhibiting expression or activity of TPTE and/or which binds to TPTE and has tumor destroying or tumor inhibiting activity, and (ii) an agent which is effective in reducing or inhibiting expression or activity of CXCR4 and/or which binds to CXCR4 and has tumor destroying or tumor inhibiting activity. The terms "activity of TPTE" and "activity of CXCR4" relate to any activity of TPTE or CXCR4 in a cell or an organism such as enzymatic or regulatory activity, in particular cell migration modulatory activity. Preferably, the agent which binds to TPTE or CXCR4 and has tumor destroying or tumor inhibiting activity is specific for cells expressing or abnormally expressing TPTE or CXCR4, respectively. Preferably, such agent comprises a therapeutic substance.

In certain embodiments of the pharmaceutical composition of the invention, the agent is an antisense nucleic acid which hybridizes selectively with the nucleic acid coding for TPTE and/or hybridizes selectively with the nucleic acid coding for CXCR4. In further embodiments, the agent is a siRNA preferably comprising a sense RNA strand and an antisense RNA strand, wherein the sense and antisense RNA strands form an RNA duplex, and wherein the sense RNA strand comprises a nucleotide sequence substantially identical to a target sequence of about 19 to about 25 contiguous nucleotides in TPTE mRNA and/or in CXCR4 mRNA. In even further embodiments, the agent is an antibody which binds selectively to TPTE and/or CXCR4. The antisense nucleic acid, siRNA and/or antibody discussed above may be combined in the pharmaceutical composition of the invention.

In even a further aspect, the invention relates to a pharmaceutical composition comprising (I) one or more components selected from the group consisting of (i) TPTE or a part or derivative thereof, (ii) a nucleic acid which codes for TPTE or a part or derivative thereof, (iii) an antibody which binds to TPTE or a part thereof, (iv) an antisense nucleic acid which hybridizes specifically with a nucleic acid coding for TPTE, (v) an siRNA directed against a nucleic acid coding for TPTE, (vi) a host cell which expresses TPTE or a part or derivative thereof, and (vii) isolated complexes between TPTE or a part or derivative thereof and an MHC molecule, and (II) one or more components selected from the group consisting of (i) CXCR4 or a part or derivative thereof, (ii) a nucleic acid which codes for CXCR4 or a part or derivative thereof, (iii) an antibody which binds to CXCR4 or a part or derivative thereof, (iv) an antisense nucleic acid which hybridizes specifically with a nucleic acid coding for CXCR4, (v) an siRNA directed against a nucleic acid coding for CXCR4, (vi) a host cell which expresses CXCR4 or a part or derivative thereof, and (vii) isolated complexes between CXCR4 or a part or derivative thereof and an MHC molecule.

In one embodiment, a nucleic acid coding for TPTE or CXCR4 or a part or derivative thereof is present in the pharmaceutical composition in an expression vector and functionally linked to a promoter.

In a further embodiment, a host cell present in a pharmaceutical composition of the invention secretes TPTE or CXCR4 or the part or derivative thereof, expresses it on the surface and preferably additionally express an MHC molecule which binds to said TPTE or CXCR4 or the part or derivative thereof. In one embodiment, the host cell expresses the MHC molecule endogenously. In a further embodiment, the host cell expresses the MHC molecule and/or TPTE or CXCR4 or the part or derivative thereof in a recombinant manner. The host cell is preferably nonproliferative. In a preferred embodiment, the host cell is an antigen-presenting cell, in particular a dendritic cell, a monocyte or a macrophage.

In a further embodiment, an antibody present in a pharmaceutical composition of the invention is a monoclonal antibody. In further embodiments, the antibody is a chimeric or humanized antibody, a fragment of a natural antibody or a synthetic antibody.

An antisense nucleic acid present in a pharmaceutical composition of the invention may comprise a sequence of 6-50, in particular 10-30, 15-30 and 20-30, contiguous nucleotides of the nucleic acid coding for TPTE or the part or derivative thereof and/or of the nucleic acid coding for CXCR4 or the part or derivative thereof.

In further embodiments, TPTE or CXCR4 or the part or derivative thereof, provided by a pharmaceutical composition of the invention either directly or via expression of a nucleic acid, binds to MHC molecules on the surface of cells, said binding preferably causing a cytolytic response and/or inducing cytokine release.

The antibody contained in the pharmaceutical composition of the invention may be coupled to a therapeutic substance.

In particular embodiments of the siRNA directed against a nucleic acid coding for TPTE contained in the pharmaceutical composition of the invention the target sequence has a nucleic acid sequence selected from the group consisting of nucleotide positions 3-21 of SEQ ID NO: 15, nucleotide positions 3-21 of SEQ ID NO: 18, nucleotide positions 3-21 of SEQ ID NO: 21, nucleotide positions 3-21 of SEQ ID NO: 24, nucleotide positions 3-21 of SEQ ID NO: 27, nucleotide positions 3-21 of SEQ ID NO: 30, and nucleotide positions 3-21 of SEQ ID NO: 33. In further particular embodiments of the siRNA the sense RNA strand has the sequence of SEQ ID NO: 16 and the antisense RNA strand has the sequence of SEQ ID NO: 17, or sense RNA strand has the sequence of SEQ ID NO: 19 and the antisense RNA strand has the sequence of SEQ ID NO: 20, or the sense RNA strand has the sequence of SEQ ID NO: 22 and the antisense RNA strand has the sequence of SEQ ID NO: 23, or the sense RNA strand has the sequence of SEQ ID NO: 25 and the antisense RNA strand has the sequence of SEQ ID NO: 26, or the sense RNA strand has the sequence of SEQ ID NO: 28 and the antisense RNA strand has the sequence of SEQ ID NO: 29, or the sense RNA strand has the sequence of SEQ ID NO: 31 and the antisense RNA strand has the sequence of SEQ ID NO: 32, or the sense RNA strand has the sequence of SEQ ID NO: 34 and the antisense RNA strand has the sequence of SEQ ID NO: 35.

A pharmaceutical composition of the invention may comprise a pharmaceutically compatible carrier and/or an adjuvant.

In a further aspect, the invention relates to a method of treating or preventing cancer, metastasis of cancer or relapse of cancer comprising administering to a patient (I) one or more components selected from the group consisting of (i) TPTE or a part or derivative thereof, (ii) a nucleic acid which codes for TPTE or a part or derivative thereof, (iii) an antibody which binds to TPTE or a part thereof, (iv) an antisense nucleic acid which hybridizes specifically with a nucleic acid coding for TPTE, (v) an siRNA directed against a nucleic acid coding for TPTE, (vi) a host cell which expresses TPTE or a part or derivative thereof, and (vii) isolated complexes between TPTE or a part or derivative thereof and an MHC molecule, and (II) one or more components selected from the group consisting of (i) CXCR4 or a part or derivative thereof, (ii) a nucleic acid which codes for CXCR4 or a part or derivative thereof, (iii) an antibody which binds to CXCR4 or a part or derivative thereof, (iv) an antisense nucleic acid which hybridizes specifically with a nucleic acid coding for CXCR4, (v) an siRNA directed against a nucleic acid coding for CXCR4, (vi) a host cell which expresses CXCR4 or a part or derivative thereof, and (vii) isolated complexes between CXCR4 or a part or derivative thereof and an MHC molecule.

The invention also relates to a method of treating or preventing cancer, metastasis of cancer or relapse of cancer comprising administering the pharmaceutical composition of the invention.

Preferably, the cancer is a lung tumor, a breast tumor, a prostate tumor, a melanoma, a colon tumor, a gastric tumor, a pancreatic tumor, an ENT tumor, a renal cell carcinoma or a cervical carcinoma, a colon carcinoma or a mammary carcinoma.

Preferably, the cancer, metastasis of cancer or relapse of cancer is characterized by expression or abnormal expression of (i) a nucleic acid which is selected from the group consisting of (a) a nucleic acid which comprises a nucleic acid sequence selected from the group consisting of SEQ ID NOs: 1, 2, 3, 4, 5, 6, and 7, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c), and/or (ii) a protein or peptide encoded by the nucleic acid under (i). Preferably the nucleic acid under (i) comprises a nucleic acid sequence encoding a protein or peptide comprising an amino acid sequence selected from the group consisting of SEQ ID NOs: 8, 9, 10, 11, 12, 13, and 14, a part or derivative thereof and/or the protein or peptide under (ii) comprises an amino acid sequence selected from the group consisting of SEQ ID NOs: 8, 9, 10, 11, 12, 13, and 14, a part or derivative thereof.

More preferably, the cancer, metastasis of cancer or relapse of cancer is characterized by further expression or abnormal expression of (i) a nucleic acid which is selected from the group consisting of (a) a nucleic acid which comprises a nucleic acid sequence selected from the group consisting of SEQ ID NOs: 47, and 48, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c), and/or (ii) a protein or peptide encoded by the nucleic acid under (i). Preferably the nucleic acid under (i) comprises a nucleic acid sequence encoding a protein or peptide comprising an amino acid sequence selected from the group consisting of SEQ ID NOs: 49, and 50, a part or derivative thereof and/or the protein or peptide under (ii) comprises an amino acid sequence selected from the group consisting of SEQ ID NOs: 49, and 50, a part or derivative thereof.

In the methods of the invention the pharmaceutical composition is preferably administered in combination with radiation therapy, chemotherapy or surgery, wherein the chemotherapeutic agent is preferably selected from the group consisting of cisplatin, carboplatin, cyclophosphamide, 5-fluorouracil, adriamycin, daunorubicin, and tamoxifen.

Preferably the subject or patient in the methods of the invention is a human being.

a, b, Analysis of TPTE mRNA expression by (a) conventional RT-PCR and (b) quantitative Real-Time RT-PCR in normal human tissues, TPTE positive tumor specimens and cancer cell lines. c, Western blot analysis of protein lysates from normal tissues and cancer cell lines with constitutive TPTE expression. Controls were NIH3T3 cells transfected with TPTE cDNA (+) or a control plasmid (−). d, Immunohistochemical staining of testis and malignant tissues for TPTE. Blocking with the recombinant protein fragment used for immunization (+) as compared to the buffer control (−) confirmed specificity of the polyclonal antiserum pAK2091. e, (left) Induction of TPTE mRNA expression in TPTE negative BT-549 breast cancer cells treated with the methylation inhibitor dAC as shown by real time RT-PCR analysis. (right) Relative amounts of TPTE transcripts in DNA methyltransferase knockout variants of HCT116 cells as compared to wild type cells.

Figure 2:
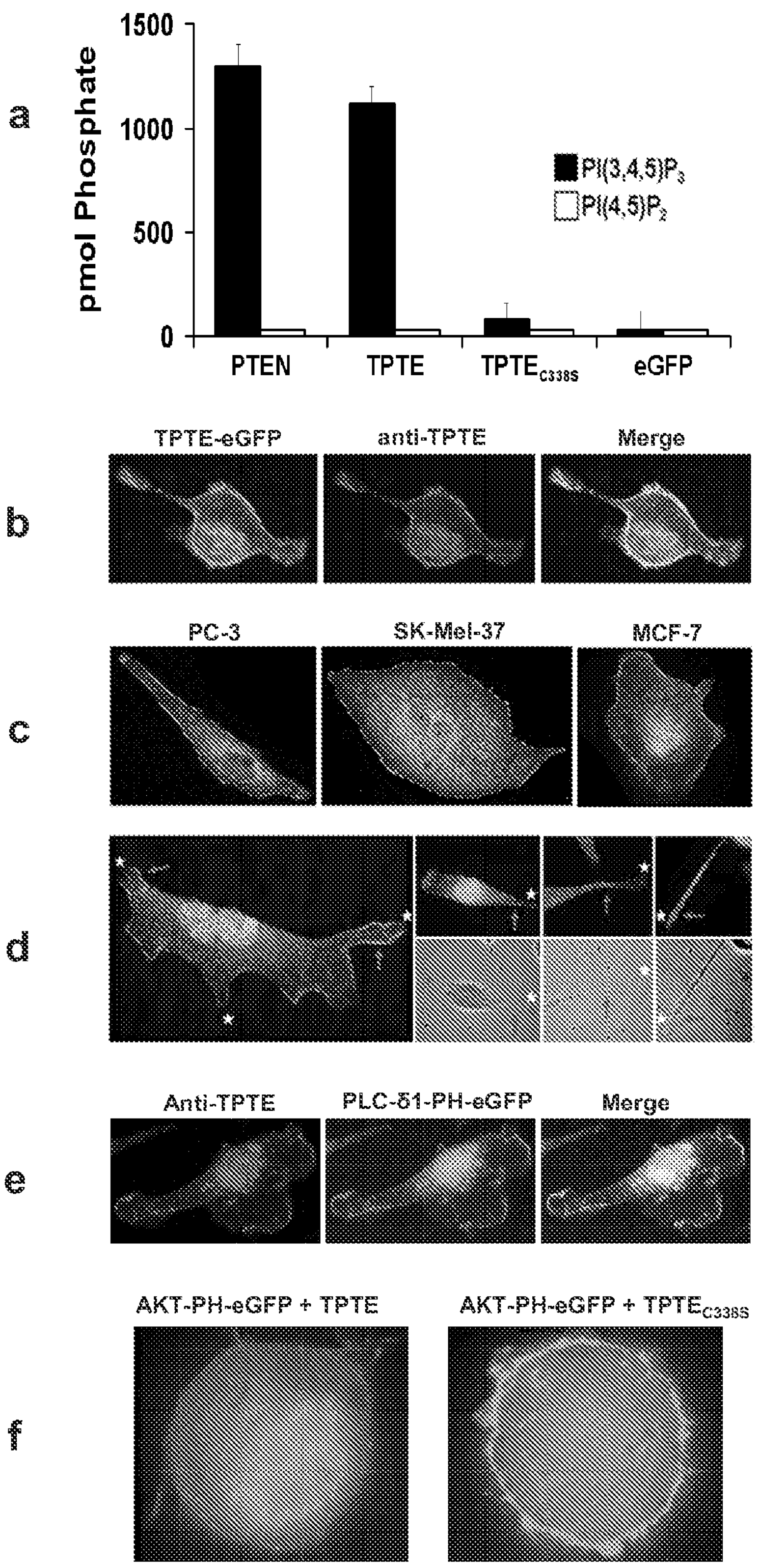

FIG. 2. TPTE is a phosphoinositol 3'-phosphatase localized at the plasmamembrane.

a, In vitro phosphatase assay with recombinant proteins using $PI(3,4,5)P_3$ and $PI(4,5)P_2$ as substrates. b, Colocalization of TPTE-eGFP fluorescence and pAK2091 staining for verification of the specificity of the polyclonal rabbit antiserum. c, Immunofluorescence analysis of cancer cell lines displaying a constitutive expression of TPTE. d, Localization of endogenous TPTE in filo- and pseudopodia of PC-3 prostate cancer cells; arrows, accumulation of TPTE at the lateral margins of cell protrusions; asterisks, tips of protrusions are free of TPTE. e, Colocalization of endogenously expressed TPTE in PC-3 cells with $PIP_2$ visualized by staining of PLC-δ1-PH-eGFP transfected cells with anti-TPTE. f, Transfection of TPTE but not of the catalytically inactive mutant $TPTE_{C338S}$ into NIH3T3-her2 cells reduces constitutive $PIP_3$ signaling and thus leads to cytoplasmic redistribution of AKT-PH-eGFP.

Figure 3:
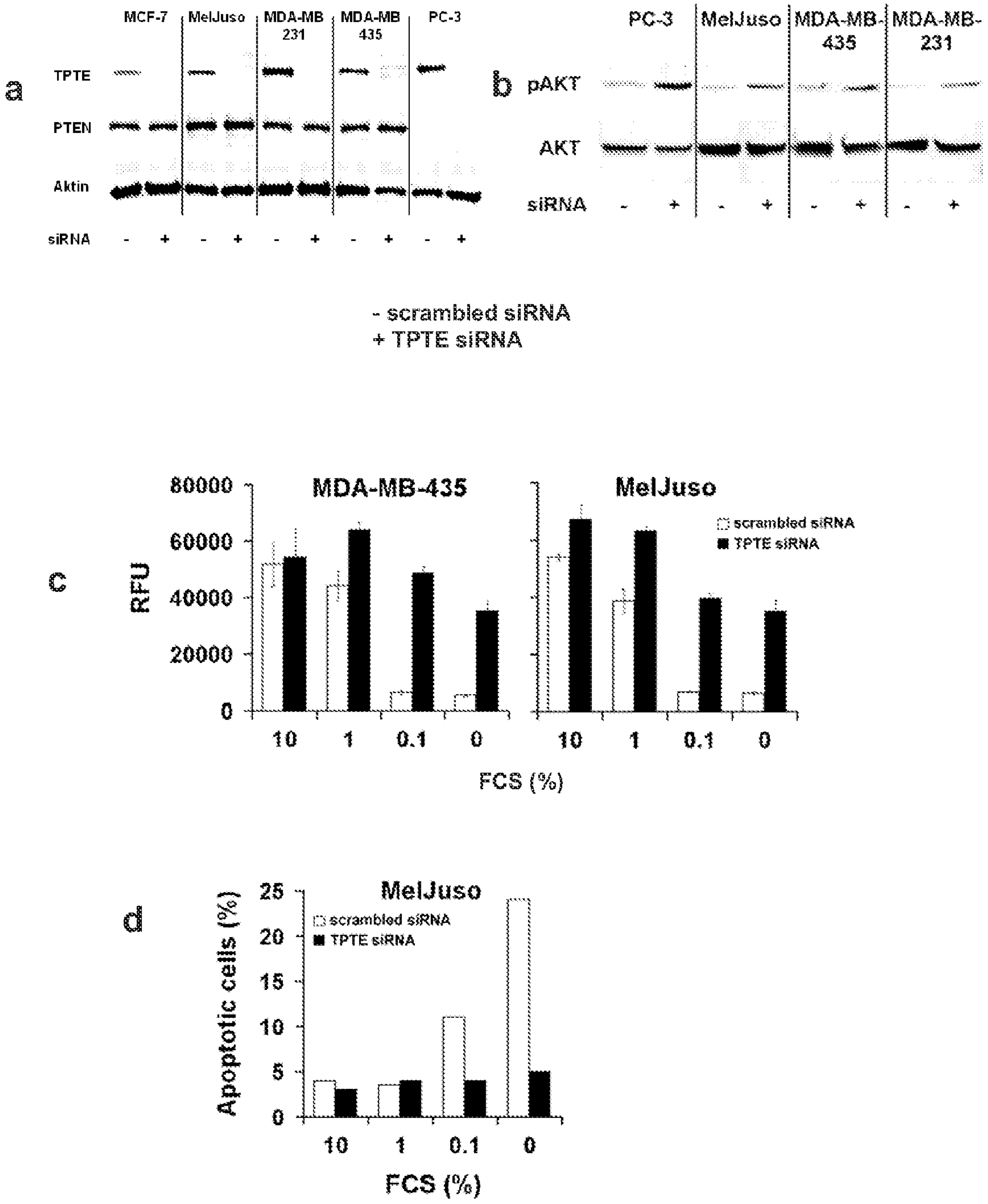

FIG. 3. TPTE establishes a growth-factor dependent phenotype in cancer cells.

The influence of TPTE on AKT phosphorylation, cell proliferation and resistance to apoptosis induced by growth factor deprivation was analyzed in siRNA transfected TPTE positive tumor cell lines (a-d) as well as in transformed cells ectopically expressing TPTE or the catalytically inactive mutant $TPTE_{C338S}$ and eGFP as controls (e-i). a, Western blot analysis of siRNA transfected cells. TPTE siRNA specifically suppresses the respective phosphatase. Note that PTEN protein levels are not affected by TPTE siRNA. b, suppression of TPTE by TPTE siRNA (+) but not scrambled siRNA duplexes (−) leads to an increase of cellular phospho-AKT levels. c, d, As documented by proliferation rates (c) and apoptotic fraction (d) of MDA-MB-435 breast cancer and MelJuso melanoma cells cultured for 48 h in medium supplemented with various concentrations of serum, TPTE downregulation uncouples cell proliferation and survival from dependency on external growth factors. Similar data were obtained for MDA-MB-231 and PC-3 cells. RFU stands for relative fluorescence unit. e, Western blot analysis of HER-2/neu expression and AKT phosphorylation in wild type and HER2/neu transformed NIH3T3 fibroblasts (NIH3T3-her2). f, TPTE but not a catalytically inactive variant reduces cellular $PIP_3$ levels in Her2/neu transformed fibroblasts. Cellular $PIP_3$ levels were quantified from lysates of serum deprived cells as described in example 1 using a $PIP_3$ specific ELISA. g, AKT phosphorylation in NIH3T3-her2 cells transfected with TPTE-eGFP and controls. h, Stable expression of catalytically active TPTE-eGFP abrogates autonomous growth of NIH3T3-her2 cells as determined by flowcytometric cell cycle analysis. i, tumor growth kinetics after s.c. inoculation of stably transfected NIH3T3-her2 cells in immunocompromised mice.

Figure 4:
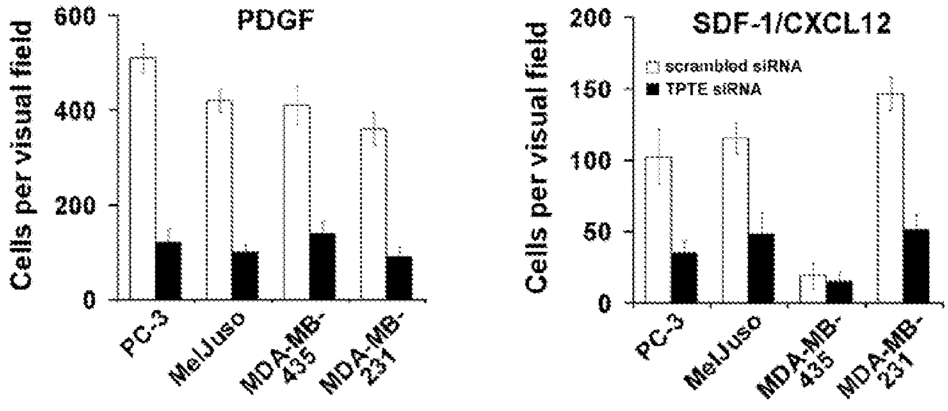
Figure 4:
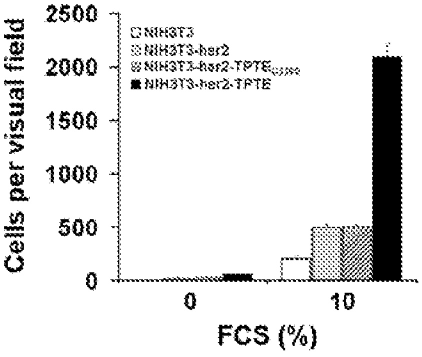
Figure 4:
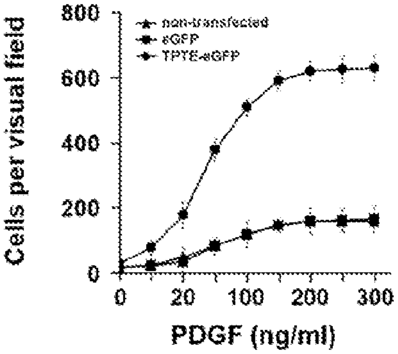
Figure 4:

FIG. 4. TPTE promotes cell chemotaxis.

a, Transwell migration assay using PDGF-BB (200 ng/ml) and SDF-1α/CXCL12* (200 ng/ml) as chemoattractants 48 h after transfection of cells with siRNA oligos; (*MDA-MB-435 cells do not express CXCR4, the receptor for CXCL12). b, c Chemotaxis of NIH-3T3-her2 transfectants analyzed in transwell migration assay using FCS or various concentrations of PDGF-BB as chemoattractants. d, Morphological characteristics of serum-free cultured NIH3T3-her2 cells stably transfected with either TPTE-eGFP or control vectors. e, f, g impact of single and combined siRNA mediated knock down of PTEN and TPTE on tumor cell chemotaxis, cellular $PIP_3$ levels and pAKT levels (** note that PC-3 cells do not express PTEN).

Figure 5:
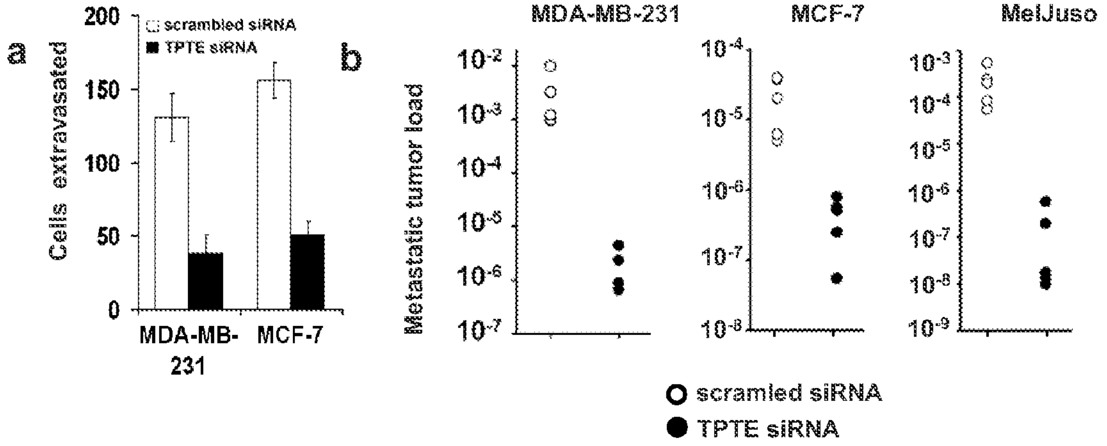
Figure 5:
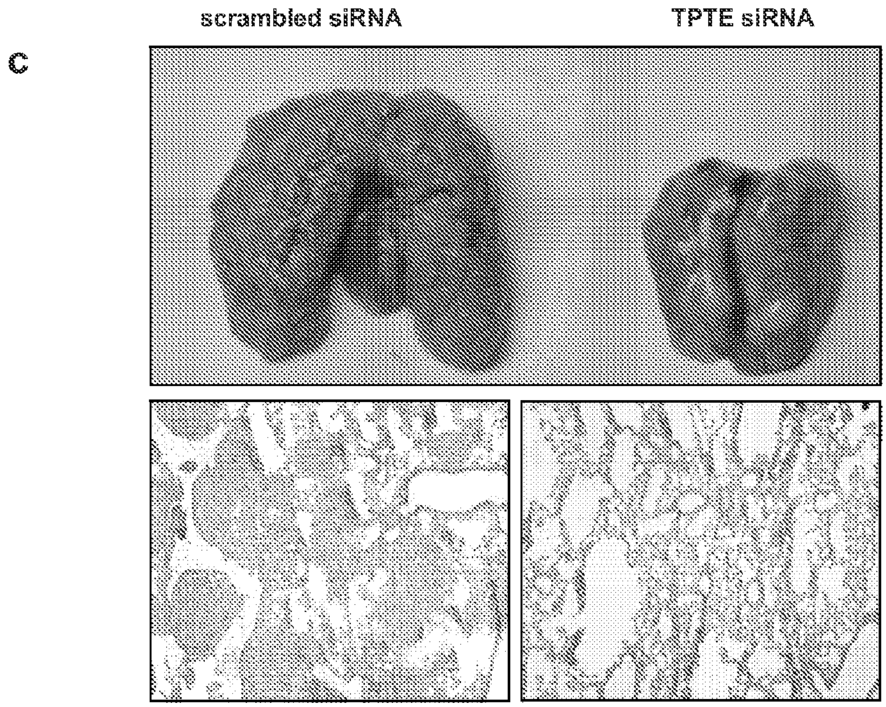

FIG. 5. TPTE is essential for metastatic spread of tumor cells.

a, In vivo tumor cell extravasation assay using breast cancer cells transfected with siRNA and labeled with a fluorophore. Cells extravasated into the lungs were documented by fluorescence microscopy and counted 6 h after injection. b, Experimental metastasis assay based on injection of TPTE siRNA or control siRNA treated breast cancer and melanoma cells into the tail vein of NOD/SCID (MDA-MB-231) or nude (MCF-7, MelJuso) mice. Metastatic tumor load was determined five weeks after inoculation by quantitative PCR using oligonucleotides specific for human microsatellite DNA. c, Representative lungs and HE-stained lung tissue sections obtained by an independent experiment from nude mice four weeks after inoculation with siRNA transfected MDA-MB-231 cells. Note that experiments with PTEN siRNA transfected MDA-MB-231 cells resulted in similar reduction of metastatic tumor load. d, Venn diagram for illustration of metastasis rates in groups of patients. Patients were grouped according to the status of TPTE and CXCR4 expression in the primary tumor samples. The statistics illustrate the numbers of cases with metastasis versus the total number of patients in the respective group.

DETAILED DESCRIPTION OF THE INVENTION

The expression "determining the level of expression" with respect to TPTE or CXCR4 according to the invention relates to the determination of the absence or presence and/or the absolute and/or relative quantification of a gene product of the TPTE gene or CXCR4 gene (nucleic acid and protein/peptide). The expression "determining the level of expression" according to the invention also includes situations wherein no gene product is detected or the amount of said gene product is below the detection limit.

Generally all methods suitable to detect and analyse nucleic acids, proteins and/or peptides can be used for determining the level of expression in the methods of the invention. PCR, gene chip/microarray systems, Northern blot, RNAse protection assays (RDA) can, for example, be used for detecting and analyzing nucleic acids. Suitable immunologic methods for detecting and analyzing proteins and/or peptides among others are enzyme linked immuno assays (ELISA), sandwich, direct, indirect, or competitive ELISA assays, enzyme-linked immunospot assays (ELISPOT), radio immuno assays (RIA), flow cytometry assays (FACS=fluorescence activated cell sorting), immunohistochemistry, Western blot, fluorescence resonance energy transfer (FRET) assays, protein-chip assays using for example antibodies, antibody fragments, receptors, ligands, or other binding agents specific for peptides or proteins.

According to the invention, the term "binding" preferably relates to a specific binding. "Specific binding" means that an agent such as an antibody binds stronger to a target such as an epitope for which it is specific compared to the binding to another target. An agent binds stronger to a first target compared to a second target if it binds to the first target with a dissociation constant ($K_D$) which is lower than the dissociation constant for the second target. Preferably the dissociation constant ($K_D$) for the target to which the agent binds specifically is more than 10-fold, preferably more than 20-fold, more preferably more than 50-fold, even more preferably more than 100-fold, 200-fold, 500-fold or 1000-fold lower than the dissociation constant ($K_D$) for the target to which the agent does not bind specifically.

According to the invention, a "reference" such as a reference sample or reference organism may be used to correlate and compare the results obtained in the methods of the invention from a test sample or test organism, i.e. a patient. Typically the reference organism is a healthy organism, in particular an organism which does not suffer from cancer, metastasis of cancer and/or relapse of cancer.

A "reference value" can be determined from a reference empirically by measuring a sufficiently large number of references. Preferably the reference value is determined by measuring at least 2, preferably at least 3, preferably at least 5, preferably at least 8, preferably at least 12, preferably at least 20, preferably at least 30, preferably at least 50, or preferably at least 100 references.

The term “TPTE” relates to “transmembrane phosphatase with tensin homology” and includes any variants, in particular splice variant, conformations, isoforms and species homologs of TPTE which are naturally expressed by cells or are expressed by cells transfected with the TPTE gene. The expression “determining the level of expression of TPTE” relates to a determination of the level of a nucleic acid of TPTE, such as mRNA, and/or a determination of the level of TPTE protein.

Preferably, a “nucleic acid of TPTE”, a “nucleic acid encoding TPTE”, a “nucleic acid coding for TPTE” or “TPTE gene” relates to a nucleic acid selected from the group consisting of (a) a nucleic acid which comprises a nucleic acid sequence selected from the group consisting of SEQ ID NOs: 1, 2, 3, 4, 5, 6, and 7, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). The terms may also include mRNA coding for TPTE. Preferably, “TPTE” protein or simply “TPTE” comprises an amino acid sequence encoded by the afore mentioned nucleic acid, preferably an amino acid sequence selected from the group consisting of SEQ ID NOs: 8, 9, 10, 11, 12, 13, and 14, a part or derivative thereof. One skilled in the art would understand that the cDNA sequence of TPTE as described above would be equivalent to TPTE mRNA, and can be used for the same purpose herein; i.e., the generation of siRNA for inhibiting expression of TPTE.

The term “TPTE” also includes posttranslationally modified variants, isoforms and species homologs of human TPTE which are naturally expressed by cells or are expressed by cells transfected with the TPTE gene.

The term “CXCR4” relates to “chemokine (C-X-C motif) receptor 4” and includes any variants, in particular splice variant, conformations, isoforms and species homologs of CXCR4 which are naturally expressed by cells or are expressed by cells transfected with the CXCR4 gene. The expression “determining the level of expression of CXCR4” relates to a determination of the level of a nucleic acid of CXCR4, such as mRNA, and/or a determination of the level of CXCR4 protein.

Preferably, a “nucleic acid of CXCR4”, a “nucleic acid encoding CXCR4”, a “nucleic acid coding for CXCR4” or “CXCR4 gene” relates to a nucleic acid selected from the group consisting of (a) a nucleic acid which comprises a nucleic acid sequence selected from the group consisting of SEQ ID NOs: 47, and 48, a part or derivative thereof, (b) a nucleic acid which hybridizes with the nucleic acid of (a) under stringent conditions, (c) a nucleic acid which is degenerate with respect to the nucleic acid of (a) or (b), and (d) a nucleic acid which is complementary to the nucleic acid of (a), (b) or (c). The terms may also include mRNA coding for CXCR4. Preferably, “CXCR4” protein or simply “CXCR4” comprises an amino acid sequence encoded by the afore mentioned nucleic acid, preferably an amino acid sequence selected from the group consisting of SEQ ID NOs: 49, and 50, a part or derivative thereof. One skilled in the art would understand that the cDNA sequence of CXCR4 as described above would be equivalent to CXCR4 mRNA, and can be used for the same purpose herein; i.e., the generation of siRNA for inhibiting expression of CXCR4.

The term “CXCR4” also includes posttranslationally modified variants, isoforms and species homologs of human CXCR4 which are naturally expressed by cells or are expressed by cells transfected with the CXCR4 gene.

According to the invention, a nucleic acid is preferably deoxyribonucleic acid (DNA) or ribonucleic acid (RNA). Nucleic acids comprise according to the invention genomic DNA, cDNA, mRNA, recombinantly produced and chemically synthesized molecules. According to the invention, a nucleic acid may be present as a single-stranded or double-stranded and linear or covalently circularly closed molecule.

A degenerate nucleic acid according to the invention is a nucleic acid that differs from a reference nucleic acid in codon sequence due to the degeneracy of the genetic code.

The term “nucleic acid” according to the invention also includes “derivatives” of a nucleic acid. “Derivative” of a nucleic acid means according to the invention that single or multiple, such as at least 2, at least 4, or at least 6 and preferably up to 3, up to 4, up to 5, up to 6, up to 10, up to 15, or up to 20 nucleotide substitutions, deletions and/or additions are present in said nucleic acid. Furthermore, the term “derivative” also comprises chemical derivatization of a nucleic acid on a nucleotide base, on the sugar or on the phosphate. The term “derivative” also comprises nucleic acids which contain nucleotides and nucleotide analogs not occurring naturally.

The nucleic acids described according to the invention have preferably been isolated. The term “isolated nucleic acid” means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

As used herein, the term “RNA” means a molecule comprising at least one ribonucleotide residue. By “ribonucleotide” is meant a nucleotide with a hydroxyl group at the 2'-position of a beta-D-ribo-furanose moiety. The term includes double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

As used herein, the terms “complementarity” or “complementary” means that a nucleic acid can form hydrogen bond(s) with another nucleic acid sequence by either traditional Watson-Crick or other non-traditional types of interaction. In reference to the nucleic molecules described according to the present invention, the binding free energy for a nucleic acid molecule with its complementary sequence is sufficient to allow the relevant function of the nucleic acid to proceed, e.g., RNAi activity. For example, the degree of complementarity between the sense and antisense strand of the siRNA construct can be the same or different from the degree of complementarity between the antisense strand of the siRNA and the target RNA sequence. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). “Perfectly complementary” means that all the contiguous residues of a nucleic acid sequence will hydrogen bond with the same number of contiguous residues in a second nucleic acid sequence.

Preferably, a nucleic acid is "complementary" to another nucleic acid if the two sequences are capable of hybridizing and forming a stable duplex with one another, with hybridization preferably being carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

Preferably, the degree of complementarity according to the invention is at least 70%, preferably at least 75%, more preferably at least 80%, even more preferably at least 90% or most preferably at least 95%, 96%, 97%, 98% or 99%.

Preferably the degree of identity between a specific nucleic acid sequence described herein and a nucleic acid sequence which is a derivative of said specific nucleic acid sequence, which hybridizes with said specific nucleic acid sequence and/or which is degenerate with respect to said specific nucleic acid sequence will be at least 70%, preferably at least 75%, preferably at least 80%, more preferably at least 85%, even more preferably at least 90% or most preferably at least 95%, 96%, 97%, 98% or 99%. The degree of identity is preferably given for a region of at least about 30, at least about 50, at least about 70, at least about 90, at least about 100, at least about 200, at least about 300, at least about 400, at least about 500, at least about 1000, at least about 1500, or at least about 2000 nucleotides. In preferred embodiments, the degree of identity is given for the entire length of the reference nucleic acid sequence, such as the nucleic acid sequences given in the sequence listing.

"Sequence similarity" indicates the percentage of amino acids that either are identical or that represent conservative amino acid substitutions. "Sequence identity" between two polypeptide or nucleic acid sequences indicates the percentage of amino acids or nucleotides that are identical between the sequences.

The term "percentage identity" is intended to denote a percentage of nucleotides or of amino acid residues which are identical between the two sequences to be compared, obtained after the best alignment, this percentage being purely statistical and the differences between the two sequences being distributed randomly and over their entire length. Sequence comparisons between two nucleotide or amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

As used herein, a nucleic acid sequence "substantially identical" to a target sequence, e.g., a target sequence contained within a target mRNA, is a nucleic acid sequence which is identical to the target sequence, or which differs from the target sequence by one or more nucleotides. Sense strands of siRNAs described herein which comprise nucleic acid sequences substantially identical to a target sequence are characterized in that siRNA comprising such sense strands induce RNAi-mediated degradation of mRNA containing the target sequence. For example, an siRNA can comprise a sense strand which differs from a target sequence by one, two or three or more nucleotides, as long as RNAi-mediated degradation of the target mRNA is induced by the siRNA.

Nucleic acids may, according to the invention, be present alone or in combination with other nucleic acids, which may be homologous or heterologous. In preferred embodiments, a nucleic acid is functionally linked to expression control sequences which may be homologous or heterologous with respect to said nucleic acid. The term "homologous" means that a nucleic acid is also functionally linked to the expression control sequence naturally and the term "heterologous" means that a nucleic acid is not functionally linked to the expression control sequence naturally.

A nucleic acid, such as a nucleic acid expressing RNA and/or protein or peptide, and an expression control sequence are "functionally" linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term "expression control sequence" comprises according to the invention promoters, ribosome binding sites, enhancers and other control elements which regulate transcription of a gene or translation of a mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the functionally linked nucleic acid. Expression control sequences may also comprise enhancer sequences or upstream activator sequences.

According to the invention the term "promoter" or "promoter region" relates to a nucleic acid sequence which is located upstream (5') to the nucleic acid sequence being expressed and controls expression of the sequence by providing a recognition and binding site for RNA-polymerase. The "promoter region" may include further recognition and binding sites for further factors which are involved in the regulation of transcription of a gene. A promoter may control the transcription of a prokaryotic or eukaryotic gene. Furthermore, a promoter may be "inducible" and may initiate transcription in response to an inducing agent or may be "constitutive" if transcription is not controlled by an inducing agent. A gene which is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

Promoters which are preferred according to the invention include promoters for SP6, T3 and T7 polymerase, human U6 RNA promoter, and CMV promoter.

According to the invention, the term "expression" is used in its most general meaning and comprises the production of RNA or of RNA and protein/peptide. It also comprises partial expression of nucleic acids. Furthermore, expression may be carried out transiently or stably.

In a preferred embodiment, a nucleic acid molecule is according to the invention present in a vector, where appropriate with a promoter, which controls expression of the nucleic acid. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. Vectors comprise plasmids, phagemids, bacteriophages or viral genomes. The term "plasmid" as used herein generally relates to a construct of extrachromosomal genetic material, usually a circular DNA duplex, which can replicate independently of chromosomal DNA.

According to the invention, the term "host cell" relates to any cell which can be transformed or transfected with an exogenous nucleic acid. The term "host cells" comprises according to the invention prokaryotic (e.g. *E. coli*) or eukaryotic cells (e.g. mammalian cells, in particular human cells, yeast cells and insect cells). Particular preference is given to mammalian cells such as cells from humans, mice, hamsters, pigs, goats, or primates. The cells may be derived from a multiplicity of tissue types and comprise primary cells and cell lines. Specific examples comprise keratinocytes, peripheral blood leukocytes, stem cells of the bone marrow and embryonic stem cells. In further embodiments, the host cell is an antigen-presenting cell, in particular a dendritic cell, monocyte or a macrophage. A nucleic acid may be present in the host cell in the form of a single copy or of two or more copies and, in one embodiment, is expressed in the host cell.

In those cases of the invention in which a MHC molecule presents a protein or peptide, an expression vector may also comprise a nucleic acid sequence coding for said MHC molecule. The nucleic acid sequence coding for the MHC molecule may be present on the same expression vector as the nucleic acid coding for the protein or peptide, or both nucleic acids may be present on different expression vectors. In the latter case, the two expression vectors may be cotransfected into a cell. If a host cell expresses neither the protein or peptide nor the MHC molecule, both nucleic acids coding therefor may be transfected into the cell either on the same expression vector or on different expression vectors. If the cell already expresses the MHC molecule, only the nucleic acid sequence coding for the protein or peptide can be transfected into the cell.

A nucleic acid can be detected or its amount determined by amplification of said nucleic acid. Amplification of a nucleic acid can be done using a pair of amplification primers, i.e. oligonucleotides, which hybridize to the nucleic acid. The primers preferably comprise a sequence of 6-50, in particular 10-30, 15-30 and 20-30 contiguous nucleotides of the nucleic acid and are nonoverlapping, in order to avoid the formation of primer dimers. One of the primers will hybridize to one strand of the nucleic acid to be amplified, and the other primer will hybridize to the complementary strand in an arrangement which allows amplification of the nucleic acid.

"Antisense molecules" or "antisense nucleic acids" may be used for regulating, in particular reducing, expression of a nucleic acid. The term "antisense molecule" or "antisense nucleic acid" refers according to the invention to an oligonucleotide which hybridizes under physiological conditions to DNA comprising a particular gene or to mRNA of said gene, thereby inhibiting transcription of said gene and/or translation of said mRNA. According to the invention, an "antisense molecule" also comprises a construct which contains a nucleic acid or a part thereof in reverse orientation with respect to its natural promoter. An antisense transcript of a nucleic acid or of a part thereof may form a duplex with the naturally occurring mRNA specifying the protein and thus prevent accumulation of or translation of the mRNA into the protein. Another possibility is the use of ribozymes for inactivating a nucleic acid. Antisense oligonucleotides preferred according to the invention have a sequence of 6-50, in particular 10-30, 15-30 and 20-30, contiguous nucleotides of the target nucleic acid and preferably are fully complementary to the target nucleic acid or to a part thereof.

In preferred embodiments, the antisense oligonucleotide hybridizes with an N-terminal or 5' upstream site such as a translation initiation site, transcription initiation site or promoter site. In further embodiments, the antisense oligonucleotide hybridizes with a 3' untranslated region or mRNA splicing site.

According to the invention an oligonucleotide may be an oligoribonucleotide, oligodeoxyribonucleotide, modified oligoribonucleotide or modified oligodeoxyribonucleotide.

In one embodiment, an oligonucleotide consists of ribonucleotides, deoxyribonucleotides or a combination thereof, with the 5'-end of one nucleotide and the 3'-end of another nucleotide being linked to one another by a phosphodiester bond. These oligonucleotides may be synthesized in the conventional manner or produced recombinantly.

In preferred embodiments, an oligonucleotide is a "modified" oligonucleotide. Here, the oligonucleotide may be modified in very different ways, without impairing its ability to bind its target, in order to increase, for example, its stability. According to the invention, the term "modified oligonucleotide" means an oligonucleotide in which (i) at least two of its nucleotides are linked to one another by a synthetic internucleoside bond (i.e. an internucleoside bond which is not a phosphodiester bond) and/or (ii) a chemical group which is usually not found in nucleic acids is covalently linked to the oligonucleotide. Preferred synthetic internucleoside bonds are phosphorothioates, alkyl phosphonates, phosphorodithioates, phosphate esters, alkyl phosphonothioates, phosphoramidates, carbamates, carbonates, phosphate triesters, acetamidates, carboxymethyl esters and peptides.

The term "modified oligonucleotide" also comprises oligonucleotides having one or more covalently modified bases and/or one or more covalently modified sugars. "Modified oligonucleotides" comprise, for example, oligonucleotides with sugar residues which are covalently bound to low molecular weight organic groups other than a hydroxyl group at the 3'-position and a phosphate group at the 5'-position. Modified oligonucleotides may comprise, for example, a 2'-O-alkylated ribose residue or another sugar instead of ribose, such as arabinose.

By "small interfering RNA" or "siRNA" as used herein is meant an isolated RNA molecule, preferably greater than 10 nucleotides in length, more preferably greater than 15 nucleotides in length, and most preferably 18, 19, 20, 21, 22, 23, 24, 25, 26, 27, 28, 29, or 30 nucleotides in length that is used to identify a target gene or mRNA to be degraded. A range of 19-25 nucleotides is the most preferred size for siRNAs.

siRNA according to the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA; modifications that make the siRNA resistant to nuclease digestion (e.g., the use of 2'-substituted ribonucleotides or modifications to the sugar-phosphate backbone); or the substitution of one or more nucleotides in the siRNA with deoxyribonucleotides. Furthermore, siRNA may be modified to increase the stability thereof as described above for modified oligonucleotides, in particular by introducing one or more phosphorothioate linkages.

One or both strands of the siRNA can also comprise a 3'-overhang. As used herein, a "3'-overhang" refers to at least one unpaired nucleotide extending from the 3'-end of an RNA strand. Thus in one embodiment, the siRNA comprises at least one 3'-overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length. In the embodiment in which both strands of the siRNA molecule comprise a 3'-overhang, the length of the overhangs can be the same or different for each strand. In a most preferred embodiment, the 3'-overhang is present on both strands of the siRNA, and is 2 nucleotides in length. For example, each strand of the siRNA of the invention can comprise 3'-overhangs of dideoxythymidylic acid ("TT") or diuridylic acid ("uu").

In order to enhance the stability of the siRNA, the 3'-overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3'-overhangs with 2'-deoxythymidine, is tolerated and does not affect the efficiency of RNAi degradation. In particular, the absence of a 2'-hydroxyl in the 2'-deoxythymidine significantly enhances the nuclease resistance of the 3'-overhang in tissue culture medium.

The sense and antisense strands of the siRNA can comprise two complementary, single-stranded RNA molecules or can comprise a single molecule in which two complementary portions are base-paired and are covalently linked by a single-stranded "hairpin" area. That is, the sense region and antisense region can be covalently connected via a linker molecule. The linker molecule can be a polynucleotide or non-nucleotide linker. Without wishing to be bound by any theory, it is believed that the hairpin area of the latter type of siRNA molecule is cleaved intracellularly by the "Dicer" protein (or its equivalent) to form a siRNA of two individual base-paired RNA molecules.

As used herein, "target mRNA" refers to an RNA molecule that is a target for downregulation. One skilled in the art would understand that the cDNA sequence is equivalent to the mRNA sequence, and can be used for the same purpose herein, i.e., the generation of siRNA.

As used herein, a gene or mRNA which is "cognate" to human TPTE or CXCR4 is a gene or mRNA from another mammalian species which is homologous to human TPTE or CXCR4.

The mRNA transcribed from the human TPTE or CXCR4 gene can be analyzed for alternative splice forms using techniques well-known in the art. Such techniques include reverse transcription-polymerase chain reaction (RT-PCR), northern blotting and in-situ hybridization.

A technique called "RNAse protection" can also be used to identify alternatively spliced TPTE or CXCR4 mRNAs. RNAse protection involves transcription of a gene sequence into synthetic RNA, which is hybridized to RNA derived from other cells; for example, cells which are induced to express TPTE. The hybridized RNA is then incubated with enzymes that recognize RNA:RNA hybrid mismatches. Smaller than expected fragments indicate the presence of alternatively spliced mRNAs. The putative alternatively spliced mRNAs can be cloned and sequenced by methods well known to those skilled in the art.

RT-PCR can also be used to identify alternatively spliced TPTE or CXCR4 mRNAs. In RT-PCR, mRNA from cells known to express TPTE or CXCR4 is converted into cDNA by the enzyme reverse transcriptase, using methods well-known to those of ordinary skill in the art. The entire coding sequence of the cDNA is then amplified via PCR using a forward primer located in the 3' untranslated region, and a reverse primer located in the 5' untranslated region. The amplified products can be analyzed for alternative splice forms, for example by comparing the size of the amplified products with the size of the expected product from normally spliced mRNA, e.g., by agarose gel electrophoresis. Any change in the size of the amplified product can indicate alternative splicing.

The mRNA produced from mutant TPTE or CXCR4 genes can also be readily identified with the techniques described above for identifying alternative splice forms. As used herein, "mutant" TPTE or CXCR4 genes or mRNA include human TPTE or CXCR4 genes or mRNA which differ in sequence from the TPTE or CXCR4 sequences set forth herein. Thus, allelic forms of the TPTE or CXCR4 gene, and the mRNA produced from them, are considered "mutants" for purposes of this invention.

"Reduce" or "inhibit" as used herein means the ability to cause an overall decrease, preferably of 20% or greater, more preferably of 50% or greater, and most preferably of 75% or greater, in the level, e.g. in the level of protein or mRNA as compared to a reference sample (e.g., a sample not treated with siRNA). This reduction or inhibition of RNA or protein expression can occur through targeted mRNA cleavage or degradation. Assays for protein expression or nucleic acid expression are known in the art and include, for example, ELISA, western blot analysis for protein expression, and northern blotting or RNase protection assays for RNA.

siRNA can be expressed from pol III expression vectors without a change in targeting site, as expression of RNAs from pol III promoters is only believed to be efficient when the first transcribed nucleotide is a purine.

siRNA according to the invention can be targeted to any stretch of approximately 19-25 contiguous nucleotides in any of the target mRNA sequences (the "target sequence"). Techniques for selecting target sequences for siRNA are given, for example, in Tuschl T. et al., “The siRNA User Guide”, revised Oct. 11, 2002, the entire disclosure of which is herein incorporated by reference. “The siRNA User Guide” is available on the world wide web at a website maintained by Dr. Thomas Tuschl, Laboratory of RNA Molecular Biology, Rockefeller University, New York, USA, and can be found by accessing the website of the Rockefeller University and searching with the keyword “siRNA”. Thus, the sense strand of the present siRNA comprises a nucleotide sequence substantially identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3'-direction) from the start codon. The target sequence can, however, be located in the 5'- or 3'-untranslated regions, or in the region nearby the start codon. For example, a suitable target sequence in the TPTE cDNA sequence is selected from the following group of target sequences:

```
(i)
                        (SEQ ID NO: 15)
TCGGTACTTGATAACATTACA

(ii)
                        (SEQ ID NO: 18)
CAGACTTGTGTTATTCTAGCA

(iii)
                        (SEQ ID NO: 21)
CTGAAATATGTTCAACTGCAA

(iv)
                        (SEQ ID NO: 24)
CAGATTGGCAACCAAGACTAA

(v)
                        (SEQ ID NO: 27)
AACCCTGCCACATGTTCATAT

(vi)
                        (SEQ ID NO: 30)
AATGACAGTCCACAGACAAGT

(vii)
                        (SEQ ID NO: 33)
AAGCTGATAAGAAGGCGGGTT
```

A preferred siRNA targeting the sequence (i), and which has 3'-overhangs on each strand (overhangs shown in bold), is:

(SEQ ID NO: 16)
gguacuugauaacauuacaTT

(SEQ ID NO: 17)
AGccaugaacuauuguaaugu

A preferred siRNA targeting the sequence (ii), and which has 3'-overhangs on each strand (overhangs shown in bold), is:

(SEQ ID NO: 19)
gacuuguguuauucuagcaTT

(SEQ ID NO: 20)
GTcugaacacaauaagaucgu

A preferred siRNA targeting the sequence (iii), and which has 3'-overhangs on each strand (overhangs shown in bold), is:

(SEQ ID NO: 22)
gaaauauguucaacugcaaTT

(SEQ ID NO: 23)
GAcuuuauacaaguugacguu

A preferred siRNA targeting the sequence (iv), and which has 3'-overhangs on each strand (overhangs shown in bold), is:

(SEQ ID NO: 25)
gauuggcaaccaagacuaaTT

(SEQ ID NO: 26)
GTcuaaccguugguucugauu

A preferred siRNA targeting the sequence (v), and which has 3'-overhangs on each strand (overhangs shown in bold), is:

(SEQ ID NO: 28)
cccugccacauguucauauTT

(SEQ ID NO: 29)
TTgggacgguguacaaguaua

A preferred siRNA targeting the sequence (vi), and which has 3'-overhangs on each strand (overhangs shown in bold), is:

(SEQ ID NO: 31)
ugacaguccacagacaaguTT

(SEQ ID NO: 32)
TTacugucaggugucuguuca

A preferred siRNA targeting the sequence (vii), and which has 3'-overhangs on each strand (overhangs shown in bold), is:

(SEQ ID NO: 34)
gcugauaagaaggcggguuTT

(SEQ ID NO: 35)
TTcgacuauucuuccgcccaa

In the above list, all deoxyribonucleotides in a nucleic acid sequence are represented by capital letters (e.g., deoxythymidine is “T”), and ribonucleotides in a nucleic acid sequence are represented by lower case letters (e.g., uridine is “u”).

It is understood that the target sequences given herein are with reference to the human TPTE cDNA, and thus these sequences contain deoxythymidines represented by T. One skilled in the art would understand that, in the actual target sequence of the TPTE mRNA, the deoxythymidines would be replaced by uridines (“u”). Likewise, a target sequence contained within an siRNA of the invention would also contain uridines in place of deoxythymidines.

siRNA can be obtained using a number of techniques known to those of skill in the art. For example, siRNA can be chemically synthesized or recombinantly produced using methods known in the art, such as the Drosophila in vitro system described in U.S. published application 2002/0086356 of Tuschl et al., the entire disclosure of which is herein incorporated by reference.

Preferably, siRNA is chemically synthesized using appropriately protected ribonucleoside phosphoramidites and a conventional DNA/RNA synthesizer. siRNA can be synthesized as two separate, complementary RNA molecules, or as a single RNA molecule with two complementary regions.

Alternatively, siRNA can also be expressed from recombinant circular or linear DNA plasmids using any suitable promoter. Suitable promoters for expressing siRNA of the invention from a plasmid include, for example, the U6 or H1 RNA pol III promoter sequences and the cytomegalovirus promoter.

Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly. The use of recombinant plasmids to deliver siRNA to cells in vivo is discussed in more detail below. siRNA can be expressed from a recombinant plasmid either as two separate, complementary RNA molecules, or as a single RNA molecule with two complementary regions.

Selection of plasmids suitable for expressing siRNA, methods for inserting nucleic acid sequences for expressing the siRNA into the plasmid, and methods of delivering the recombinant plasmid to the cells of interest are within the skill in the art.

siRNA can also be expressed from recombinant viral vectors intracellularly in vivo. The recombinant viral vectors comprise sequences encoding the siRNA and any suitable promoter for expressing the siRNA sequences. The recombinant viral vectors can also comprise inducible or regulatable promoters for expression of the siRNA in a particular tissue or in a particular intracellular environment. The use of recombinant viral vectors to deliver siRNA to cells in vivo is discussed in more detail below. siRNA can be expressed from a recombinant viral vector either as two separate, complementary RNA molecules, or as a single RNA molecule with two complementary regions.

According to the invention the term "peptide" refers to substances comprising two or more, preferably 3 or more, preferably 4 or more, preferably 6 or more, preferably 8 or more, preferably 10 or more, preferably 13 or more, preferably 16 more, preferably 20 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used in this application interchangeably.

Preferably, the proteins and peptides described according to the invention have been isolated. The terms "isolated protein" or "isolated peptide" mean that the protein or peptide has been separated from its natural environment. An isolated protein or peptide may be in an essentially purified state. The term "essentially purified" means that the protein or peptide is essentially free of other substances with which it is associated in nature or in vivo.

Such proteins and peptides may be used, for example, in producing antibodies and in an immunological or diagnostic assay. Proteins and peptides described according to the invention may be isolated from biological samples such as tissue or cell homogenates and may also be expressed recombinantly in a multiplicity of pro- or eukaryotic expression systems.

For the purposes of the present invention, "derivatives" of a protein or peptide or of an amino acid sequence comprise amino acid insertion variants, amino acid deletion variants and/or amino acid substitution variants.

Amino acid insertion variants comprise amino- and/or carboxy-terminal fusions and also insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid deletion variants are characterized by the removal of one or more amino acids from the sequence.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties such as hydrophobicity, hydrophilicity, electronegativity, volume of the side chain and the like (conservative substitution). Conservative substitutions, for example, relate to the exchange of one amino acid with another amino acid listed below in the same group as the amino acid to be substituted:

1. small aliphatic, nonpolar or slightly polar residues: Ala, Ser, Thr (Pro, Gly)
2. negatively charged residues and their amides: Asn, Asp, Glu, Gln
3. positively charged residues: His, Arg, Lys
4. large aliphatic, nonpolar residues: Met, Leu, Ile, Val (Cys)
5. large aromatic residues: Phe, Tyr, Trp.

Owing to their particular part in protein architecture, three residues are shown in brackets. Gly is the only residue without a side chain and thus imparts flexibility to the chain. Pro has an unusual geometry which greatly restricts the chain. Cys can form a disulfide bridge.

Preferably the degree of similarity, preferably identity between a specific amino acid sequence described herein and an amino acid sequence which is a derivative of said specific amino acid sequence will be at least 70%, preferably at least 80%, even more preferably at least 90% or most preferably at least 95%, 96%, 97%, 98% or 99%. The degree of similarity or identity is given preferably for a region of at least about 10, at least about 20, at least about 40, at least about 60, at least about 80, at least about 100, at least about 150, at least about 200, at least about 300, at least about 400 or 500 amino acids. In preferred embodiments, the degree of similarity or identity is given for the entire length of the reference amino acid sequence.

The amino acid variants described above may be readily prepared with the aid of known peptide synthesis techniques such as, for example, by solid phase synthesis (Merrifield, 1964) and similar methods or by recombinant DNA manipulation. The manipulation of DNA sequences for preparing proteins and peptides having substitutions, insertions or deletions, is described in detail in Sambrook et al. (1989), for example.

According to the invention, "derivatives" of proteins and peptides also comprise single or multiple substitutions, deletions and/or additions of any molecules associated with the protein or peptide, such as carbohydrates, lipids and/or proteins or peptides. The term "derivative" also extends to all functional chemical equivalents of said proteins and peptides which do not only contain amino acid constituents but also non-amino acid constituents such as sugar and phosphate structures and extends also to substances containing bonds such ester, thioether and disulfide bonds.

According to the invention, a part or fragment of a protein or peptide preferably has a functional property of the protein or peptide from which it has been derived. Such functional properties comprise the interaction with antibodies, and the interaction with other peptides or proteins. A particular property is the ability to form a complex with MHC molecules and, where appropriate, generate an immune response, preferably by stimulating cytotoxic or T helper cells. A part or fragment of a protein or peptide preferably comprises a sequence of at least 6, in particular at least 8, at least 10, at least 12, at least 15, at least 20, at least 30 and preferably up to 8, in particular up to 10, up to 12, up to 15, up to 20, up to 30 or up to 50, consecutive amino acids of the protein or peptide.

A part or a fragment of a nucleic acid coding for a protein or peptide preferably relates to the part of the nucleic acid, which codes at least for the protein or peptide and/or for a part or a fragment of said protein or peptide, as defined above. A part or fragment of a nucleic acid coding for a protein or peptide is preferably that part of the nucleic acid corresponding to the open reading frame.

Antisera which contain specific antibodies specifically binding to the target protein can be prepared by various standard processes; see, for example, "Monoclonal Antibodies: A Practical Approach" by Philip Shepherd, Christopher Dean ISBN 0-19-963722-9; "Antibodies: A Laboratory Manual" by Ed Harlow, David Lane, ISBN: 0879693142 and "Using Antibodies: A Laboratory Manual: Portable Protocol NO" by Edward Harlow, David Lane, Ed Harlow ISBN 0879695447. Thereby it is also possible to generate affine and specific antibodies which recognize complex membrane proteins in their native form (Azorsa et al., J. Immunol. Methods 229: 35-48, 1999; Anderson et al., J. Immunol. 143: 1899-1904, 1989; Gardsvoll, J. Immunol. Methods 234: 107-116, 2000). This is in particular relevant for the preparation of antibodies which are to be used therapeutically, but also for many diagnostic applications. In this respect, it is possible to immunize with the whole protein, with extracellular partial sequences as well as with cells which express the target molecule in physiologically folded form.

Monoclonal antibodies are traditionally prepared using the hybridoma technology. (for technical details see: "Monoclonal Antibodies: A Practical Approach" by Philip Shepherd, Christopher Dean ISBN 0-19-963722-9; "Antibodies: A Laboratory Manual" by Ed Harlow, David Lane ISBN: 0879693142; "Using Antibodies: A Laboratory Manual: Portable Protocol NO" by Edward Harlow, David Lane, Ed Harlow ISBN: 0879695447).

It is known that only a small part of an antibody molecule, the paratope, is involved in binding of the antibody to its epitope (cf. Clark, W. R. (1986), *The Experimental Foundations of Modern Immunology*, Wiley & Sons, Inc., New York; Roitt, I. (1991), Essential Immunology, 7th Edition, Blackwell Scientific Publications, Oxford). The pFc' and Fc regions are, for example, effectors of the complement cascade but are not involved in antigen binding. An antibody from which the pFc' region has been enzymatically removed or which has been produced without the pFc' region, referred to as $F(ab')_2$ fragment, carries both antigen binding sites of a complete antibody. Similarly, an antibody from which the Fc region has been enzymatically removed or which has been produced without said Fc region, referred to as Fab fragment, carries one antigen binding site of an intact antibody molecule. Furthermore, Fab fragments consist of a covalently bound light chain of an antibody and part of the heavy chain of said antibody, referred to as Fd. The Fd fragments are the main determinants of antibody specificity (a single Fd fragment can be associated with up to ten different light chains, without altering the specificity of the antibody) and Fd fragments, when isolated, retain the ability to bind to an epitope.

Located within the antigen-binding part of an antibody are complementary-determining regions (CDRs) which interact directly with the antigen epitope and framework regions (FRs) which maintain the tertiary structure of the paratope. Both the Fd fragment of the heavy chain and the light chain of IgG immunoglobulins contain four framework regions (FR1 to FR4) which are separated in each case by three complementary-determining regions (CDR1 to CDR3). The CDRs and, in particular, the CDR3 regions and, still more particularly, the CDR3 region of the heavy chain are responsible to a large extent for antibody specificity.

Non-CDR regions of a mammalian antibody are known to be able to be replaced by similar regions of antibodies with the same or a different specificity, with the specificity for the epitope of the original antibody being retained. This made possible the development of "humanized" antibodies in which nonhuman CDRs are covalently linked to human FR and/or Fc/pFc' regions to produce a functional antibody.

As another example, WO 92/04381 describes the production and use of humanized murine RSV antibodies in which at least part of the murine FR regions have been replaced with FR regions of a human origin. Antibodies of this kind, including fragments of intact antibodies with antigen-binding capability, are often referred to as "chimeric" antibodies.

According to the invention, the term "antibody" also includes $F(ab')_2$, Fab, Fv, and Fd fragments of antibodies, chimeric antibodies, in which the Fc and/or FR and/or CDR1 and/or CDR2 and/or light chain-CDR3 regions have been replaced with homologous human or nonhuman sequences, chimeric $F(ab')_2$-fragment antibodies in which the FR and/or CDR1 and/or CDR2 and/or light chain-CDR3 regions have been replaced with homologous human or nonhuman sequences, chimeric Fab-fragment antibodies in which the FR and/or CDR1 and/or CDR2 and/or light chain-CDR3 regions have been replaced with homologous human or nonhuman sequences, and chimeric Fd-fragment antibodies in which the FR and/or CDR1 and/or CDR2 regions have been replaced with homologous human or nonhuman sequences. The term "antibody" also comprises "single-chain" antibodies.

Antibodies may also be coupled to specific diagnostic substances for displaying cells and tissues expressing particular proteins or peptides.

Diagnostic substances include any label that functions to: (i) provide a detectable signal; (ii) interact with a second label to modify the detectable signal provided by the first or second label, e.g. FRET (Fluorescence Resonance Energy Transfer); (iii) affect mobility, e.g. electrophoretic mobility, by charge, hydrophobicity, shape, or other physical parameters, or (iv) provide a capture moiety, e.g., affinity, antibody/antigen, or ionic complexation. Suitable as label are structures, such as fluorescent labels, luminescent labels, chromophore labels, radioisotopic labels, isotopic labels, preferably stable isotopic labels, isobaric labels, enzyme labels, particle labels, in particular metal particle labels, magnetic particle labels, polymer particle labels, small organic molecules such as biotin, ligands of receptors or binding molecules such as cell adhesion proteins or lectins, label-sequences comprising nucleic acids and/or amino acid residues which can be detected by use of binding agents, etc. Diagnostic substances comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium.

Antibodies may also be coupled to specific therapeutic substances.

According to the invention, the term "therapeutic substance" means any molecule which may exert a therapeutic effect. According to the invention, a therapeutic substance is preferably selectively guided to a diseased cell and includes anticancer agents, radioactive iodine-labeled compounds, toxins, cytostatic or cytolytic drugs, etc. Anticancer agents comprise, for example, aminoglutethimide, azathioprine, bleomycin sulfate, busulfan, carmustine, chlorambucil, cisplatin, cyclophosphamide, cyclosporine, cytarabidine, dacarbazine, dactinomycin, daunorubin, doxorubicin, taxol, etoposide, fluorouracil, interferon-α, lomustine, mercaptopurine, methotrexate, mitotane, procarbazine HCl, thioguanine, vinblastine sulfate and vincristine sulfate. Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60.

The term "major histocompatibility complex" or "MHC" relates to a complex of genes present in all vertebrates. MHC proteins or molecules are involved in signaling between lymphocytes and antigen presenting cells in normal immune reactions by binding peptides and presenting them for recognition by T cell receptors (TCR). MHC molecules bind peptides within an intracellular processing compartment and present these peptides on the surface of antigen presenting cells for recognition by T cells. The human MHC region also termed HLA is located on chromosome 6 and includes the class I and class II region. In one preferred embodiment of all aspects of the invention an MHC molecule is an HLA molecule.

The term "patient" or "subject" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

"Abnormal expression" means according to the invention that expression is altered, preferably increased, compared to the state in a healthy individual.

According to the invention the term "increased" or "increased amount" preferably refers to an increase by at least 10%, in particular at least 20%, at least 50% or at least 100%. The amount of a substance is also increased in a test sample such as a biological sample compared to a reference sample if it is detectable in the test sample but absent or not detectable in the reference sample.

According to the invention, the term "disease" refers to any pathological state, including, in particular, cancer, wherein the term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

By "tumor" is meant an abnormal group of cells or tissue that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign or malignant.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The term "relapse" relates to the return of signs and symptoms of a disease after a patient has enjoyed a remission, e.g. after therapy such as tumor resection, chemotherapy and/or radiation therapy. In particular, the term "relapse" relates to the reappearance of cancer after a disease-free period. For example, after treatment a patient with cancer went into remission with no sign or symptom of the tumor, remained in remission for some time, but then suffered a relapse and has to be treated once again for cancer.

According to the invention, a biological sample may be a tissue sample, including bodily fluids, and/or a cellular sample and may be obtained in the conventional manner such as by tissue biopsy, including punch biopsy, and by taking blood, bronchial aspirate, sputum, urine, feces or other body fluids. According to the invention, the term "biological sample" also includes fractions of biological samples.

The terms "T cell" and "T lymphocyte" are used interchangeably herein and include T helper cells and cytolytic T cells which comprise cytotoxic T cells.

The pharmaceutical compositions and methods of treatment described according to the invention may also be used for immunization or vaccination to prevent a disease described herein.

In the present methods, nucleic acids can be administered to the subject either as naked nucleic acids, in conjunction with a delivery reagent, or as a recombinant plasmid or viral vector which may express the nucleic acid. The invention also provides for administering nucleic acids in vivo by using target-controlled liposomes.

For example vectors derived from adenovirus (AV); adeno-associated virus (AAV); retroviruses (e.g., lentiviruses (LV), Rhabdoviruses, murine leukemia virus); herpes virus, and the like can be used. The tropism of the viral vectors can be modified by pseudotyping the vectors with envelope proteins or other surface antigens from other viruses, or by substituting different viral capsid proteins, as appropriate.

Liposomes can aid in the delivery of the nucleic acid to a particular tissue, such as tumor tissue, and can also increase the blood half-life of the nucleic acid. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), Ann. Rev. Biophys. Bioeng. 9: 467; and U.S. Pat. Nos. 4,235,871, 4,501,728, 4,837,028, and 5,019,369, the entire disclosures of which are herein incorporated by reference.

In particular embodiments, preference is given to directing nucleic acids to particular cells. In such embodiments, a carrier used for administering a nucleic acid to a cell (e.g. a retrovirus or a liposome) may have a bound target control molecule. For example, a molecule such as an antibody specific for a surface membrane protein on the target cell or a ligand for a receptor on the target cell may be incorporated into or attached to the nucleic acid carrier. Preferred antibodies comprise antibodies which bind selectively an antigen associated with tumor cells. If administration of a nucleic acid via liposomes is desired, proteins binding to a surface membrane protein associated with endocytosis may be incorporated into the liposome formulation in order to make target control and/or uptake possible. Such proteins comprise capsid proteins or fragments thereof which are specific for a particular cell type, antibodies to proteins which are internalized, proteins addressing an intracellular site, and the like.

RNAi-mediated degradation of the target mRNA can be detected by measuring levels of the target mRNA or protein, using standard techniques for isolating and quantifying mRNA such as Northern blot or dot blotting techniques, or quantitative RT-PCR or protein such as ELISA or Western blot.

The therapeutic compositions of the invention may be administered in pharmaceutically compatible preparations. Such preparations may usually contain pharmaceutically compatible concentrations of salts, buffer substances, preservatives, carriers, supplementing immunity-enhancing substances such as adjuvants, e.g. CpG oligonucleotides, cytokines, chemokines, saponin, GM-CSF and/or RNA and, where appropriate, other therapeutically active compounds.

The therapeutically active compounds of the invention may be administered via any conventional route, including by injection or infusion. The administration may be carried out, for example, orally, intravenously, intraperitonealy, intramuscularly, subcutaneously or transdermally.

Suitable techniques for delivering nucleic acids to cells include administration of the nucleic acid to a subject by gene gun, electroporation, nanoparticles, micro-encapsulation, and the like, or by parenteral and enteral administration routes.

Suitable enteral administration routes include oral, rectal, or intranasal delivery.

Suitable parenteral administration routes include intravascular administration (e.g. intravenous bolus injection, intravenous infusion, intra-arterial bolus injection, intra-arterial infusion and catheter instillation into the vasculature); peri- and intra-tissue administration (e.g., peri-tumoral and intratumoral injection); subcutaneous injection or deposition including subcutaneous infusion (such as by osmotic pumps); direct (e.g., topical) application at or near the site of the diseased area, for example by a catheter or other placement device (e.g., a suppository, or an implant comprising a porous, non-porous, or gelatinous material); and inhalation.

The compositions of the invention are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. As used herein, an "effective amount" of the siRNA is preferably an amount sufficient to cause RNAi-mediated degradation of the target mRNA in a subject.

An effective amount of a composition of the invention will depend on feelers such as the condition to be treated, the severeness of the disease, the individual parameters of the patient, including age, physiological condition, size and weight, the duration of treatment, the type of an accompanying therapy (if present), the specific route of administration and similar factors.

The compositions of the invention can be administered to a subject in combination with another therapeutic method designed to treat the pathology. For example, they can be administered in combination with therapeutic methods currently employed for treating cancer or preventing tumor metastasis (e.g., radiation therapy, chemotherapy, and surgery). For treating tumors, the compositions of the invention are preferably administered to a subject in combination with radiation therapy, or in combination with chemotherapeutic agents such as cisplatin, carboplatin, cyclophosphamide, 5-fluorouracil, adriamycin, daunorubicin ortamoxifen.

The pharmaceutical compositions of the invention are preferably sterile and contain an effective amount of the therapeutically active substance to generate the desired reaction or the desired effect.

The doses administered of the compositions of the invention may depend on various parameters such as the type of administration, the condition of the patient, the desired period of administration, etc. In the case that a reaction in a patient is insufficient with an initial dose, higher doses (or effectively higher doses achieved by a different, more localized route of administration) may be used.

The pharmaceutical compositions of the invention are generally administered in pharmaceutically compatible amounts and in pharmaceutically compatible compositions. The term "pharmaceutically compatible" refers to a nontoxic material which does not interact with the action of the active component of the pharmaceutical composition. Preparations of this kind may usually contain salts, buffer substances, preservatives, carriers and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a nonlimiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the invention may comprise a pharmaceutically compatible carrier. According to the invention, the term "pharmaceutically compatible carrier" refers to one or more compatible solid or liquid fillers, diluents or encapsulating substances, which are suitable for administration to humans. The term "carrier" refers to an organic or inorganic component, of a natural or synthetic nature, in which the active component is combined in order to facilitate application. The components of the pharmaceutical composition of the invention are usually such that no interaction occurs which substantially impairs the desired pharmaceutical efficacy.

The pharmaceutical compositions of the invention may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, solutions, suspensions, syrups, elixirs or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present invention is described in detail by the figures and examples below, which are used only for illustration purposes and are not meant to be limiting. Owing to the description and the examples, further embodiments which are likewise included in the invention are accessible to the skilled worker.

Example 1

Materials and Methods

Tissues and Cell Lines

This study was approved by the local ethical review board ("Ethikkommission der Ärztekammer des Landes Rheinland-Pfalz"). Recombinant DNA work was done with the official permission and according to the rules of the state government of Rheinland-Pfalz. Tissues were obtained as human surplus materials during routine diagnostic or therapeutic procedures and were stored at −80° C. until use. If not otherwise stated, cell lines were obtained from commercial providers. For demethylation studies cells were split to 20-30% confluency and cultured with 2 μM or 10 μM 5-Aza-2'-deoxycytidine (5-Aza-dC) (Sigma-Aldrich) for 72 h. Colon cancer cell lines $HCT116^{WT}$, $HCT116^{DNMT1-/-}$, $HCT116^{DNMT3b-/-}$ and $HCT116^{DKO}$ were kindly provided by Bert Vogelstein.

RNA-Isolation, RT-PCR and Real-Time RT-PCR

RNA extraction, first-strand cDNA synthesis, RT-PCR and real-time RT-PCR were performed as previously described (Koslowski, M. et al., Cancer Res. 62, 6750-6755 (2002), Koslowski, M. et al., *Cancer Res.* 64, 5988-5993 (2004)). All homologous members and pseudogenes have been aligned, to design specific primer pairs for TPTE. Specificity was confirmed by sequencing of randomly selected amplification products. For end-point analysis TPTE-specific oligonucleotides (sense 5'-TGG ATG TCA CTC TCA TCC TTG-3' (SEQ ID NO: 36); antisense 5'-CCA TAG TTC CTG TTC TAT CTG-3' (SEQ ID NO: 37); 63° C. annealing) were used in a 35 cycle RT-PCR. Real-time quantitative expression analysis was performed in triplicates using TPTE-specific oligonucleotides (sense 5'-GAG TCT ACA ATC TAT GCA GTG-3' (SEQ ID NO: 37); antisense 5'-CCA TAG TTC CTG TTC TAT CTG-3' (SEQ ID NO: 38); 63° C. annealing) in a 40 cycle PCR. After normalization to 18sRNA (sense 5'-CGA TGC TCT TAG CTG AGT GTC-3' (SEQ ID NO: 39); antisense 5'-TAA CCA GAC AAA TCG CTC CAC-3' (SEQ ID NO.: 40); 65° C. annealing) TPTE transcripts in tumor samples were quantified relative to normal tissues using AACT calculation.

Antisera, Immunochemistry and Western Blot

Polyclonal antiserum pAK2091 raised against the n-terminus (aa 1-51) of TPTE was generated by a custom antibody service (SeqLab). Immunohistochemistry was performed on formalin-fixed and paraffin-embedded tissue sections after antigen retrieval by boiling the slides for 15 minutes in citrate buffer (pH 6) followed by a cooling period of 15 minutes at room temperature. For Western blot analysis 60 μg of total protein extracted from cells lysed with Triton-X was used. Extracts were diluted in reducing sample buffer (Roth), subjected to SDS-PAGE and subsequently electrotransferred onto PVDF membrane (Pall). For immunostaining antibodies reactive to HER2/neu (Abcam), pAKT (Cell Signaling), AKT (Cell Signaling) and beta-Actin (Abcam) were used followed by horseradish-peroxidase conjugated goat anti-mouse and goat anti-rabbit secondary antibodies (Dako). Detection of the anti-TPTE pAK2091 primary antibody was performed using the anti-rabbit Envision+System (Dako) according to the manufacturer's instructions.

Expression of eGFP-Tagged TPTE in Eukaryotic Cells

The open reading frame of TPTE was amplified (sense primer 5'-GAG AGA AAG CTT CCA CCA TGA ATG AAA GTC CTG ATC CCA CTG ACC T-3' (SEQ ID NO: 41), antisense primer 5'-GAG AGA AAG CTT GAT CGG ATC CAG CTA CAA CAT CAC TGC AAG TC-3' (SEQ ID NO: 42)) introducing two HindIII sites. The amplified fragment was ligated into vectors pEGFP-C1 and pEGFP-N3 (BD Biosciences). Variant $TPTE_{C338S}$ carrying a mutation in the active site of the phosphatase domain was generated by PCR-mediated site directed mutagenesis.

Immunofluorescence and Colocalization Studies

Cells expressing TPTE either endogenously or heterologously upon transfection with vector constructs were grown on slides for 12-24 h and were fixed with 2% paraformaldehyde/0.1% saponin/PBS. Indirect immunofluorescence staining for TPTE was performed with pAK2091 polyclonal rabbit antiserum and a fluorescence-tagged secondary anti-rabbit IgG antibody. To analyze colocalization of TPTE with F-Actin we stained permeabilised, fixed cells with rhodamine-phalloidin (Molecular Probes). Expression plasmids for eGFP-tagged PH-domains of PLC-δ1 and AKT for visualization of membrane bound $PIP_2$ and $PIP_S$ by protein-protein interaction were kindly provided by Mario. J. Rebecchi and Julian Downward, respectively. Coverslips were mounted on slides in Slow-Fade (Molecular Probes) and analysed by immunofluorescence microscopy.

Immunopurification of eGFP-Fusion Proteins

Cells expressing eGFP-fusion proteins were lysed in buffer containing 1% Triton X-100 and protease inhibitors (8 μM Leupeptin, 3.3 μM Chymostatin, 2.9 μM Pepstatin A, 1 mM AEBSF-Hydrochloride). Lysates were spin down for 5 min at 4° C. For preclearing the lysates were incubated with protein A Sepharose CL-4B (Sigma-Aldrich) for 1 h at 4° C. The precleared lysates were incubated with anti-eGFP antibody (Delta Biolabs) for 2 h at 4° C. followed by incubation with protein A Sepharose CL-4B for 1 h at 4° C. and precipitated by centrifugation for 2 min. Immune complexes were washed with IP buffer (50 mM HEPES (pH 7.5), 150 mM NaCl), and resuspended in reaction buffer (100 mM HEPES (pH 7.5), 150 mM NaCl, 10 mM DTT). Proteins were separated by SDS-PAGE and analyzed by immunoblotting.

In Vitro Phosphatase Assay

To measure phosphatase activity PTEN and TPTE fusion proteins were immunoprecipitated and incubated in reaction buffer containing 110 μM water-soluble phosphatidylinositol phosphate (Echelon) for 90 min at 37° C. The amount of phosphate released from the substrate was determined using a malachite green assay (Echelon). After 15 min colour development the absorbance of the samples was measured at 620 nm on a Tecan Safire reader. Each sample was analyzed as triplicate.

siRNA Duplexes siRNA duplexes were designed following common rules and were purchased from Ambion. The TPTE siRNA duplex (sense 5'-r(GGU ACU UGA UAA CAU UAC A)dTdT-3' (SEQ ID NO: 16), antisense 5'-r(UGU AAU GUU AUC AAG UAC C)dGdA-3' (SEQ ID NO: 17)) targeted nucleotides 1722-1742 of the TPTE mRNA sequence (NM_013315). As control a scrambled siRNA duplex (sense 5'-r(UAA CUG UAU AAU CGA CUA G)dTdT-5', 3' (SEQ ID NO: 43) antisense 5'-r(CUA GUC GAU UAU ACA GUU A)dGdA-3' (SEQ ID NO: 44)) was used. For TPTE silencing studies cells were transfected with 100 nm siRNA duplex using RNAiFect transfection reagent (Qiagen) according to the manufacturer's instructions. All functional assays were conducted 24 h after transfection with siRNA duplexes. All results were reproduced with a second set of TPTE siRNA duplexes (sense 5'-r(GAU UGG CAA CCA AGA CUA A)dTdT-3', antisense 5'-r(UAA GUC UUG GUU GCC AAU C)dTdG-3' (SEQ ID NO: 26)) targeting nucleotides 2487-2505. Duplexes for PTEN silencing (5'-r(GGC GUA UAC AGG AAC AAU A)dTdT-3' (SEQ ID NO: 51), antisense 5'-r(UAU UGU UCC UGU AUA CGC C)dTdT-3' (SEQ ID NO: 52)) were directed against nucleotides 1161-1179 (NM_000314).

Cell Migration

Cell migration assays were conducted in transwell chambers with 8.0 μm pore membranes (BD Biosciences) with cells cultured in serum-free medium for 12 h prior to the experiments. For siRNA experiments cells were transferred to serum-free conditions 24 h after transfection with siRNA duplexes as described above. $4\times10^4$ cells in 400 μl serum-free culture medium were added to the upper chamber. The bottom chambers contained 800 μl culture medium supplemented with either FCS, PDGF-BB (Sigma-Aldrich) or SDF-1α/CXCL12 (R&D Systems) as chemoattractants. After 24 hours cells that had migrated to the bottom side of the membrane were fixed in ice-cold methanol; membranes were excised, placed on microscope slides and mounted with Hoechst (Dako) for fluorescence microscopy. Cells in five random visual fields (100× magnification) were counted for each membrane. All experiments were done in triplicates. Effects on chemokinesis of cells was analyzed using the same experimental setup with (i) no chemoattractant added to the upper and lower chamber and (ii) with chemoattractant added to both the upper and lower chamber.

Cell Proliferation Analysis 24 h after transfection with siRNA duplexes $1\times10^4$ cells were cultured in medium supplemented with varying concentrations of FCS for 48 h. Proliferation was analyzed by measuring the incorporation of BrdU into newly synthesized DNA strands using the DELFIA cell proliferation Kit (Perkin Elmer) according to the manufacturer's instructions on a Wallac Victor2 multi-label counter (Perkin Elmer).

Cell Cycle Analysis and Apoptosis

Cells were cultured in medium supplemented with FCS in varying concentrations, harvested after 48 h and stained with propidiumiodide prior to flowcytometric DNA content analysis. Apoptotic cells and cells in S/G2/M phases of the cell cycle were quantified using CellQuest-Software (Becton Dickinson).

In vivo tumor growth analysis and experimental metastasis assay

For analysis of in vivo tumor growth $5\times10^6$ cells (NIH3T3-her2, NIH3T3-her2-eGFP, NIH3T3-her2-TPTE-eGFP, and NIH3T3-her2-TPTE$_{C338S}$-eGFP) were injected subcutaneously into the flanks of NOD/SCID mice (5 animals per group). Tumors were measured periodically with a caliper rule, and the tumor volume was calculated (V=a×b×b/2). For assessment of tumor cell extravasation $1\times10^6$ cells labeled with CFSE (Vybrant CFDA SE Cell Tracer Kit; Molecular probes) were injected into the tail vein of NOD/SCID mice (3 animals per group). Mice were sacrificed after 6 h and Hoechst 33258 labeled cryosections (20 μM) of the lungs were analyzed for extravasated tumor cells by fluorescence microscopy. Tumor cells in 50 random visual fields per lung were counted.

Real-time PCR was used for quantification of the tumor load in the lungs of NOD/SCID mice (4 animals per group) five weeks after i.v. injection of 2×106 MDA-MB-231 cells. DNA was extracted using QIAamp DNA Mini Kit (Qiagen) and a 226 bp fragment of the alpha-satellite region of the human chromosome 17 (sense 5'-CAG CTG ACT AAA CAG AAG CAG-3' (SEQ ID NO: 45); antisense 5'-GAG TTG AAT GCA GTC ATC ACA G-3' (SEQ ID NO: 46)) was amplified from 1 μg DNA. The tumor load was quantified by referring to a standard curve generated by a serial dilution of MDA-MB-231 cells in NIH3T3 mouse fibroblasts.

Statistical Analysis

Statistical analysis of TPTE and CXCR4 expression in tumors in relation to the metastatic rate of the patients was performed using SPSS software (Fisher's exact test).

Example 2

TPTE is Ectopically Expressed in Human Tumors

Figure 1:
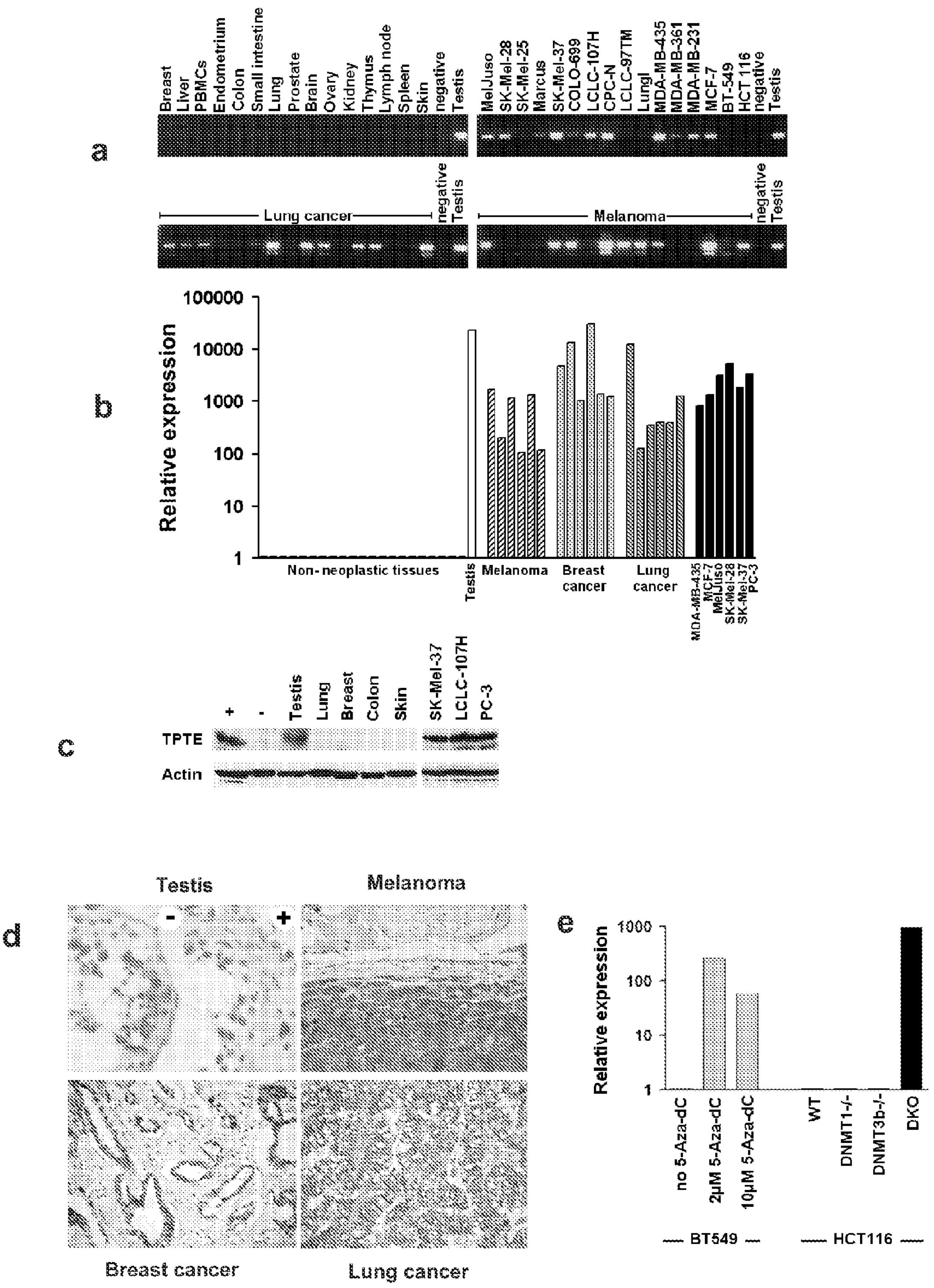
FIG. 1. Selective transcription of TPTE in malignant tissues and cancer cell lines.

TPTE mRNA expression was investigated in a large set of normal and neoplastic tissue specimens. TPTE expression is confined to testis and transcript amounts are below detection limit of highly sensitive RT-PCR in all other normal tissue specimens (FIGS. 1_a,b_). In contrast, strong TPTE expression was detected in 59 of 155 (38%) tumor samples across different cancer types including malignant melanoma (50%), breast carcinomas (47%) and lung carcinomas (55%) as well as in a large set of cancer cell lines (62%) (Tab. 1).

TABLE 1

Expression of TPTE in human tissues and cell lines analyzed by RT-PCR and Real-Time PCR.

| | Positive/tested |
|---|---|
| Normal tissues | |
| Testis | 3/3 |
| Small intestine | 0/2 |
| Colon | 0/3 |
| Liver | 0/2 |
| Lung | 0/3 |
| Lymph node | 0/2 |
| Stomach | 0/2 |
| Spleen | 0/2 |
| Adrenal gland | 0/1 |
| Kidney | 0/3 |

TABLE 1-continued

| Expression of TPTE in human tissues and cell lines analyzed by RT-PCR and Real-Time PCR. | |
|---|---|
| | Positive/tested |
| Esophagus | 0/1 |
| Ovary | 0/2 |
| Thymus | 0/1 |
| Skin | 0/2 |
| Breast | 0/3 |
| Pancreas | 0/2 |
| PBMC's, resting | 0/3 |
| PBMC's, proliferating | 0/3 |
| Prostate | 0/2 |
| Thyroid | 0/2 |
| Endometrium | 0/3 |
| Cerebellum | 0/1 |
| Brain | 0/2 |
| Tumour tissues | |
| Breast cancer | 17/36 (47%) |
| Lung cancer | 25/45 (55%) |
| Mailignant melanoma | 9/18 (50%) |
| Colon cancer | 0/20 |
| Prostate cancer | 3/8 |
| Ovarian cancer | 2/7 |
| Cervical cancer | 1/6 |
| Tumour cell lines | |
| Breast cancer cell lines | 4/5 |
| Lung cancer cell lines | 2/6 |
| Melanoma cell lines | 5/8 |
| Prostate cancer cell lines | 2/2 |

Cloning and sequencing of amplification products from all cell lines tested and from arbitrarily selected tumor derived samples verified them as transcripts derived from TPTE on chromosome 21 p11.

A polyclonal rabbit antibody (pAK2091) against the N-terminus (aa 1-51) of TPTE was used to verify expression data at the protein level. In accordance with the predicted size of TPTE, a 65 kDa band was detected by Western blot analysis in testicular tissue, in a number of tumor cell lines typed positive for constitutive TPTE expression by RT-PCR, as well as in cells transfected with TPTE-cDNA confirming specificity of the antibody (FIG. 1*c*, left). In agreement with RT-PCR data, normal somatic tissues scored negative in Western blot for TPTE, whereas TPTE RT-PCR positive cancer tissues contain significant amounts of TPTE protein (FIG. 1*c*, right).

Immunohistochemistry with pAK2091 on testicular tissue showed specific immunoreactivity in type II spermatocytes and prespermatids in agreement with in situ hybridisation data described recently for the mouse orthologue (Wu, Y. et al., *J. Biol. Chem.* 276, 21745-21753 (2001)) (FIG. 1*d*). Tissue specimens obtained from cancers of lung, breast and prostate as well as malignant melanomas displayed a tumor cell-specific staining in immunohistochemistry. In contrast, adjacent stromal and non-neoplastic epithelial cells (FIG. 1*d*) as well as patient matched normal tissues were not reactive (not shown). Having established TPTE as a molecular tumor marker, the mechanism responsible for its ectopic activation in cancer cells was investigated. DNA methylation at CpG-rich promoters has been reported to be the primary mechanism for silencing of a subset of germline-specific genes in somatic tissues. Genomic demethylation, in turn, appears to be sufficient for aberrant activation of these genes in tumor cells (Koslowski, M. et al., *Cancer Res.* 64, 5988-5993 (2004), De Smet, C. et al., *Mol. Cell Biol.* 19, 7327-7335 (1999)). Sequence analysis of the TPTE promoter revealed a classical CpG island extending from upstream of the first exon over the first exon and intron. Due to the presence of nearly identical promoter sequences on chromosome 7 and chromosome 20, locus-specific bisulfite sequencing for direct analysis of the methylation status of the TPTE promoter in tumor cells could not be applied. Therefore, the effects of global methylation alterations on TPTE expression were studied. TPTE transcription was robustly induced upon treatment of several non-expressing cancer cell lines with the DNA methylation inhibitor 5-Aza-2'-deoxycytidine (dAC) (FIG. 1*e*). Methylation-dependent regulation of TPTE transcription was further evaluated in wild type HCT116 colon cancer cells and descendants with disrupted DNA methyltransferase (DNMT) genes. HCT116WT cells as well as the DNMT3b−/− and DNMT1−/− single knockout variants, which are known to display almost normal or only moderately reduced global DNA methylation (Rhee, I. et al., *Nature* 416, 552-556 (2002)), do not express TPTE. In contrast, HCT116DKO cells lacking both methyltransferases and exhibiting vastly diminished overall DNA methylation resulted in a robust expression of TPTE (FIG. 1*e*). Both assays independently confirmed that DNA methylation is necessary for TPTE silencing and that genomic demethylation as frequently observed in tumors (Ehrlich, M., *Oncogene* 21, 5400-5413 (2002), Feinberg, A. P. & Vogelstein, B., *Nature* 301, 89-92 (1983)) is sufficient for its activation.

Example 3

TPTE is a Plasma Membrane PIP3-Phosphatase

TPTE contains a phosphatase as well as a lipid-binding C2 domain, which have been shown to be essential and sufficient for the lipid phosphatase activity of its homologue PTEN (Lee, J. O. et al., *Cell* 99, 323-334 (1999)). Whereas a lipid phosphatase activity with substrate-specificity for $PIP_3$ and $PI(3,4)P_2$ has previously been shown for the mouse orthologue of TPTE (Wu, Y. et al., *J. Biol. Chem.* 276, 21745-21753 (2001)) in vitro, no enzymatic activity was detected for the human counterpart (Walker, S. M. et al., *Biochem. J.* 360, 277-283 (2001)), leaving PTEN as the only so far known human $PIP_3$-phosphatase. Since the latter study used recombinant protein of bacterial origin, enzymatic activity of human TPTE with eucaryotically produced protein was reassessed. The phosphatase and C2 domains of TPTE and PTEN fused to eGFP were expressed in HEK-293 cells, the proteins purified by immunoprecipitation with anti-eGFP antibody coupled protein A beads and used in a malachite green assay. Equimolar amounts of immunoprecipitates obtained from cells transfected with eGFP or with $TPTE^{C338S}$-eGFP, a TPTE variant mutated at a site critical for the putative phosphatase activity, served as controls to rule out contamination with copurifying phosphatases. Surprisingly, it was found that TPTE but not the respective controls release phosphate specifically from $PIP_3$ at a rate comparable to PTEN (FIG. 2*a*). This finding together with the aberrant activation of TPTE in human cancers indicates that TPTE is involved in phosphoinositide-mediated plasma membrane signalling events in tumor cells.

TPTE-negative cells transfected with TPTE-eGFP as well as cancer cell lines, which express TPTE constitutively were stained with anti-TPTE antibody and investigated by immunofluorescence microscopy. In addition to the previously described localization in the Golgi apparatus and endoplasmatic reticulum (Wu, Y. et al., *J. Biol. Chem.* 276, 21745-21753 (2001)), a major portion of TPTE was found at the plasma membrane (FIGS. 2*b*, 2*c*). TPTE appears accentuated at membrane ruffles and at lateral margins of membrane protrusions including pseudopodia and filopodia, but not at the tips of such structures (FIG. 2*d*). To dissect the spatial association of TPTE with plasma membrane phosphoinositides colocalisation studies with pleckstrin domain-eGFP fusion proteins were performed using the PLC-δ1-PH (phosholipase C-δ1 pleckstrin homology) (Tall, E. G. et al., *Curr. Biol.* 10, 743-746 (2000)) and the AKT-PH (Watton, S. J. & Downward, J., *Curr. Biol.* 9, 433-436 (1999)) domains, which selectively bind to either PIP(4,5)$P_2$ ($PIP_2$) or 3'-phosphorylated phospholipids, respectively. Remarkably, staining of cells coexpressing TPTE cDNA and eGFP-tagged PH-domains with pAK2091 demonstrated an almost complete overlap of TPTE with PLC-δ1-PH-eGFP (FIG. 2*f*) but not with AKT-PH-eGFP, establishing that TPTE colocalizes with $PIP_2$ (FIG. 2*e*).

A trafficking assay, which allows to indirectly determine membrane $PIP_3$ levels (Halet, G., *Biol. Cell* 97, 501-518 (2005)), demonstrated that cotransfection of TPTE cDNA but not $TPTE_{C338S}$-cDNA together with AKT-PH-eGFP resulted in a complete redistribution of AKT-PH-eGFP from the plasma membrane to the cytosol in fibroblasts with PI3K overactivation due to HER-2/neu transformation (FIG. 2*f*), proving that TPTE decreases plasma membrane $PIP_3$ levels. Altogether these observations prove that TPTE metabolizes $PIP_3$ and imply that TPTE may be involved in spatial control of plasma membrane phosphoinositides in tumor cells.

Example 4

Use of siRNA in Silencing TPTE Expression

The effects of small interfering RNA (siRNA) induced gene silencing of TPTE in breast cancer, prostate cancer and malignant melanoma cell lines, which endogenously express the tumor-associated phosphatase TPTE were analyzed. Quantitative RT-PCR and Western blot demonstrated that TPTE specific siRNA duplexes induce a robust knockdown of TPTE transcripts and protein without affecting cellular PTEN levels (FIG. 3*a*).

First, levels of Ser473 phosphorylated AKT (pAKT) were quantified as a measure of cellular $PIP_3$ signalling. siRNA mediated downregulation of TPTE resulted in a substantial upregulation of cellular pAKT in all tumor lines tested (FIG. 3*b*) establishing that TPTE counteracts PI3K signaling in cancer cells. Upregulation of pAKT by TPTE silencing was most prominent in PC-3 cells, which lack PTEN, suggesting that endogenous TPTE may at least partially compensate for loss of PTEN activity in tumor cells. Most importantly, upregulation of pAKT upon TPTE silencing translates into a reduced growth factor-dependency of the respective tumor cells giving rise to sustained proliferation rates (FIG. 3*c*) and protection from apoptosis even under serum starvation in all TPTE positive tumor lines tested (FIG. 3*d*).

In order to clarify the effects directly mediated by the phosphatase activity of TPTE, Her2/neu transformed fibroblasts stably transfected with either TPTE or the catalytically inactive $TPTE_{C338S}$ variant were used.

Her2/neu transformed fibroblasts (NIH3T3-her2) display permanent AKT activation (FIG. 3*e*) resulting from constitutively PI3K overactivation associated with increased cellular $PIP_3$ levels (FIG. 3*f*). As a consequence, these cells are resistant to apoptosis and sustain proliferation under growth-factor starvation (FIG. 3*h*). Expression of TPTE but not mutated $TPTE_{C338S}$ downregulates cellular $PIP_3$ (FIG. 3*f*), reduces pAKT levels (FIG. 3*g*), resets proliferation and survival autonomy and induces strictly serum-dependent proliferation and rapid onset of a G0/G1 cell cycle block upon growth factor removal (FIG. 3*h*). Notably, growth of NIH3T3-her2 cells expressing TPTE in immunocompromised mice was markedly reduced compared to controls lacking the phosphatase activity, but were still tumorigenic (FIG. 3*g*). These findings demonstrate that TPTE counteracts upstream oncogene-induced PI3K overactivation by metabolizing $PIP_3$ and renders tumor cell growth and survival dependent on external growth factors without abrogating tumorigenecity.

Example 5

TPTE Promotes Tumor Cell Chemotaxis

TPTE specific siRNA duplexes but not control duplexes reduced tumor cell migration towards PDGF or SDF-1/CXCL12 gradients in all tumor cell lines tested in transwell migration assays and chemokine based invasion assays (FIG. 4*a*)

To exclude siRNA off target activity these findings were confirmed with a second set of TPTE specific siRNA duplexes and controls. Moreover, it was observed that TPTE but not its catalytically inactive mutant variant potentiates HER-2/neu effects on cell migration. The increased baseline migration rate of NIH3T3-her2 cells (Dittmar, T. et al., *FASEB J.* 16, 1823-1825 (2002)) owing to transformation by this oncogene is further augmented upon coexpression of TPTE (FIG. 4*b*). Such double positive cells migrate efficiently even towards lowest gradients of chemoattractants (FIG. 4*c*) indicating that a combination of PI3K overactivation and TPTE expression promotes both chemokine sensing and efficient chemotactic migration. In line with this, expression of TPTE but not $TPTE_{C338S}$, results in profound morphological changes, i.e. the transition from a rounded cell shape to a polarized, polymorphic phenotype with pseudo- and filopodia (FIG. 4*d*). As shown for constitutively expressing cancer cell lines (FIG. 2*d*), TPTE is strongly enriched in these protrusions suggesting that the lipid phosphatase is directly involved in the generation of filopodial extensions.

The chemotaxis promoting activity observed for TPTE is surprising in particular in light of previous data for PTEN, which exhibits the same catalytic $PIP_S$ phosphatase activity as TPTE, but was reported to inhibit migration (Tamura, M. et al., *Science* 280, 1614-1617 (1998)). However, these studies were based on tumor cells transfected with PTEN cDNA. In contrast, a recent report (Li, Z. et al., *Nat. Cell Biol.* 7, 399-404 (2005), Meili, R., Sasaki, A. T. & Firtel, R. A., *Nat. Cell Biol.* 7, 334-335 (2005)) which made use of siRNA for PTEN knockdown demonstrated clearly that PTEN is essential for SDF-1 mediated chemotaxis in transformed Jurkat cells.

Robust reduction of PTEN expression by specific siRNA duplexes resulted in marked and selective reduction of chemotaxis (FIG. 4*e*) but not of chemokinesis in all investigated PTEN positive tumor cell lines. The lack of effects of PTEN siRNA in PTEN deficient PC-3 cells ruled out that the observed inhibition on chemotactic migration is mediated by siRNA off target activity. Importantly, inhibition of both phosphatases resulted in nearly complete abrogation of chemotaxis. Analysis of cellular $PIP_3$ levels in siRNA treated cells demonstrate that abrogation of both, TPTE and PTEN by combined siRNA results in a more profound upregulation of cellular $PIP_3$ as compared to the increase of $PIP_3$ levels in single siRNA treated cells (FIG. 4*f*). This together with the observation, that inhibition of both phosphatases resulted in a more intense increase of cellular pAKT (FIG. 4*g*) underlines that activities of TPTE and PTEN are additive for promotion of tumor cell chemotaxis and reduction of $PIP_3$/AKT signaling.

Example 6

TPTE Promotes Metastatic Spread

Chemotaxis mediated by growth factor receptors like EGF and PDGF or chemokine receptors such as CXCR4 and CCR7 promotes tumor invasion and metastasis (Muller, A. et al., *Nature* 410, 50-56 (2001), Staller, P. et al., *Nature* 425, 307-311 (2003)). To investigate the impact of TPTE in metastasis, tumor cell extravasation, which is a critical step for metastatic dissemination of cancer cells mediated by chemotaxis (Chambers, A. F., Groom, A. C. & MacDonald, I. C., *Nat. Rev. Cancer* 2, 563-572 (2002)) was studied. siRNA treated, fluorophore-labeled MDA-MB-231 or MCF-7 breast cancer cells were injected into the tail vein of NOD/SCID mice. Six hours later animals were sacrificed and the number of tumor cells extravasated into the lungs was quantified in whole mount lung sections by fluorescence microscopy. For both tumor cell lines siRNA mediated knockdown of TPTE significantly reduced the number of extravasated cells (FIG. 5*a*). Quantification of submacroscopic metastatic tumor lesions in the lungs of mice several weeks after inoculation with metastases forming breast cancer (MDA-MB-231, MCF-7) or malignant melanoma (MelJuso) cells by human microsatellite specific PCR demonstrated a 100-1000 fold reduction of the tumor load in animals which received tumor cells transiently transfected with TPTE siRNA (FIG. 5*b*).

Independently, experimental metastases assays with MDA-MB-231 in nude mice giving rise to macroscopic lesions confirmed these striking findings and proved a crucial role of TPTE for metastatic dissemination (FIG. 5*c*).

Example 7

TPTE and CXCR4 are Markers for Tumor Metastasis

It was assessed whether the strong promigratory and metastasis promoting activity of TPTE is of relevance for the metastatic spread of tumors. To this end, independently collected samples from 34 breast cancer patients from a thoroughly characterized cohort (Ahr, A. et al., *Lancet* 359, 131-132 (2002)) and 24 non-small cell lung cancer specimens were typed for TPTE expression by real-time RT-PCR. There was no significant correlation between TPTE expression and tumor stage or differentiation grade. However, TPTE positive tumors displayed significantly more regional lymphatic metastasis (76%) and distant metastasis (21%) at the time of diagnosis than TPTE negative primaries (37% and 0%) (Tab. 2a). CXCR4 expression is also a metastasis predicting marker for various cancers. Therefore, the same set of samples was tested for CXCR4 expression. Indeed, CXCR4 positive cancers (n=23) showed a significantly higher rate of distant metastasis (26%) as compared to CXCR4 negative cancers (3%). Importantly, TPTE and CXCR4 expression do not correlate and both molecules represent independent metastasis predictors (FIG. 5*c*). Cancers with combined expression of TPTE and CXCR4 exhibit a highly increased metastasis rate (60%) whereas tumors lacking either TPTE, CXCR4 or both molecules display an even reduced risk for metastasis (2%, p<0.00005, Tab. 2c) indicating that co-expression of both molecules is important for metastatic spread of cancer, in particular breast and lung cancer.

TABLE 2a

TPTE expression correlates with metastatic spread.

| Status TPTE-Expression | metastatic site: lymph nodes | metastatic site: distant |
|---|---|---|
| TPTE positive n = 33 | 25 (76%) | 7 (21%) |
| TPTE negative n = 25 | 9 (37%) | 0 (0%) |
| Total n = 58 | P < 0.003 | P < 0.02 |

TABLE 2b

CXCR4 expression correlates with distant metastasis.

| Status CXCR4-Expression | metastatic site: lymph nodes | metastatic site: distant |
|---|---|---|
| CXCR4 positive N = 23 | 14 (61%) | 6 (26%) |
| CXCR4 negative n = 35 | 20 (57%) | 1 (3%) |
| Total n = 58 | P = 0.5 | P < 0.02 |

TABLE 2c

Simultaneous expression of TPTE and CXCR4 highly correlates with distant metastasis.

| Status TPTE and CXCR4-Expression | metastatic site: lymph nodes | metastatic site: distant |
|---|---|---|
| TPTE positive AND CXCR4 positive n = 10 | 7 (70%) | 6 (60%) |
| TPTE negative OR CXCR4 negative n = 48 | 27 (56%) | 1 (2%) |
| Total n = 58 | P = 0.33 | P < 0.00005 |

The invention claimed is:

1. A method of treating a cancer, metastasis of a cancer or relapse of a cancer comprising administering an effective amount of a pharmaceutical composition comprising:

(i) an agent which is effective in reducing or inhibiting expression or activity of TPTE and/or which binds to TPTE and has tumor destroying or tumor inhibiting activity when administered to a patient, and (ii) an agent which is effective in reducing or inhibiting expression or activity of CXCR4 and/or which binds to CXCR4 and has tumor destroying or tumor inhibiting activity when administered to a patient, wherein the agent is selected from (a) an antisense nucleic acid which hybridizes selectively with the nucleic acid coding for TPTE and an antisense nucleic acid which hybridizes selectively with the nucleic acid coding for CXCR4; and (b) an antibody which binds selectively to TPTE and an antibody which binds selectively to CXCR4, and wherein the cancer is characterized by expression of TPTE and CXCR4.

2. The method of claim 1, wherein the cancer is a lung tumor, a breast tumor, a prostate tumor, a melanoma, a colon tumor, a gastric tumor, a pancreatic tumor, an ENT tumor, a renal cell carcinoma or a cervical carcinoma, a colon carcinoma or a mammary carcinoma.

3. The method of claim 1, wherein the agent is an siRNA comprising a sense RNA strand and an antisense RNA strand, wherein the sense and antisense RNA strands form an RNA duplex, and wherein the sense RNA strand comprises a nucleotide sequence substantially identical to a target sequence of about 19 to about 25 contiguous nucleotides in TPTE mRNA or a nucleotide sequence substantially identical to a target sequence of about 19 to about 25 contiguous nucleotides in CXCR4 mRNA.

4. The method of claim 3, wherein for the siRNA directed against a nucleic acid coding for TPTE, the target sequence has a nucleic acid sequence selected from the group consisting of nucleotide positions 3-21 of SEQ ID NO: 15, nucleotide positions 3-21 of SEQ ID NO: 18, nucleotide positions 3-21 of SEQ ID NO: 21, nucleotide positions 3-21 of SEQ ID NO: 24, nucleotide positions 3-21 of SEQ ID NO: 27, nucleotide positions 3-21 of SEQ ID NO: 30, and nucleotide positions 3-21 of SEQ ID NO: 33.

5. The method of claim 3, wherein for the siRNA directed against a nucleic acid coding for TPTE, the sense RNA strand has the sequence of SEQ ID NO: 16 and the antisense RNA strand has the sequence of SEQ ID NO: 17, or sense RNA strand has the sequence of SEQ ID NO: 19 and the antisense RNA strand has the sequence of SEQ ID NO: 20, or the sense RNA strand has the sequence of SEQ ID NO: 22 and the antisense RNA strand has the sequence of SEQ ID NO: 23, or the sense RNA strand has the sequence of SEQ ID NO: 25 and the antisense RNA strand has the sequence of SEQ ID NO: 26, or the sense RNA strand has the sequence of SEQ ID NO: 28 and the antisense RNA strand has the sequence of SEQ ID NO: 29, or the sense RNA strand has the sequence of SEQ ID NO: 31 and the antisense RNA strand has the sequence of SEQ ID NO: 32, or the sense RNA strand has the sequence of SEQ ID NO: 34 and the antisense RNA strand has the sequence of SEQ ID NO: 35.

6. The method of claim 1, wherein the antibody is coupled to a therapeutic substance.

7. The method of claim 1, wherein the agent is specific for cells expressing or abnormally expressing TPTE or is specific for cells expressing or abnormally expressing CXCR4.

8. The method of claim 1, wherein the antibody is a monoclonal antibody.

9. The method of claim 1, wherein the antibody is a chimeric or humanized antibody, a fragment of a natural antibody, or a synthetic antibody.

* * * * *